(12) United States Patent
Hunt et al.

(10) Patent No.: US 6,316,444 B1
(45) Date of Patent: Nov. 13, 2001

(54) SRC KINASE INHIBITOR COMPOUNDS

(75) Inventors: Julianne A. Hunt; Sander G. Mills; Peter J. Sinclair; Dennis M. Zaller, all of Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 33 days.

(21) Appl. No.: 09/603,699

(22) Filed: Jun. 26, 2000

Related U.S. Application Data

(60) Provisional application No. 60/141,597, filed on Jun. 30, 1999.

(51) Int. Cl.[7] .................... A61P 37/06; A61K 31/5377; A61K 31/506; C07D 401/14; C07D 403/14

(52) U.S. Cl. .................... 514/231.2; 514/234.2; 514/234.5; 514/235.8; 514/227.8; 514/228.5; 514/228.2; 514/249; 514/261; 514/275; 514/433; 540/598; 544/277; 544/278; 544/283; 544/284; 544/296; 544/310; 544/119; 544/117; 544/60; 544/61; 544/62; 544/350

(58) Field of Search .................... 544/277, 278, 544/283, 284, 296, 310, 119, 117, 60, 61, 62, 350, 122; 540/598; 514/261, 275, 231.2, 234.2, 234.5, 235.8, 227.8, 228.5, 228.2, 433, 249

(56) References Cited

U.S. PATENT DOCUMENTS

| | | | |
|---|---|---|---|
| 3,646,049 | 2/1972 | Hoff et al. | 260/302 H |
| 3,743,738 | 7/1973 | Hoff et al. | 424/270 |
| 4,806,649 | 2/1989 | Strupczewski | 546/193 |
| 5,521,184 | 5/1996 | Zimmermann | 514/252 |
| 5,593,997 | 1/1997 | Dow et al. | 514/258 |
| 5,902,813 | 5/1999 | Teuber et al. | 514/275 |
| 5,958,934 | 9/1999 | Berger et al. | 514/272 |

FOREIGN PATENT DOCUMENTS

| | | |
|---|---|---|
| 0 233 461 A2 | 8/1987 | (EP) . |
| 0 564 409 B1 | 10/1993 | (EP) . |
| 0 588 762 A1 | 3/1994 | (EP) . |
| WO 91/16313 | 10/1991 | (WO) . |
| WO 93/07124 | 4/1993 | (WO) . |
| WO 95/09847 | 4/1995 | (WO) . |
| WO 95/09851 | 4/1995 | (WO) . |
| WO 95/09852 | 4/1995 | (WO) . |
| WO 95/09853 | 4/1995 | (WO) . |
| WO 96/35678 | 11/1996 | (WO) . |
| WO 97/19065 | 5/1997 | (WO) . |
| WO 97/40019 | 10/1997 | (WO) . |
| WO 98/02434 | 1/1998 | (WO) . |
| WO 98/11095 | 3/1998 | (WO) . |
| WO 98/18782 | 5/1998 | (WO) . |
| WO 99/09845 | 3/1999 | (WO) . |
| WO 99/41253 | 8/1999 | (WO) . |

*Primary Examiner*—Mark L. Berch
*Assistant Examiner*—Kahsay Habte
(74) *Attorney, Agent, or Firm*—Valerie J. Camara; Mark R. Daniel

(57) ABSTRACT

Pyrimidine compounds (Formula I), or their pharmaceutically acceptable salts, hydrates, solvates, crystal forms and individual diastereomers, and pharmaceutical compositions including the same, which are inhibitors of tyrosine kinase enzymes, and as such are useful in the prophylaxis and treatment of protein tyrosine kinase-associated disorders, such as immune diseases, hyperproliferative disorders and other diseases in which inappropriate protein kinase action is believed to play a role, such as cancer, angiogensis, atheroscelerosis, graft rejection, rheumatoid arthritis and psoriasis.

41 Claims, No Drawings

SRC KINASE INHIBITOR COMPOUNDS

This application claims the benefit under 35 U.S.C. 119(e) of Provisional Application Ser. No. 60/141,597 filed on Jun. 30, 1999.

BACKGROUND OF THE INVENTION

Tyrosine-specific Protein Kinases (PTKs) are a family of enzymes which catalyze the transfer of the terminal phosphate of adenosine triphosphate (ATP) to tyrosine residues in protein substrates [for review see: Hunter, T; Protein modification: phosphorylation on tyrosine residue; *Curr Opin Cell Biol* 1989; 1:1168–1181]. The first members of this class of enzymes to be identified were PTKs encoded by viral oncogenes, which were capable of cell transformation (ie. pp60v-src and pp98v-fps). Later it was shown that there were normal cellular counterparts of these viral gene products (ie. pp60C-src and pp98c-fps). Since that discovery, a large number of genes encoding PTKs have been identified [for review see Hunter, T; Protein kinase classification; *Methods Enzymol* 1991; 200:3–37]. These include growth factor receptor PTKs such as the insulin and epidermal growth factor receptors, as well as non-receptor PTKs such as ZAP-70 and Lck. Although the molecular details have yet to be fully elucidated, PTK-mediated phosphorylation of tyrosine residues on protein substrates leads to the transduction of intracellular signals that regulate a variety of intracellular processes such as growth, transport, motility, and senescence. Many disease states are dependent on these cellular functions. Therefore, inhibitors of tyrosine kinases are useful for the prevention and chemotherapy of disease states that are dependent on these enzymes.

For example, tyrosine kinase inhibitors are useful for inhibiting T-cell activation and thus they are useful as immunosuppressive agents for the prevention or treatment of graft rejection following transplant surgery and for the prevention or treatment of autoimmune diseases such as rheumatoid arthritis and psoriasis. Graft rejection following transplant surgery is a common occurrence which arises when foreign antigens are recognized by the host immune system. In an effort to protect itself from the foreign tissue, the host immune system is then activated to release an arsenal of antibodies, soluble lymphokines, and cytotoxic lymphocytes which attack the foreign tissue, resulting in complications which often end in graft rejection. Similarly, a breakdown in self-tolerance can result in immune system attacks against the body's own tissues. These attacks can lead to autoimmune and chronic inflammatory diseases. Since T cells are the key regulators of these immune system attacks, inhibitors of T cell activation are useful therapeutic agents.

Currently the leading medicinal agent for the prevention or treatment of graft rejection is Cyclosporin A, approved by the United States Food and Drug Administration in 1983. Cyclosporin A is extremely effective at preventing transplant rejection and is efficacious in the treatment of autoimmune disorders such psoriasis, rheumatoid arthritis, inflammatory bowel disease, and type I diabetes. It work by forming complexes with a specific protein which can then inhibit the catalytic activity of calcineurin, a phosphatase that plays a key role in transducing signals from the T cell receptor (TcR) to the nucleus. However, calcineurin is ubiquitously expressed and is involved in many other signal transduction pathways. As a result, Cyclosporin A suffers drawbacks in that it can cause kidney failure, liver damage and ulcers; which in many cases can be very severe. Consequently, Cyclosporin A has a very narrow therapeutic index and is rarely used to treat chronic autoimmune diseases. Safer drugs which are more selective in their ability to affect the immune response system and which have fewer side effects are constantly being pursued. Thus, there is a continuing need and a continuing search in this field of art for alternative therapies. The Src-family protein tyrosine kinase, Lck, is upstream of calcineurin in the TcR-mediated signaling cascade. Lek is expressed almost exclusively in T cells and its catalytic activity is required for T cell signal transduction [for review see: Anderson S J, Levin S D, Perlmutter, R M; Involvement of the protein tyrosine kinase p56lck in T cell signaling and thymocyte development; *Adv Immunol* 1994; 56:151–178]. Thus, a potent Lck-selective kinase inhibitor would make a promising drug candidate.

Lck is one of 8 known members of the human Src-family of protein tyrosine kinases. The other members are Src, Fyn, Lyn, Fgr, Hck, Blk, and Yes. As a consequence of alternative mRNA splicing, Fyn exists as two distinct gene products, Fyn(T) and Fyn(B), that differ at their ATP binding sites. All Src-family kinases contain an N-terminal myristoylation site followed by a unique domain characteristic of each individual kinase, an SH3 domain that binds proline-rich sequences, an SH2 domain that binds phosphotyrosine-containing sequences, a linker region, a catalytic domain, and a C-terminal tail containing an inhibitory tyrosine. The activity of Src-family kinases is tightly regulated by phosphorylation. Two kinases, Csk and Ctk, can down-modulate the activity of Src-family kinases by phosphorylation of the inhibitory tyrosine. This C-terminal phosphotyrosine can then bind to the SH2 domain via an intramolecular interaction. In this closed state, the SH3 domain binds to the linker region, which then adopts a conformation that impinges upon the kinase domain and blocks catalytic activity. Dephosphorylation of the C-terminal phosphotyrosine by intracellular phosphatases such as CD45 and SHP-1 can partially activate Src-family kinases. In this open state, Src-family kinases can be fully activated by intermolecular autophosphorylation at a conserved tyrosine within the activation loop.

Src-family kinases display a variety of tissue-specific expression patterns. Src, Fyn(B), Yes, and Lyn are found in a broad range of tissues with especially high levels of expression in neuronal and hematopoietic cells. The expression of these particular Src-family kinases overlap to a great extent, however no cell types have been found that express all four of them. Expression of Lck, Fyn(T), Fgr, Hck, and Blk is restricted to cells of the hematopoietic lineage. In general, myeloid cells co-express Hck, Fgr, and Lyn; immature B cells co-express Hck, Lyn, and Blk; and mature B cells co-express Hck, Lyn, Blk, Fgr, and Fyn(T). T cells predominantly express Lck and Fyn(T). Lck is also expressed in NK cells.

A complex cascade of biochemical events mediates signal transduction in T cells [for review see: Chan A C, Desai D M, Weiss A; The role of protein tyrosine kinases and protein tyrosine phosphatases in T cell antigen receptor signal transduction; *Annu Rev Immunol* 1994;12:555–5921. While many proteins involved in this signaling cascade have been identified, the molecular details of this process are just beginning to be unraveled. The antigen-specific α/β TcR heterodimer is noncovalently associated with CD3-ε, -δ and ζ polypeptide chains. In the current paradigm of T cell activation, stimulation of the TcR by MHC/peptide complexes on the surface of antigen presenting cells (APCs) leads to the rapid activation of Lck. Activated Lck then phosphorylates CD3 and ζ proteins on tyrosine residues within conserved motifs known as ITAMs (Immunoreceptor-associated Tyrosine-based Activation Motifs). Another protein tyrosine kinase, ZAP-70, is recruited to the TcR complex via association of its tandem pair of SH2 domains to doubly phosphorylated ITAMs. Lck, in turn, activates TcR-associated ZAP-70 by phosphorylation of tyrosine 493 in the ZAP-70 activation loop. Activated ZAP-70 goes on to phosphorylate a variety of downstream adapter molecules such as LAT, SLP-76, and HS1. Lck can also phosphorylate additional protein substrates in activated T cells. One important substrate is Vav, a guanine nucleotide exchange protein that is regulated by Lck phosphorylation. Activated Vav mediates GDP release by Rac/Rho family members which, in turn, leads to the reorganization of the actin cytoskeleton, an event that is necessary for T cell activation. In addition to TcR recognition of MHC/peptide complexes on the surface of APCs, there are many co-receptor pairs that are important in T cell-APC interactions. Of note are CD4 and CD8, which are associated with Lck and bind to nonpolymoiphic regions of MHC Class II and Class I molecules, respectively. Other co-receptor pairs include CD28/B7, CTLA-4/B7, LFA-2/LFA-3, LFA-1/ICAM, CD40/CD40L, SLAM/SLAM, and etc./etc. This vast array of cell-cell molecular interactions stabilizes T cell/APC conjugates and initiates additional intracellular signaling cascades. Signals derived from co-receptor engagement are integrated with signals derived from stimulation of the TcR to determine the magnitude and the quality of the T cell response.

Genetic data clearly validate Lck as an excellent therapeutic target. Mice in whom Lck expression was perturbed by either genetic deletion or by overexpression of a catalytically inactive version of Lck exhibited an early block in T cell development. The small number of mature T cells in the periphery of Lck-deficient mice were inefficient at transducing signals from the TcR and could not mediate a vigorous response to antigenic challenge. NK cells from Lck deficient mice appeared to function normally. No functional defects outside of the immune system were noted in these animals. In addition there is a report in the literature of a human patient with low levels of Lck expression due to an inability to properly splice Lck mRNA [see: Goldman F D, Ballas Z K, Schutte B C, Kemp J, Hollenback C, Noraz N, Taylor N.; Defective expression of p56lck in an infant with severe combined Immunodeficiency; *J Clin Invest* 1998; 102:421–429]. This patient presented with Severe Combined Immunodeficiency Syndrome (SCID). Again, no other phenotypic disturbances outside of this immune system disorder were noted. These results strongly suggest that Lck inhibitors would be effective in suppressing T cell mediated immune responses without causing mechanism-based toxicity.

SUMMARY OF THE INVENTION

The present invention provides substituted pyn'midine compounds of Formula 1:

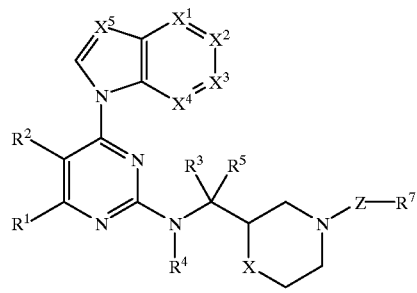

or a pharmaceutically acceptable salts, hydrates, solvates, crystal forms, and individual diastereomers thereof (as defined below), for use as a protein tyrosine kinase inhibitor. The invention also includes the use the compounds of Formula I in the prophylaxis and treatment of immune diseases, hyperproliferative disorders and other diseases in which inappropriate protein kinase action is believed to have a role.

DETAILED DESCRIPTION OF THE INVENTION

A compound of Formula I

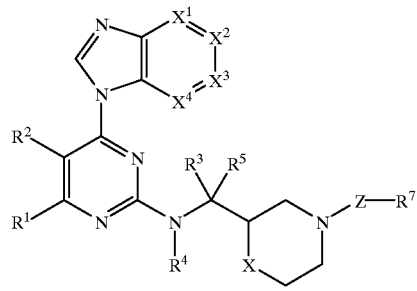

or pharmaceutically acceptable salts, hydrates, solvates, crystal forms and individual diastereomers thereof, wherein $R^1$ and $R^2$ are independently:
  a) H,
  b) halo( Br, Cl, I, or F),
  c) OH,
  d) SH,
  e) CN,
  f) $NO_2$,
  g) $R^9$,
  h) $OR^9$,
  i) $O(C=O)R^9$,
  j) $O(C=O)OR^9$,
  k) $O(C=O)NHR^9$,
  l) $O(C=O)NR^9R^{10}$,
  m) $SR^9$,
  n) $S(O)R^9$,
  o) $S(O)_2R^9$,
  p) $C(=O)R^9$,
  q) $C(=O)OR^9$,
  r) $C(=O)NHR^9$,
  s) $C(=O)NR^9R^{10}$,
  t) $NH_2$,
  u) $NHR^9$, v) NR$^9$R$^{10}$,
w) NHC(=O)R$^9$,
x) NHC(=O)OR$^9$,
y) NR$^9$C(=O)R$^{10}$,
z) NR$^9$C(=O)NHR$^{10}$,
aa) NR$^9$C(=O)NR$^{10}$R$^{11}$,
ab) SO$_2$NHR$^9$,
ac) SO$_2$NR$^9$R$^{10}$,
ad) NHSO$_2$R$^9$,
ae) NR$^9$SO$_2$R$^{10}$, or
af) R$^1$ and R$^2$ can join together to form a fused methylenedioxy ring or a fused 6-membered aromatic ring;

R$^3$ and R$^5$ are independently:
a) H,
b) C$_1$–C$_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) R$^3$ and R$^5$ taken together can represent =O;

R$^4$ is:
a) H, or
b) C$_1$–C$_6$-alkyl,
c) C$_1$–C$_6$-alkoxyl, or
d) R$^4$ and R$^8$ can join together to form a 5- or 6-membered ring with —CHR$^9$—, —CH$_2$CHR$^9$—, or —CHR$^9$CH$_2$—;

—X$^1$—X$^2$—X$^3$—X$^4$— is:
a) —CR$^6$=CR$^6$—CR$^{6a}$=CR$^6$—,
b) —CR$^{6a}$=CR$^6$—CR$^6$=CR$^6$—,
c) —CR$^6$=CR$^{6a}$—CR$^6$=CR$^6$—,
d) —CR$^6$=CR$^6$—CR$^6$=CR$^{6a}$—,
e) —N=CR$^6$—CR$^6$=CR$^6$—,
f) —CR$^6$=N—CR$^6$=CR$^6$—,
g) —CR$^6$=CR$^6$—N=CR$^6$—,
h) —CR$^6$=CR$^6$—CR$^6$=N—,
i) —N=CR$^6$—N=CR$^6$—,
j) —CR$^6$=N—CR$^6$=N—,
k) —CR$^6$=N—N=CR$^6$—, or
l) —N=CR$^6$—CR$^6$=N—;

X$^5$ is N or CH;

R$^6$ and R$^{6a}$ are independently:
a) H,
b) halo( Br, Cl, I, or F),
c) OH,
d) SH,
e) CN,
f) NO$_2$,
g) N$_3$,
h) N$_2$+BF$_4$−,
i) R$^9$,
j) OR$^9$,
k) O(C=O)R$^9$,
l) O(C=O)OR$^9$,
m) O(C=O)NHR$^9$,
n) O(C=O)NR$^9$R$^{10}$,
o) SR$^9$,
p) S(O)R$^9$,
q) S(O)$_2$R$^9$,
r) C$_1$–C$_6$-alkyl, unsubstituted or substituted with one, two, or three substituents selected from R$^9$, R$^{10}$, and R$^{11}$,
s) C(=O)R$^9$,
t) C(=O)OR$^9$,
u) C(=O)NHR$^9$,
v) C(=O)NR$^9$R$^{10}$,
w) C(=O)N(OR$^9$)R$^{10}$,
x) NH$_2$,
y) NHR$^9$,
z) NHC$_1$–C$_6$-alkyl, unsubstituted or substituted with one, two, or three substituents selected from R$^9$, R$^{10}$, and R$^{11}$,
aa) NR$^9$R$^{10}$,
ab) NHC(=O)R$^9$,
ac) NR$^9$C(=O)R$^{10}$,
ad) NHC(=O)NHR$^9$,
ae) NR$^9$C(=O)NHR$^{10}$,
af) NR$^9$C(=O)NR$^{10}$R$^{11}$,
ag) SO$_2$NH$_2$,
ah) SO$_2$NHR$^9$,
ai) SO$_2$NR$^9$R$^{10}$,
aj) NHSO$_2$R$^9$,
ak) NR$^9$SO$_2$R$^{10}$, or
al) NHP(=O)(OC$_1$–C$_6$-alkyl)$_2$,
am) R$^6$ and R$^{6a}$ when on adjacent carbons can be joined to form a 5- or 6-membered ring having the following bridging atoms, when read from right to left, or left to right:
  i) —CH=CH—CH=CH—,
  ii) —OCH$_2$O—,
  iii) —C(O)N(R$^9$)C(O)—,
  iv) —CH$_2$N(R$^9$)CH$_2$—,
  v) —N=CRNHC(O)—,
  vi) —C(O)NHCH=N—,
  vii) —C(O)OC(O)—,
  viii) —NHC(O)NHC(O)—,
  ix) —C(O)NHC(O)NH—,
  x) —N=CHNH—,
  xi) —NHCH=N—,
  xii) —NR$^9$CH=N—,
  xiii) —N=CHNR$^9$—, or
  xiv)

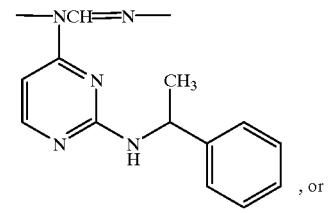

, or

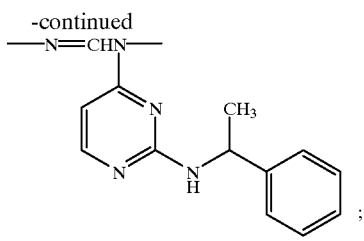

xv)

R⁷ is:
a) H,
b) R⁹,
c) OR⁹,
d) NH₂,
e) NHR⁹, or
f) NR⁹R¹⁰;

X is O, S, SO, SO₂, NR⁸;

Z is C=O, SO₂, P(=O)(OR⁹) or a single bond; and

R⁸ is:
a) H,
b) R⁹,
c) SO₂R⁹,
d) C(=O)R⁹,
e) C(=O)OR⁹,
f) C(=O)NHR⁹,
f) C(=O)NR⁹R¹⁰;

R⁹, R¹⁰ and R¹¹ are independently:
a) C₁–C₆-perfluoroalkyl,
b) C₁–C₆-alkyl, unsubstituted or substituted with one, two, or three substituents selected from oxo, X', Y' and Z',
c) C₂–C₆-alkenyl, unsubstituted or substituted with one, two, or three substituents selected from oxo, X', Y' and Z',
d) C₂–C₆-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two, three or four substituents selected from oxo, X', Y', and Z', or
g) C₃–C₆-cycloalkyl, unsubstituted or substituted with one, two, or three substituents selected from oxo, X', Y' and Z'; X', Y' and Z' independently are selected from:
a) H,
b) halo,
c) CN,
d) NO₂,
e) hydroxy,
f) C₁–C₆-perfluoroalkyl,
g) C₁–C₆-alkoxyl, unsubstituted or substituted with aryl, wherein aryl is defined as phenyl or naphthyl,
h) (C=O)(C₁–C₆-alkyl), unsubstituted or substituted with aryl, wherein aryl is defined as phenyl or naphthyl,
i) (C=O)O(C₁–C₆-alkyl), unsubstituted or substituted with aryl, wherein aryl is defined as phenyl or naphthyl,
j) (C=O)NH(C₁–C₆-alkyl),
k) (C=O)N(C₁–C₆-alkyl)₂,
l) NH₂,
m) NHC₁–C₆-alkyl, wherein alkyl is unsubstituted or substituted with aryl or NH₂,
n) N(C₁–C₆-alkyl)₂,
o) NHaryl, wherein aryl is defined as phenyl or naphthyl, unsubstituted or substituted with one, two, or three substituents selected from halo, phenyl, CN, NO₂, hydroxy, C₁–C₆-alkyl, C₁–C₆-alkoxyl, NH₂, NHC₁–C₆-alkyl, N(C₁–C₆-alkyl)₂, (C=O)(C₁–C₆-alkyl), (C=O)O(C₁–C₆-alkyl), (C=O)NH(C₁–C₆-alkyl), (C=O)N(C₁–C₆-alkyl)₂, NH(C=O)(C₁–C₆-alkyl),
p) NHheterocyclyl, wherein heterocyclyl is unsubstituted or substituted with one, two or three substituents selected from halo, phenyl, oxo, CN, NO₂, hydroxy, C₁–C₆-alkyl, C₁–C₆-alkyl substituted with C₃–C7-cycloalkyl, C₁–C₆-alkoxyl, NH₂, NHC₁–C₆-alkyl, N(C₁–C₆-alkyl)₂, (C=O)(C₁–C₆-alkyl), (C=O)O(C₁–C₆-alkyl), (C=O)OCH₂phenyl, (C=O)NH(C₁–C₆-alkyl), (C=O)N(C₁–C₆-alkyl)₂, NH(C=O)(C₁–C₆-alkyl),
q) NHCHO,
r) NH(C=O)(C₁–C₆-alkyl),
s) NH(C=O)(OC₁–C₆-alkyl),
t) aryl, wherein aryl is as defined above in o,
u) C₁–C₆-alkyl, wherein alkyl is unsubstituted or substituted with hydroxy, C₃–C₇-cycloalkyl, aryl or heterocyclyl, wherein aryl is defined as above and heterocyclyl is as defined below,
v) heterocyclyl, wherein heterocyclyl is as defined above in p,
w) when two of X', Y' and Z' are on adjacent carbons they can join to form a methylenedioxy bridge,
x) NH(C=O)aryl,
y) —NR¹⁴NHR¹⁵,
z) —S(O)xC₁–C₆-alkyl,
aa) SO₂NH C₁–C₆-alkyl, or
ab) CO₂H;

R¹⁴ and R¹⁵ are independently: H, C₁–C₆-alkyl, aryl or C₁–C₆-alkylaryl; or x is 0, 1 or 2.

An embodiment of the invention is the compound of Formula Ia

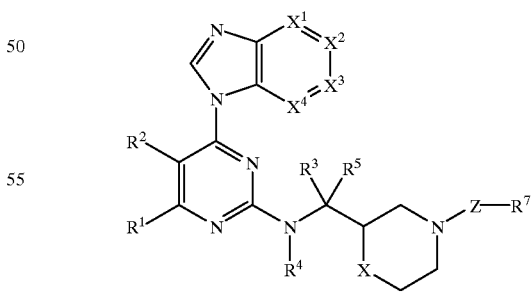

or pharmaceutically acceptable salts, hydrates, solvates, crystal forms and individual diastereomers thereof, wherein R¹ and R² are independently:
a) H,
b) halo( Br, Cl, I, or F),
c) OH, d) SH,
e) CN,
f) NO$_2$,
g) R$^9$,
h) OR$^9$,
i) O(C=O)R$^9$,
j) O(C=O)OR$^9$,
k) O(C=O)NHR$^9$,
l) O(C=O)NR$^9$R$^{10}$,
m) SR$^9$,
n) S(O)R$^9$,
o) S(O)$_2$R$^9$,
p) C(=O)R$^9$,
q) C(=O)OR$^9$,
r) C(=O)NHR$^9$,
s) C(=O)NR$^9$R$^{10}$,
t) NH$_2$,
u) NHR$^9$,
v) NR$^9$R$^{10}$,
w) NHC(=O)R$^9$,
x) NHC(=O)OR$^9$,
y) NR$^9$C(=O)R$^{10}$,
z) NR$^9$C(=O)NHR$^{10}$,
aa) NR$^9$C(=O)NR$^{10}$R$^{11}$,
ab) SO$_2$NHR$^9$,
ac) SO$_2$NR$^9$R$^{10}$,
ad) NHSO$_2$R$^9$,
ae) NR$^9$SO$_2$R$^{10}$, or
af) R$^1$ and R$^2$ can join together to form a fused methylenedioxy ring or a fused 6-membered aromatic ring;

R$^3$ and R$^5$ are independently:
a) H,
b) C$_1$–C$_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) R$^3$ and R$^5$ taken together can represent =O;

R$^4$ is:
a) H, or
b) C$_1$–C$_6$-alkyl, or
c) C$_1$–C$_6$-alkoxyl;

—X$^{12}$—X$^2$—X$^3$—X$^4$— is:
a) —CR$^6$=CR$^6$—CR$^{6a}$=CR$^6$,
b) —CR$^{6a}$=CR$^6$—CR$^6$=CR$^6$,
c) —N=CR$^6$—CR$^6$=CR$^6$—,
d) —CR$^6$=N—CR$^6$=CR$^6$—,
e) —CR$^6$=CR$^6$—N=CR$^6$—,
f) —CR$^6$=CR$^6$—CR$^6$=N—,
g) —N=CR$^6$—N=CR$^6$—,
h) —CR$^6$=N—CR$^6$=N—,
i) —CR$^6$=N—N=CR$^6$—, or
j) —N=CR$^6$—CR$^6$=N—;

R$^6$ and R$^{6a}$ are independently:
a) H,
b) halo( Br, Cl, I, or F),
c) OH,
d) SH,
e) CN,
f) NO$_2$,
g) N$_3$,
h) N$_2$+BF$_4$–,
i) R$^9$,
j) OR$^9$,
k) O(C=O)R$^9$,
l) O(C=O)OR$^9$,
m) O(C=O)NHR$^9$,
n) O(C=O)NR$^9$R$^{10}$,
o) SR$^9$,
p) S(O)R$^9$,
q) S(O)$_2$R$^9$,
r) C$_1$–C$_6$-alkyl, unsubstituted or substituted with one, two, or three substituents selected from R$^9$, R$^{10}$, and R$^{11}$,
s) C(=O)R$^9$,
t) C(=O)OR$^9$,
u) C(=O)NHR$^9$,
v) C(=O)NR$^9$R$^{10}$,
w) C(=O)N(OR$^9$)R$^{10}$,
x) NH$_2$,
y) NHR$^9$,
z) NHC$_1$–C$_6$-alkyl, unsubstituted or substituted with one, two, or three substituents selected from R$^9$, R$^{10}$, and R$^{11}$,
aa) NR$^9$R$^{10}$,
ab) NHC(=O)R$^9$,
ac) NR$^9$C(=O)R$^{10}$,
ad) NHC(=O)NHR$^9$,
ae) NR$^9$C(=O)NHR$^{10}$,
af) NR$^9$C(=O)NR$^{10}$R$^{11}$,
ag) SO$_2$NH$_2$,
ah) SO$_2$NHR$^9$,
ai) SO$_2$NR$^9$R$^{10}$,
aj) NHSO$_2$R$^9$,
ak) NR$^9$SO$_2$R$^{10}$, or
al) NHP(=O)(OC$_1$–C$_6$-alkyl)$_2$,
am) R$^6$ and R$^{6a}$ when on adjacent carbons can be joined to form a 5- or 6-membered ring having the following bridging atoms, when read from right to left, or left to right:
i) —CH=CH—CH=CH—,
ii) —OCH$_2$O—,
iii) —C(O)N(R$^9$)C(O)—,
iv) —CH$_2$N(R$^9$)CH$_2$—,
v) —N=CHNHC(O)—,
vi) —C(O)NHCH=N—,
vii) —C(O)OC(O)—,
viii) —NHC(O)NHC(O)—,
ix) —C(O)NHC(O)NH—,
x) —N=CHNH—, xi) —N=CHNR$^9$—, or
xii)

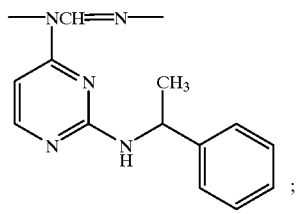

R$^7$ is:
  a) R$^9$,
  b) OR$^9$,
  c) NH$_2$,
  d) NHR$^9$, or
  e) NR$^9$R$^{10}$;
X is O, S, SO, SO$_2$, NR$^8$;
Z is C=O, SO$_2$, P(=O)(OR$^9$) or a single bond;
R$^8$ is:
  a) H,
  b) R$^9$,
  c) SO$_2$R$^9$,
  d) C(=O)R$^9$,
  e) C(=O)OR$^9$,
  f) C(=O)NR$^9$,
  f) C(=O)NR$^9$R$^{10}$;
R$^9$, R$^{10}$ and R$^{11}$ are independently:
  a) C$_1$–C$_6$-perfluoroalkyl,
  b) C$_1$–C$_6$-alkyl, unsubstituted or substituted with one, two, or three substituents selected from oxo, X', Y' and Z',
  c) C$_2$–C$_6$-alkenyl, unsubstituted or substituted with one, two, or three substituents selected from oxo, X', Y' and Z',
  d) C$_2$–C$_6$-alkynyl, unsubstituted or substituted with one, two, or three substituents selected from oxo, X', Y' and Z',
  e) aryl, wherein aryl is defined as phenyl or naphthyl, unsubstituted or substituted with one, two, or three substituents selected from X', Y' and Z', or
  f) heterocyclyl, wherein the heterocyclyl is unsubstituted or substituted with one, two or three substituents selected from oxo, X', Y', and Z', or
  g) C$_3$–C$_6$-cycloalkyl, unsubstituted or substituted with one, two, or three substituents selected from oxo, X', Y' and Z'; and
X', Y' and Z' independently are selected from:
  a) H,
  b) halo,
  c) CN,
  d) NO$_2$,
  e) hydroxy,
  f) C$_1$–C$_6$-perfluoroalkyl,
  g) C$_1$–C$_6$-alkoxyl, unsubstituted or substituted with aryl, wherein aryl is defined as phenyl or naphthyl,
  h) (C=O)(C$_1$–C$_6$-alkyl), unsubstituted or substituted with aryl, wherein aryl is defined as phenyl or naphthyl,
  i) (C=O)O(C$_1$–C$_6$-alkyl), unsubstituted or substituted with aryl, wherein aryl is defined as phenyl or naphthyl,
  j) (C=O)NH(C$_1$–C$_6$-alkyl),
  k) (C=O)N(C$_1$–C$_6$-alkyl)$_2$,
  l) NH$_2$,
  m) NHC$_1$–C$_6$-alkyl,
  n) N(C$_1$–C$_6$-alkyl)$_2$,
  o) NHaryl, wherein aryl is defined as phenyl or naphthyl, unsubstituted or substituted with one, two, or three substituents selected from halo, phenyl, CN, NO$_2$, hydroxy, C$_1$–C$_6$-alkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O(C$_1$–C$_6$-alkyl), (C=O)NH(C$_1$–C$_6$-alkyl), (C=O)N(C$_1$–C$_6$-alkyl)$_2$, and NH(C=O)(C$_1$–C$_6$-alkyl),
  p) NHheterocyclyl, wherein heterocyclyl is unsubstituted or substituted with one, two or three substituents selected from halo, phenyl, oxo, CN, NO$_2$, hydroxy, C$_1$–C$_6$-alkyl, C$_1$–C$_6$-alkoxyl, NH$_2$, NHC$_1$–C$_6$-alkyl, N(C$_1$–C$_6$-alkyl)$_2$, (C=O)(C$_1$–C$_6$-alkyl), (C=O)O (C$_1$–C$_6$-alkyl), (C=O)OCH$_2$phenyl, (C=O)NH (C$_1$–C$_6$-alkyl), (C=O)N(C$_1$–C$_6$-alkyl)$_2$, and NH(C=O)(C$_1$–C$_6$-alkyl),
  q) NHCHO,
  r) NH(C=O)(C$_1$–C$_6$-alkyl),
  s) NH(C=O)(OC$_1$–C$_6$-alkyl),
  t) aryl, wherein aryl is as defined above in o,
  u) C$_1$–C$_6$-alkyl, wherein alkyl is unsubstituted or substituted with aryl or heterocyclyl, wherein aryl is defined as above and heterocyclyl is as defined below,
  v) heterocyclyl, wherein heterocyclyl is as defined above in p, or
  w) when two of X', Y' and Z' are on adjacent carbons they can join to form a methylenedioxy bridge.

Preferred compounds of the present invention include the compounds of formula Ib:

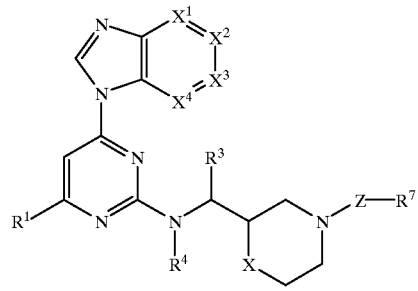

wherein R$^1$, R$^3$, and Z are as defined below and all other substituents are as defined above; or pharmaceutically acceptable salts, solvates, hydrates, crystal forms and individual diastereomers thereof, wherein
R$^1$ is:
  a) H,
  b) R$^9$,
  c) NH$_2$,
  d) NHR$^9$, or
  e) NR$^9$R$^{10}$;
R$^3$ is:
  a) H, or
  b) C$_1$–C$_6$-alkyl, unsubstituted or substituted with one, two, or three substituents selected from oxo, X', Y' and Z';
X is O or NR$^8$; and Z is C=O, SO$_2$, or a single bond.

Preferred compounds of the present invention include the compounds of Formula Ib:

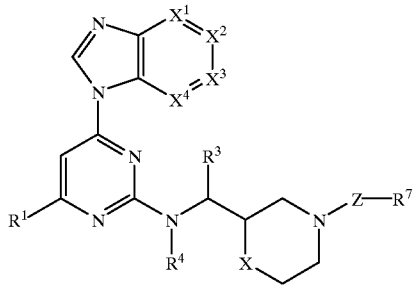

wherein —X$^1$—X$^2$—X$^3$—X$^4$—, R$^6$ and R$^{6a}$ are as defined below and all other substituents are as defined above; or pharmaceutically acceptable salts, hydrates, solvates, crystal forms and individual diastereomers thereof, wherein —X$^1$—X$^2$—X$^3$—X$^4$— is:

a) —CR$^6$=CR$^6$CR$^{6a}$=CR$^6$,
b) —CR$^{6a}$=CR$^6$CR$^6$=CR$^6$,
c) —N=CR$^6$—CR$^6$=CR$^6$—, or
d) —CR$^6$=N—CR$^6$=CR$^6$—; and R$^6$ and R$^{6a}$ are independently:

a) H,
b) haloy (Br, Cl, I, or F),
c) R$^9$,
d) OR$^9$,
e) C$_1$–C$_6$-alkyl, unsubstituted or substituted with one, two, or three substituents selected from R$^9$, R$^{10}$, and R$^{11}$,
f) NH$_2$,
g) NHR$^9$,
h) NHC$_1$–C$_6$-alkyl, unsubstituted or substituted with one, two, or three substituents selected from R$^9$, R$^{10}$, and R$^{11}$,
i) NR$^9$R$^{10}$,
j) NHC(=O)R$^9$,
k) NR$^9$C(=O)R$^{10}$,
l) NR$^9$C(=O)NHR$^{10}$,
m) NR$^9$C(=O)NR$^{10}$R$^{11}$,
n) NHSO$_2$R$^9$,
o) NR$^9$SO$_2$R$^{10}$, or
p) R$^6$ and R$^{6a}$ when on adjacent carbons can be joined to form a 5- or 6-membered ring having the following bridging atoms, when read from right to left, or left to right:
  i) —N=CHNH—,
  ii) —N=CHNR$^9$—, or iii)

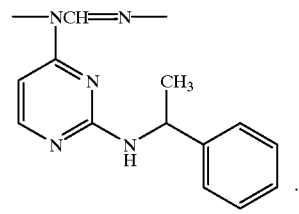

More preferred compounds of the present invention include the compounds of Formula Ib:

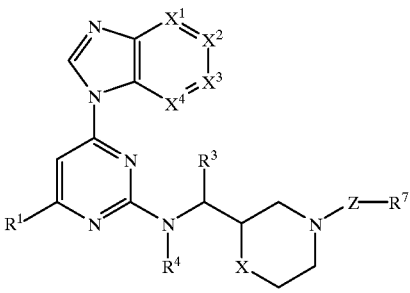

wherein —X$^1$—X$^2$—X$^3$—X$^4$—, R$^6$, R$^{6a}$, R$^7$, and R$^8$ are as defined herein and all other substituents are as defined above; or pharmaceutically acceptable salts, hydrates, solvates, crystal forms and individual diastereomers thereof, wherein —X$^1$—X$^2$—X$^3$—X$^4$— is:

a) —CH=CR$^6$—CR$^{6a}$=CH—, or
b) —CR$^{6a}$=CR$^6$—CH=CH—;

R$^6$ and R$^{6a}$ are as defined below such that one and only one of R$^6$ and R$^{6a}$ is other than H, except when R$^6$ and R$^{6a}$ are as defined in (p):

a) H,
b) halo( Br, Cl, I, or F),
c) R$^9$,
d) OR$^9$,
e) C$_1$–C$_6$-alkyl, unsubstituted or substituted with one, two, or three substituents selected from R$^9$, R$^{10}$, and R$^{11}$,
f) NH$_2$,
g) NHR$^9$,
h) NHC$_1$–C$_6$-alkyl, unsubstituted or substituted with one, two, or three substituents selected from R$^9$, R$^{10}$, and R$^{11}$,
i) NR$^9$R$^{10}$,
j) NHC(=O)R$^9$,
k) NR$^9$C(=O)R$^{10}$,
l) NR$^9$C(=O)NHR$^{10}$,
m) NR$^9$C(=O)NR$^{10}$R$^{11}$,
n) NHSO$_2$R$^9$,
o) NR$^9$SO$_2$R$^{10}$, or
p) R$^6$ and R$^{6a}$ when on adjacent carbons can be joined to form a 5- or 6-membered ring having the following bridging atoms, when read from right to left, or left to right:

i) —N=CHNH—,
ii) —N=CHNR⁹—, or
iii)

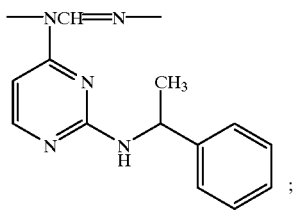

R⁷ is:
  a) R⁹,
  b) OR⁹,
  c) NH₂,
  d) NHR⁹, or
  e) NR⁹R¹¹; and
R⁸ is H, or R⁹.

More preferred compounds of the present invention include the compounds of Formula Ic:

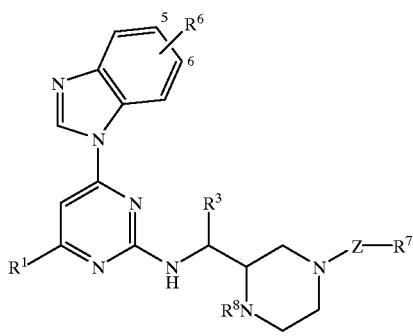

wherein R¹, R³, R⁶ (attached at the 5- or 6-position of the benzimidazole), R⁸, and Z are as defined herein and all other substituents are as defined above; or pharmaceutically acceptable salts, hydrates, solvates, crystal forms and individual diastereomers thereof, wherein
R¹ is:
  a) H, or
  b) R⁹;
R³ is:
  a) H, or
  b) C₁–C₆-alkyl;
R⁶ is:
  a) H,
  b) halo( Br, Cl, I, or F),
  c) R⁹,
  d) OR⁹,
  e) C₁–C₆-alkyl, unsubstituted or substituted with one, two, or three substituents selected from R⁹, R¹⁰, and R¹¹,
  f) NH₂,
  g) NHR⁹,
  h) NHC₁–C₆-alkyl, unsubstituted or substituted with one, two, or three substituents selected from R⁹, R¹⁰, and R¹¹,
  i) NR⁹R¹⁰,
  j) NHC(=O)R⁹,
  k) NR⁹C(=O)R¹⁰,
  l) NR⁹C(=O)NHR¹⁰,
  m) NR⁹C(=O)NR¹⁰R¹¹,
  n) NHSO₂R⁹, or
  o) NR⁹SO₂R¹⁰;
z) is C=O, SO₂, or a single bond; and
R⁸ is:
  a) H, or
  b) R⁹.

More preferred compounds of the present invention include the compounds of Formula Id:

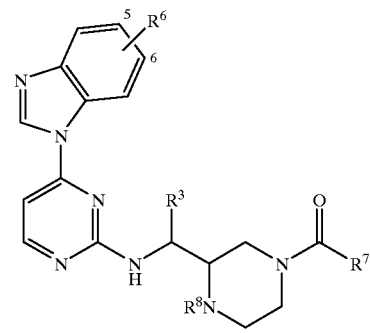

wherein R⁶ (attached at the 5- or 6-position of the benzimidazole) and R⁷ are as defined herein and all other substituents are as defined above; or pharmaceutically acceptable salts, hydrates, solvates, crystal forms and individual diastereomers thereof, wherein
R⁶ is:
  a) H,
  b) halo( Br, Cl, I, or F),
  c) R⁹,
  d) OR⁹,
  e) C₁–C₆-alkyl, unsubstituted or substituted with one, two, or three substituents selected from R⁹, R¹⁰, and R¹¹,
  f) NH₂,
  g) NHR⁹,
  h) NHC₁–C₆-alkyl, unsubstituted or substituted with one, two, or three substituents selected from R⁹, R¹⁰, and R¹¹,
  i) NR⁹R¹⁰,
  j) NHC(=O)R⁹,
  k) NR⁹C(=O)R¹⁰,
  l) NR⁹C(=O)NHR¹⁰,
  m) NR⁹C(=O)NR¹⁰R¹¹,
  n) NHSO₂R⁹, or
  o) NR⁹SO₂R¹⁰; and
R⁷ is:
  a) R⁹,
  d) NHR⁹, or
  e) NR⁹R¹⁰.

More preferred compounds of the present invention include the compounds of Formula Ie:

17

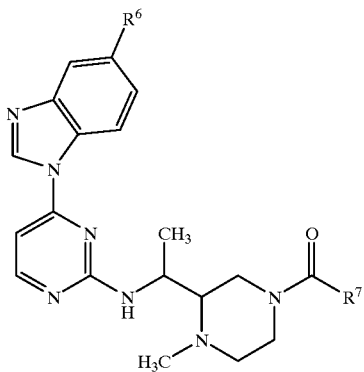

wherein $R^6$ and $R^7$ are as defined herein and all other substituents are as defined above; or pharmaceutically acceptable salts, hydrates, solvates, crystal forms and individual diastereomers thereof, wherein
$R^6$ is:
a) H,
b) halo( Br, Cl, I, or F),
c) $R^9$,
d) $OR^9$,
e) $C_1$–$C_6$-alkyl, unsubstituted or substituted with one, two, or three substituents selected from $R^9$, $R^0$, and $R^{11}$,
f) $NH_2$,
g) $NHR^9$,
h) $NHC_1$–$C_6$-alkyl, unsubstituted or substituted with one, two, or three substituents selected from $R^9$, $R^{10}$, and $R^{11}$,
i) $NR^9R^{10}$,
j) $NHC(=O)R^9$,
k) $NR^9C(=O)R^{10}$,
l) $NR^9C(=O)NHR^{10}$,
m) $NR^9C(=O)NR^{10}R^{11}$,
n) $NHSO_2R^9$, or
o) $NR^9SO_2R^{10}$; and
$R^7$ is $NHR^9$.

More preferred compounds of the present invention include the compounds of Formula Ie:

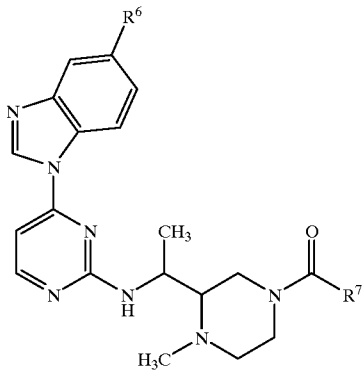

wherein $R^6$ and $R^7$ are as defined herein and all other substituents are as defined above; or pharmaceutically acceptable salts, hydrates, solvates, crystal forms and individual diastereomers thereof, wherein

18

$R^6$ is:
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) $NH_2$,
j) $NHR^9$,
k) $NHC_1$–$C_6$-alkyl, unsubstituted or substituted with one, two, or three substituents selected from $R^9$, $R^{10}$, and $R^{11}$,
l) $NR^9R^{10}$,
m) $NHC(=O)R^9$,
n) $NR^9C(=O)R^{10}$,
m) $NR^9C(=O)NHR^{10}$,
p) $NR^9C(=O)NR^{10}R^{11}$,
q) $NHSO_2R^9$, or
r) $NR^9SO_2R^{10}$; and
$R^7$ is: NHaryl, wherein aryl is defined as phenyl or naphthyl, unsubstituted or substituted with one, two, or three substituents selected from X', Y' and Z'.

More preferred compounds of the present invention include the compounds of Formula Ie:

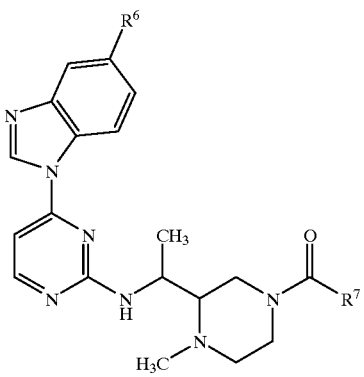

wherein $R^6$ and $R^7$ are as defined herein and all other substituents are as defined above; or pharmaceutically acceptable salts, hydrates, solvates, crystal forms and individual diastereomers thereof, wherein
$R^6$ is:
a) phenyl, unsubstituted or substituted with one, two, or three substituents selected from X', Y' and Z',
b) pyridyl, unsubstituted or substituted with one, two or three substituents selected from X', Y', and Z',
c) pyridazinyl, unsubstituted or substituted with one, two or three substituents selected from X', Y', and Z',
d) pyrimidinyl, unsubstituted or substituted with one, two or three substituents selected from X', Y', and Z',
e) imidazolidinyl, unsubstituted or substituted with one, two or three substituents selected from oxo, X', Y', and Z', f) 1,3-diazobicyclo[3.3.0]octan-2-onyl, or g) 1,3-diazobicyclo[4.3.0]nonan-2-onyl; and R⁷ is NHR⁹.

More preferred compounds of the present invention include the compounds of Formula Ie:

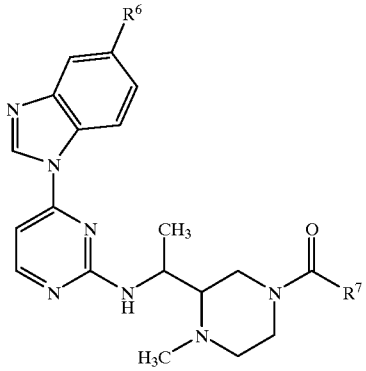

wherein R⁶ and R⁷ are as defined herein and all other substituents are as defined above; or pharmaceutically acceptable salts, hydrates, solvates, crystal forms and individual diastereomers thereof, wherein R⁶ is:
  a) phenyl, unsubstituted or substituted with one, two, or three substituents selected from X', Y' and Z',
  b) pyridyl, unsubstituted or substituted with one, two or three substituents selected from X', Y', and Z',
  c) pyridazinyl, unsubstituted or substituted with one, two or three substituents selected from X', Y', and Z',
  d) pyrimidinyl, unsubstituted or substituted with one, two or three substituents selected from X', Y', and Z',
  e) imidazolidinyl, unsubstituted or substituted with one, two or three substituents selected from oxo, X', Y', and Z',
  f) 1,3-diazobicyclo[3.3.0]octan-2-onyl, or
  g) 1,3-diazobicyclo[4.3.0]nonan-2-onyl; and R⁷ is: NHaryl, wherein aryl is defined as phenyl or naphthyl, unsubstituted or substituted with one, two, or three substituents selected from X', Y' and Z'.

More preferred compounds of the present invention include the compounds of Formula If:

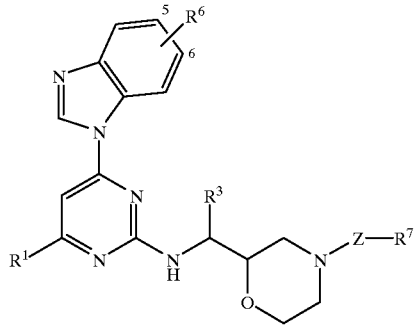

wherein R¹, R³, R⁶ (attached at the 5- or 6-position of the benzimidazole), R⁷, and Z are as defined herein and all other substituents are as defined above; or pharmaceutically acceptable salts, hydrates, solvates, crystal forms and individual diastereomers thereof, wherein R¹ is:
  a) H, or
  b) R⁹;

R³ is:
  a) H, or
  b) C₁–C₆-alkyl;

R⁶ is:
  a) H,
  b) halo( Br, Cl, I, or F),
  c) R⁹,
  d) OR⁹,
  e) C₁–C₆-alkyl, unsubstituted or substituted with one, two, or three substituents selected from R⁹, R¹⁰, and R¹¹,
  f) NH₂,
  g) NHR⁹,
  h) NHC₁–C₆-alkyl, unsubstituted or substituted with one, two, or three substituents selected from R⁹, R¹⁰, and R¹¹,
  i) NR⁹R¹⁰,
  j) NHC(=O)R⁹,
  k) NR⁹C(=O)R¹⁰,
  l) NR⁹C(=O)NHR¹⁰,
  m) NR⁹C(=O)NR¹⁰R¹¹,
  n) NHSO₂R⁹, or
  o) NR⁹SO₂R¹⁰;

R⁷ is:
  a) R⁹,
  b) OR⁹,
  c) NH₂,
  d) NHR⁹, or
  e) NR⁹R¹⁰; and

Z is C=O, SO₂, or a single bond.

More preferred compounds of the present invention include the compounds of Formula Ig:

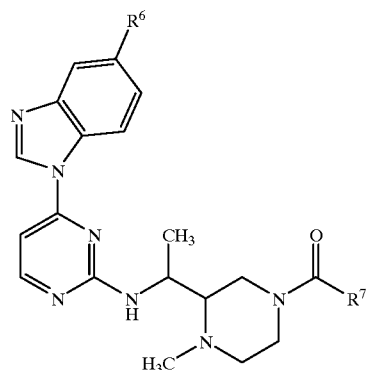

wherein R⁶ and R⁷ are as defined herein and all other substituents are as defined above; or pharmaceutically acceptable salts, hydrates, solvates, crystal forms and individual diastereomers thereof, wherein R⁶ is:
  a) H,
  b) phenyl, unsubstituted or substituted with one, two, or three substituents selected from X', Y' and Z',
  c) pyridyl, unsubstituted or substituted with one, two or three substituents selected from X', Y', and Z', d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) $NH_2$,
j) $NHR^9$,
k) $NHC_1-C_6$-alkyl, unsubstituted or substituted with one, two, or three substituents selected from $R^9$, $R^{10}$, and $R^{11}$,
l) $NR^9R^{10}$,
m) $NHC(=O)R^9$,
n) $NR^9C(=O)R^{10}$,
o) $NR^9C(=O)NHR^{10}$,
p) $NR^9C(=O)NR^{10}R^{11}$,
q) $NHSO_2R^9$, or
r) $NR^9SO_2R^{10}$; and $R^7$ is: NHaryl, wherein aryl is defined as phenyl or naphthyl, unsubstituted or substituted with one, two, or three substituents selected from X', Y' and Z'.

More preferred compounds of the present invention include the compounds of Formula Ig:

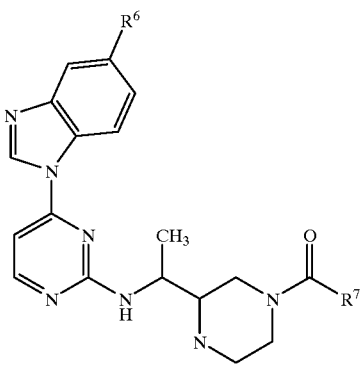

wherein $R^6$ and $R^7$ are as defined herein and all other substituents are as defined above; or pharmaceutically acceptable salts, hydrates, solvates, crystal forms and individual diastereomers thereof, wherein
$R^6$ is:
  a) phenyl, unsubstituted or substituted with one, two, or three substituents selected from X', Y' and Z',
  b) pyridyl, unsubstituted or substituted with one, two or three substituents selected from X', Y', and Z',
  c) pyridazinyl, unsubstituted or substituted with one, two or three substituents selected from X', Y', and Z',
  d) pyrimidinyl, unsubstituted or substituted with one, two or three substituents selected from X', Y', and Z',
  e) imidazolidinyl, unsubstituted or substituted with one, two or three substituents selected from oxo, X', Y', and Z',
  f) 1,3-diazobicyclo[3.3.0]octan-2-onyl, or
  g) 1,3-diazobicyclo[4.3.0]nonan-2-onyl; and
$R^7$ is $NHR^9$.

More preferred compounds of the present invention include the compounds of Formula Ig:

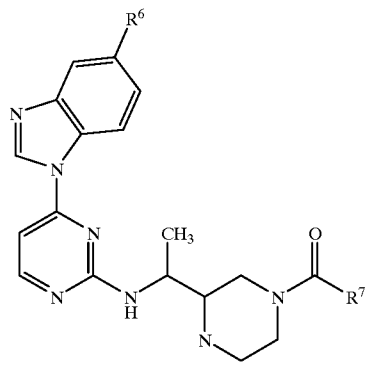

wherein $R^6$ and $R^7$ are as defined herein and all other substituents are as defined above; or pharmaceutically acceptable salts, hydrates, solvates, crystal forms and individual diastereomers thereof, wherein
$R^6$ is:
  a) phenyl, unsubstituted or substituted with one, two, or three substituents selected from X', Y' and Z',
  b) pyridyl, unsubstituted or substituted with one, two or three substituents selected from X', Y', and Z',
  c) pyridazinyl, unsubstituted or substituted with one, two or three substituents selected from X', Y', and Z',
  d) pyrimidinyl, unsubstituted or substituted with one, two or three substituents selected from X', Y', and Z',
  e) imidazolidinyl, unsubstituted or substituted with one, two or three substituents selected from oxo, X', Y', and Z',
  f) 1,3-diazobicyclo[3.3.0]octan-2-onyl, or
  g) 1,3-diazobicyclo[4.3.0]nonan-2-onyl; and
$R^7$ is: NHaryl, wherein aryl is defined as phenyl or naphthyl, unsubstituted or substituted with one, two, or three substituents selected from X', Y' and Z'.

An embodiment of the invention includes the compound of Formula Ih:

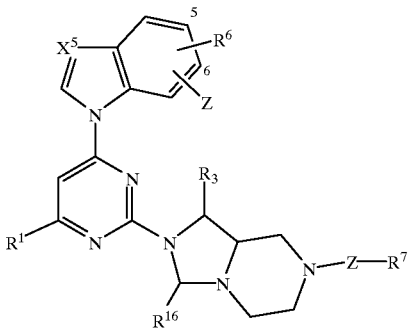

wherein $R^1$, $R^3$ $R^6$ (attached at the 5- or 6-position), $R^7$, $R^{16}$ and Z are as defined herein and all other substituents are as defined above; or pharmaceutically acceptable salts, hydrates, solvates, crystal forms and individual diastereomers thereof, wherein
$R^1$ is:
  a) H, or
  b) $R^9$;
$R^3$ is:
  a) H, or
  b) $C_1-C_6$-alkyl;

$R^6$ is:
- a) H,
- b) halo(Br, Cl, I, or F),
- c) $R^9$,
- d) $OR^9$,
- e) $C_1$–$C_6$-alkyl, unsubstituted or substituted with one, two, or three substituents selected from $R^9$, $R^{10}$, and $R^{11}$,
- f) $NH_2$,
- g) $NHR^9$,
- h) $NHC_1$–$C_6$-alkyl, unsubstituted or substituted with one, two, or three substituents selected from $R^9$, $R^{10}$, and $R^{11}$,
- i) $NR^9R^{10}$,
- j) $NHC(=O)R^9$,
- k) $NR^9C(=O)R^{10}$,
- l) $NR^9C(=O)NHR^{10}$,
- m) $NR^9C(=O)NR^{10}R^{11}$,
- n) $NHSO_2R^9$, or
- o) $NR^9SO_2R^{10}$;

Z is C=O, $SO_2$, or a single bond; and
$R^7$ is:
- a) $R^9$,
- d) $NHR^9$, or
- e) $NR^9R^{10}$; and $R^{16}$ is:
- a) H,
- b) phenyl,
- c) benzyl, or
- d) pyridyl.

More preferred compounds of the present invention include the compounds of Formula I, or its pharmaceutically acceptable salt, hydrate, solvate, crystal form and individual diastereomer thereof is selected from the group consisting of:

2-[(1-(benzyloxycarbonyl)morpholin-2-yl)methylamino]-4-[benzimidazol-1-yl]pyrimidine,
2-[(1-(N-phenylcarbamoyl)morpholin-2-yl)methylamino]-4-[benzimidazol-1-yl]pyrimidine,
2-[(1-(N-naphth-1-ylcarbamoyl)morpholin-2-yl)-methylamino]-4-[benzimidazol-1-yl]pyrimidine,
2-[(1-methanesulfonylmorpholin-2-yl)methylamino]-4-[benzimidazol-1-yl]pyrimidine,
2-[(1-(benzyloxycarbonyl)-4-(tert-butyloxycarbonyl)piperazin-2-yl)methylamino]-4-[benzimidazol-1-yl]pyrimidine,
2-[(4-(N-naphth-1-ylcarbamoyl)piperazin-2-yl)methylamino]-4-[benzimidazol-1-yl]pyrimidine,
2-[(1-methyl-4-(N-naphth-1-ylcarbamoyl)piperazin-2-yl)methylamino]-4-[benzimidazol-1-yl]pyrimidine,
2-[1-(4-(N-naphth-1-ylcarbamoyl)morpholin-2-yl)ethylaminol-4-[benzimidazol-1-yl]pyrimidine,
2-[1-(1-methyl-4-(N-naphth-1-ylcarbamoyl)piperazin-2-yl)ethylamino]-4-[benzimidazol-1-yl]pyrimidine,
2-[1-(1-methanesulfonyl-4-(N-naphth-1-ylcarbamoyl)piperazin-2-yl)ethylamino]-4-[benzimidazol-1-yl]pyrimidine,
2-[1-(1-methyl-4-(N-naphth-1-ylcarbamoyl)piperazin-2-yl)ethylamino]-4-[5-(2-aminopyridin-4-yl)benzimidazol-1-yl]pyrimidine,
2-[1-(1-methyl-4-(N-naphth-1-ylcarbamoyl)piperazin-2-yl)ethylamino]-4-[5-(2-aminopynimidin-4-yl)benzimidazol-1-yl]pyrimidine,
2-[-(1-methyl-4-(N-naphth-1-ylcarbamoyl)piperazin-2-yl)ethylamino]-4-[5-(pyridin-4-yl)benzimidazol-1-yl]pyrimidine,
2-[1-(1-methyl-4-(N-naphth-1-ylcarbamoyl)piperazin-2-yl)ethylamino]-4-[5-5 (pyridazin-3-yl)benzimidazol-1-yl]pyrimidine, 2-[1-(1-methyl-4-(N-naphth-1-ylcarbamoyl)piperazin-2-yl)ethylamino]-4-[5-(3-N,N-dimethylpyridazin-6-yl)benzimidazol-1-yl]pyrimidine,
2-[1-(1-methyl-4-(N-naphth-1-ylcarbamoyl)piperazin-2-yl)ethylamino]-4-[5-(2-aminopyrimidin-4-yl)benzimidazol-1-yl]-6-[2-methylphenyl]pyrimidine,
2-[1-(1-methyl-4-(N-naphth-1-ylcarbamoyl)piperazin-2-yl)ethylamino]-4-[5-(2-aminopyrimidin-4-yl)benzimidazol-1-yl]-6-[2-hydroxymethylphenyl]pyrimidine,
2-[1-(1-methyl-4-(N-phenylcarbamoyl)piperazin-2-yl)ethylamino]-4-[5-(2-aminopyridin-4-yl)benzimidazol-1-yl]pyrimidine,
2-[1-(1-methyl-4-(N-phenylcarbamoyl)piperazin-2-yl)ethylamino]-4-[5-(2-aminopyrimidin-4-yl)benzimidazo]-1-yl]pyrimidine,
2-[1-(-methyl-4-(N-phenylcarbamoyl)piperazin-2-yl)ethylamino]-4-[5-(pyridin-4-yl)benzimidazol-1-yl]pyrimidine,
2-[1-(-methyl-4-(N-phenylcarbamoy)piperazin-2-yl)ethylamino]-4-[5-(pyridazin-3-yl)benzimidazol-1-yl]pyrimidine,
2-[1-(1-methyl-4-(N-phenyicarbamoyi)piperazin-2-yl)ethylamino]-4-[5-(3-N,N-dimethylpyridazin-6-yl)benzimidazol-1-yl]pyrimidine,
2-[1-(1-methyl-4-(N-phenylcarbamoyl)piperazin-2-yl)ethylamino]-4-[5-(2-aminopyrimidin-4-yl)benzimidazol-1-yl]-6-[2-methylphenyl]pyrimidine; and
2-[1-(1-methyl-4-(N-phenylcarbamoyl)piperazin-2-yl)ethylamino]-4-[5-(2-aminopyrimidin-4-yl)benzimidazol-1-yl]-6-[2-hydroxymethylphenyl]pyrimidine.

The preferred compounds of the present invention include the compounds of Formula I, or pharmaceutically acceptable salts, hydrates, solvates, crystal forms and individual diastereomers thereof, wherein $R^1$ and $R^2$ independently are: H, $R^9$, $NH_2$, $NHR^9$, or $NR^9R^{10}$; and most preferably when $R^2$ is H and $R^1$ is: H, $R^9$, $NH_2$, $NHR^9$, or $NR^9R^{10}$.

The preferred compounds of the present invention include the compounds of Formula I, or pharmaceutically acceptable salts, hydrates, solvates, crystal forms and individual diastereomers thereof, wherein —$X^1$—$X^2$—$X^3$—$X^4$— is: —$CR^6$=$CR^6$—$CR^{6a}$=$CR^6$—, —$CR^{6a}$=$CR^6$—$CR^6$—$CR^6$—, —$CR^6$=N—$CR^6$=$CR^6$—, or —$CR^6$=$CR^6$—N=$CR^6$—; and most preferably is —CH=$CR^6$—CH=CH—.

The preferred compounds of the present invention include the compounds of Formula I, or pharmaceutically acceptable salts, hydrates, solvates, crystal forms and individual diastereomers thereof, wherein X is: O or $NR^8$ and $R^8$ is: H, or $R^9$—; and most preferably $R^8$ is $CH_3$.

The preferred compounds of the present invention include the compounds of Formula I, or pharmaceutically acceptable salts, hydrates, solvates, crystal forms and individual diastereomers thereof, wherein Z is C=O, $SO_2$, or a single bond; and most preferably is C=O.

The preferred compounds of the present invention include the compounds of Formula I, or pharmaceutically acceptable salts, hydrates, solvates, crystal forms and individual diastereomers thereof, wherein $R^6$ and $R^{6a}$ are independently: H; halo(Br, Cl, I, or F); $R^9$; $OR^9$; $C_1$–$C_6$-alkyl, unsubstituted or substituted with one, two, or three substituents selected from $R^9$, $R^{10}$, and $R^{11}$; $NH_2$; $NHR^9$; $NHC_1$–$C_6$-alkyl, unsubstituted or substituted with one, two, or three substituents selected from $R^9$, $R^{10}$, and $R^{11}$; $NR^9R^{10}$; $NHC(=O)R^9$; $NR^9C(=O)R^{10}$; $NR^9C(=O)NHR10$; $NR^9C(=O)NR^{10}R^{11}$; $NHSO_2R^9$; $NR^9SO_2R^{10}$; or $R^6$ and $R^{6a}$ when on adjacent carbons can be joined to form a 5- or 6-membered ring having the following bridging atoms: —N=CHNH—, —NHCH=N—, —N=CHNR$^9$—, —NR$^9$CH=N—,

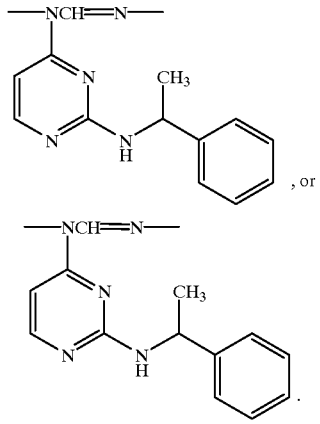

The preferred compounds of the present invention include the compounds of Formula I, or pharmaceutically acceptable salts, hydrates, solvates, crystal forms and individual diastereomers thereof, wherein $R^7$ is: $R^9$, $NHR^9$, or $NR^9R^{10}$—; and most preferably is $NHR^9$.

The independent syntheses of the diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-6}$, as in $C_{1-6}$alkyl is defined to identify the group as having 1, 2, 3, 4, 5, or 6 carbons in a linear or branched arrangement, such that $C_{1-6}$ alkyl specifically includes methyl, ethyl, propyl, butyl, pentyl, and hexyl. The term "heterocyclyl" as used herein is intended to include the following groups: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, imidazolidinyl, imidazolidonyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidinyl, purinyl, pteridinyl, phthalazinyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, benzopiperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzoyl, tetrahydrofuranyl, tetrahydrothienyl, 1,3-diazobicyclo[3.3.0]octan-2-onyl, 1,3-diazobicyclo[3.3.0]octanyl, 1,3-diazobicyclo[4.3.0]nonan-2-onyl and N-oxides thereof.

Utility

The compounds of Formula I of the present invention inhibit protein tyrosine kinases, especially Src-family kinases such as Lck, Fyn(T), Fyn(B), Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a preferred embodiment of the present invention. Compounds of the present invention which selectively block T cell activation and proliferation are preferred. Also, compounds of the present invention which may block the activation of endothelial cell protein tyrosine kinase by oxidative stress, thereby limiting surface expression of adhesion molecules that induce neutrophil binding, and which can inhibit protein tyrosine kinase necessary for neutrophil activation would be useful, for example, in the treatment of ischemia and reperfusion injury.

The present invention also provides methods for the treatment of protein tyrosine kinase-associated disorders, comprising the step of administering to a subject in need thereof at least one compound of the Formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of Formula I of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves'Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides for a method for treating the aforementioned disorders such as atopic dermatitis by administration of a therapeutically effective amount of a compound of Formula I of the present invention, which is an inhibitor of protein tyrosine kinase, to a patient in need of such treatment.

Src-family kinases other than Lck, such as Hck and Fgr, are important in the Fc gamma receptor induced respiratory burst of neutrophils as well as the Fc gamma receptor responses of monocytes and macrophages. The compounds of the present invention may inhibit the Fc gamma induced respiratory burst response in neutrophils, and may also inhibit the Fc gamma dependent production of TNF alpha. The ability to inhibit Fc gamma receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fc gamma receptor responses and which can lead to kidney damage.

In addition, certain Src family kinases, such as Lyn and Src, may be important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention may inhibit the Fc epsilon induced degranulation responses. The ability to inhibit Fc epsilon receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In a particular embodiment, the compounds of Formula I of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the Formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of cosinophils and/or lymphocytes are to be inhibited or promoted, in order to modulate the inflammatory response.

The subjects treated in the above methods, in whom which protein tyrosine kinase inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD 154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antuinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-oc inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following assays can be employed in ascertaining the degree of activity of a compound as a protein tyrosine kinase inhibitor. Compounds descibed herein have been tested in one or more of the assays, and have shown activity. Representative compounds of the invention were tested and found to exhibit $IC_{50}$ values of at least <10 $\mu$M in any one of the described assays, thereby demonstrating and confirming the utility of the compounds of the invention as protein tyrosine kinase inhibitors and in the prophylaxis and treatment of immune diseases, hyperproliferative disorders, etc.

Jacks Assay

This assays measures the ability of compounds to block intracellular ZAP-70 kinase activation after stimulation of Jurkat T cells with anti-T cell receptor antibodies.

Step 1: Preparation of Jurkat Cells

Wash confluent Jurkat cells 2 times in serum-free RPMI (Gibco). Resuspend cells at $1.1 \times 10^6$ cells/ml in serum free-RPMI, keep on ice.

Step 2: Dilute Compounds

Titer test compounds in DMSO, prepare 110× concentrated solutions.

Step 3: Prepare Anti Vb8 Stock

Dilute anti-Vb8 (Pharmingen) to 917 ng/ml in Tris buffered saline.

Step 4: Run Cell Assay

For each test compound, place 12 V-bottom polypropylene PCR tubes in a thermal cycler (MJ Research) set at 0° C. Run no more than 4 compounds at a time. Also run 2 samples which receive just RPMI instead of anti-Vb8. These controls should be harvested at time=0 and time=2.5 minutes. To test for nonspecific interference with the assay, run cells plus anti-Vb8 for each drug tested and later, after these cells are lysed, add 1 ml of the test compound dilutions. Add 100 ml of Jurkat cells to each tube. Add 1 ml of test compounds diluted in DMSO. Add 9 ml of anti-Vb8 and mix. Incubate 5 min at 0C. Add 2× Lysis Buffer to time=0 and no anti-Vb8 control. Set thermal cycler to 37° C. At time =2.5 minutes, add 110 ml of 2× Lysis Buffer to each well. Freeze samples in dry ice ethanol. They can be stored overnight at −80° C., or you can continue with the assay.

Step 4: Run ZAP-70 Kinase Assay

Thaw cell lysates. Prepare 2× Kinase Reaction Buffer. Mix lysates well and put duplicate 25 ml aliquots into black U bottom plates (Falcon). Add 25 ml of 2× kinase mix. Seal plate and incubate 30 min at 300. Add 50 ml 2× Quench solution. Leave plates in dark for 1 hour. Measure time-resolved fluorescent energy transfer in a Discovery plate reader (Packard).

Solutions:

| | |
|---|---|
| 2X Lysis Buffer | 300 mM NaCl, 100 mM Tris, pH 7.5, 20% glycerol, 2 mg/ml BSA, 2% NP40, 1 mM vanadate, 1x protease inhibitors, 0.05% $NaN_3$, protease inhibitor mixture (Boehringer Mannheim) |
| 2X Kinase Buffer | 100 mM MOPS pH 7, 10% glycerol, 20 mM $MgCl_2$, 1 mg/ml BSA, 0.01% $NaN_3$, 200 mM ATP, 4 mM biotin-conjugated peptide substrate (long chain biotin-Glu-Gln-Glu-Asp-Glu-Pro-Glu-Asp-Tyr-Phe-Glu-Trp-Leu-Glu-NH2) |
| 2X Quench Buffer | 50 mM HEPES, pH 7.25, 30 mM EDTA, 0.2 M KF, 1 mg/ml BSA, 0.1% triton X100, 0.01% $NaN_3$, 420 nM XL665-avidin (Cis Biotech), Europium cryptate (Cis Biotech)-conjugated PY20 antibody (Transduction Laboratories)-add enough europium cryptate conjugate to each well to give around 8000 B counts. |

IL2_Mart Assay

Step 1: IL2 Secretion From Antigen-stimulated T Cells

Mix 30,000 Jurkat-mart#22 T cells with 30,000 T2 antigen presenting cells in 100 $\mu$l of RPMI medium containing 10% fetal calf serum in 96 well flat-bottom tissue culture plates (Falcon). Add 1 $\mu$l of compound titered in DMSO. Add 99 $\mu$l of 1 $\mu$M of M9-2 peptide [Ala-Ala-Gly-Ile-Gly- Ile-Leu-Thr-Val]. Incubate overnight at 37° C. in a 5% $CO_2$ incubator. Collect culture supernatants.

Step 2: Measurement of IL2 in Culture Supernatant

Coat Immulon2 plates (Dynatech) with 50 μl anti-human IL-2 (R &D) at 4 μg/ml in PBS/0.05% azide. Incubate overnight at 4° C. Block wells for at least 1 hour at room temperature with Block Buffer: Tris buffered saline (TBS)/1% BSA/0.05% azide. Wash wells 3 times with Wash Buffer: TBS/0.01% Tween 20. Add 50 μl of culture supernatants, or IL2 standards, to the microtiter wells. Incubate 1 hour at room temperature. Wash plate 3 times with Wash Buffer. Add 75 μl of anti-human IL-2-Biotin (R&D) at 450 ng/ml in Block Buffer. Incubate 1 hour at room temperature. Wash wells 3 times with Wash Buffer. Add 100 μl of 1 μg/ml europium-conjugated streptavidin (Wallac). Incubate 20 minutes at room temperature. Wash plate 3 times with Wash Buffer. Add 150 μl Enhancement solution (Wallac) Incubate 30 at least minutes at room temperature. Measure time resolved europium fluorescence on a Victor2 plate reader (Wallac).

A General HTRF Tyrosine Kinase Assay Protocol
(96-Well, 50 μL Kinase/100 μL Total Assay Volume)

Materials

N-LCB-EQEDEPEGDYEEVLE-NH$_2$ (peptide substrate for Src family tyrosine kinases, Lck, Fyn(T), Fyn(B), Lyn, Src, BIk, Hck, Fgr, and Yes; LCB=aminohexanoylbiotin), N-LCB-EQEDEPEGIYGVLF-NH$_2$ (peptide substrate for ZAP-70, Syk, and Csk) were synthesized using an Applied Biosystem's 433A peptide synthesizer using FastMO™ chemistry. All the Src family (Lck, Fyn(T), Fyn(B), Lyn, Src, BIk, Hck, Fgr, and Yes) as well as ZAP-70, Syk and Csk tyrosine kinases were expressed and purified using standard techniques known in the art. Streptavidin-XL665 (Streptavidin labeled with crosslinked allophycocyanin) was purchased from CISbio (France). Eu(K)-PY20 (Anti-phosphotyrosine antibody, PY20, labeled with Europium Cryptate) was using procedures described in: "Use Of A Phosphotyrosine-Antibody pair As A General Detection Method In Homogeneous Time Resolved Fluorescence: Application To Human Immunodeficency Viral Protease" Cummings, R. T., McGovern, H. M., Zheng, S., Park, Y. W., and Hermes, J. D. Analytical Biochemistry, Vol 269, 79–93 (1999); and "Homogeneous Proximity Tyrosine Kinase Assays: Scintialition Proximity Assay Versus Homogeneous Time Resolved Fluorescence" Park, Y. W., Cummings, R. T., Wu, L., Zheng, S., Cameron, P. M., Woods, A., Zaller, D., Marcy, A. I., and Hermes, J. D. Analytical Biochemistry, Vol 269, 94–104 (1999). Anti-phosphotyrosine antibody PY20 and Europium Cryptate were purchased from Transduction Laboratories (Lexington, Ky.) and CISbio (France), respectively.

General Assay Protocol

Standard assay conditions were 50 μL kinase reaction consisting of 0.75 μM N-biotinyl peptide substrate and 10 μM ATP in assay buffer (50 mM Hepes, pH 7.0, 10 mM MgCl$_2$, 0.1% BSA, and 1 mM DTT). The kinase reaction was initiated by adding enzyme (2–20 pM) in a black MicroFluor 96-well plate (Dynatech, Chantilly, Va.). After a 40-minute incubation at room temperature, 50 μL of HTRF reagent mixture (420 nM streptavidin-XL665 and 2.0 nM Eu(K)-PY20) in quench buffer (50 mM Hepes, 30 mM EDTA, 0.1% BSA, 0.1% Triton X-100, 0.2 M KF, and pH 7.25) was added to the reaction mixture. The quenched reaction was incubated for 30 min. at room temperature and then read in Discovery (Packard, Meriden, Conn.).

Detailed Assay Procedure

General assay conditions: 0.75 μM substrate (biotinylated peptide), 10 μM ATP, 2-20 pM kinase, 210 nM SA-XL665 (Streptavidin labeled with crosslinked allophycocyanin), 1.0 nM Ab-K (anti-pTyr antibody, PY20, labeled with Europium Cryptate).

Assay Buffer: 50 mM HEPES, 10 mM MgCl$_2$, 1 mg/ml BSA, 1 mM DTT (fresh), 10 μM ATP (fresh), pH 7.0

Quench Buffer: 50 mM HEPES, 30 mM EDTA, 0.2 M KF, 1 mg/ml BSA, 0.1% Triton X-100, pH 7.25

Preparation 1. 1.88 μM substrate[2] from 1 mM stock (in 100% DMSO).
2. 5.4 pM enzyme[2] from 500 nM stock (in 50% glycerol).
3. 420 nM (based on 4 biotin binding sites) SA-XL665 2.0 nM, Ab-K[3] in quench buffer.

Assay Procedure:

1. Add 20 μl of 1.88 μM substrate in a round-bottom 96-well black plate (Dynatech or Costar).
2. Add 2 μl of inhibitor (or DMSO for controls).
3. Add 28 μl of 5.4 pM enzyme.
4. Incubate for 40 min. at RT.
5. Quench the kinase reaction by adding 50 μl of quench buffer with 420 nM XL and 2.0 nM Eu-PY20.
6. Incubate 30 min. at RT.
7. Read in Packard's Discovery.

[1]For 100 μL kinase/200 μL total assay, all the reagents should be doubled.

[2] diluted with assay buffer

[3] diluted with quench buffer

Several methods for preparing the compounds of this invention are illustrated in the following Schemes and Examples. Starting materials are made from known procedures or as illustrated.

SCHEME 1

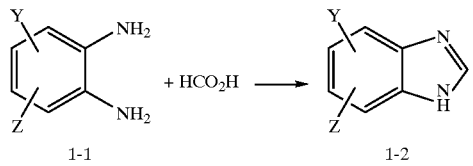

The preparation of substituted benzimidazoles such as 1-2 as intermediates that can be used for the synthesis of compounds within the scope of the instant invention is detailed in Scheme 1. Benzimidazoles of structure 1-2 can be obtained commercially or can be synthesized by reacting a suitably substituted ortho-diaminobenzene 1-1 with formic acid, formamidine, triazine, dimethylformamide, dimethylformamide dialkylacetal, chloromethylenedimethylammonium chloride, trialkylorthoformate, (dimethylaminomethylene)amino-methylene-dimethylammonium chloride (Gold's reagent) or the like. The ortho-diaminobenzene 1-1 can be obtained commercially or can be prepared in a variety of ways from commercial materials. The benzimidazole can be further substituted via aromatic substitution or modification of the substituents prior to or after incorporation onto the pyrimidine ring of the instant invention. The substituents Y and Z may include but are not limited to alkyl, aryl, heteroaryl, nitro, amino, substituted amino, disubstituted amino, hydroxy, alkoxy, aryloxy, chloro, bromo, iodo, fluoro, azido, cyano, thio, alkylthio, arylthio, carboxy, acyl, alkoxycarbonyl and alkylaminocarbonyl groups. Additionally, substituents Y and Z may form a third ring fused to the benzimi-

SCHEME 2

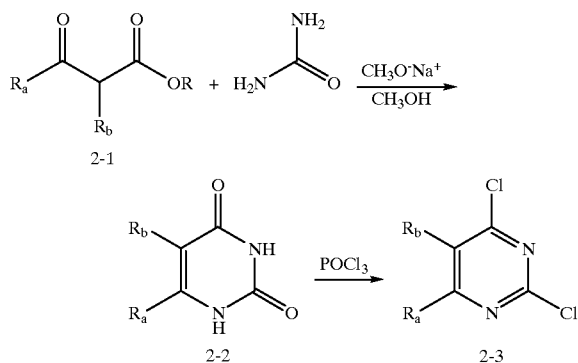

The preparation of 2,4-dichloropyrimidines such as 2-3 as intermediates that can be used for the synthesis of compounds within the scope of the instant invention is detailed in Scheme 2. Pylimidines of structure 2-3 can be obtained commercially or can be synthesized by condensation of a β-keto-ester, β-keto-acid, β-keto-nitrile, β-aldehydo-ester, β-aldehydo-acid, β-aldehydo-nitrile, β-diester, β-ester-nitrile or the like with urea in a suitable solvent such as methanol, ethanol isopropanol or the like in the presence of a base such as a sodium or potassium alkoxide to give a substituted uracil. Other methods of pyrimidine ring formation can be used (see Katritzky, A. R. and Rees, C. W. "Comprehensive Heterocyclic Chemistry" Pergamon Press pp. 106–142 (1984)). The uracil can be chlorinated at the 2- and 4-positions by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, dioxane, ether or other suitable solvent. Alternately, other halides such as bromine or iodine can be incorporated in place of chlorine.

SCHEME 3

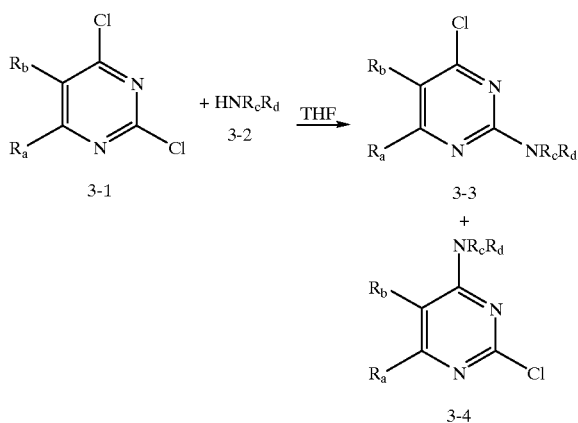

The preparation of some 2-amino-4-chloropyrimidines such as 3-3 as intermediates that can be used for the synthesis of compounds within the scope of the instant invention is detailed in Scheme 3. 2-Amino-4-chloropyrimidines 3-3 can be obtained commercially or can be synthesized by treatment of a 2,4-dichloropyrimidine 3-1 with a primary or secondary amine 3-2 in ethanol, methanol, isopropanol, tetrahydrofuran, ether, dioxane, dichloromethane, chloroform or other suitable solvent with or without the presence of a tertiary amine base. The regioisomelic 2-amino-4-chloropyrimidines are also obtained and can be used as intermediates in the instant invention.

SCHEME 4

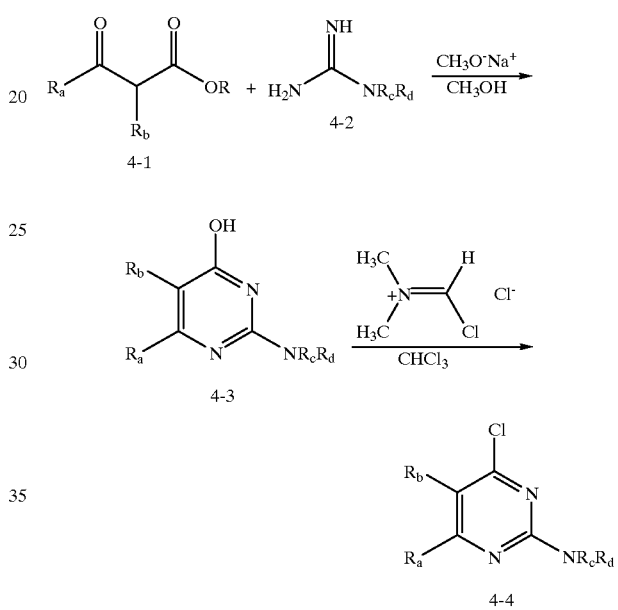

The preparation of some 2-amino-4-chloropyrimidines such as 4-4 as intermediates that can be used for the synthesis of compounds within the scope of the instant invention is detailed in Scheme 4. 2-Amino-4-chloropyrimidines 4-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like with with an N-alkylguanidine 4-2 to give 2-amino-4-hydroxypyrimidine 4-3 generally in an alcoholic solvent such as methanol, ethanol, isopropanol in the presence of a strong base such as sodium methoxide, sodium ethoxide or the like. N-alkylguanidine 4-2 can be prepared according to the procedure of Kim et al (Tetrahedron Letters, 1988, 29, 3183 and references cited therein). The 2-amino-4-hydroxypyrimidinc 4-3 can be chlorinated by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 5

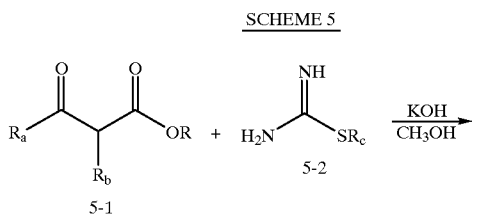

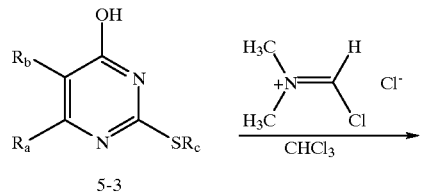

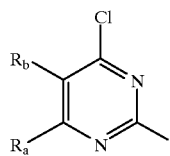

The preparation of some 2-alkylthio-4-chloropyrimidines such as 5-4 as intermediates that can be used for the synthesis of compounds within the scope of the instant invention is detailed in Scheme 5. 2-Alkylthio-4-chloropyrimidines 5-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like in an alcoholic solvent such as methanol, ethanol or the like with an S-alkylthiopseudourea to give 2-alkylthio-4-hydroxy pyrimidine 5-3. The 2-alkylthio-4-hydroxy pyrimidine 5-3 can be chlorinated by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 6

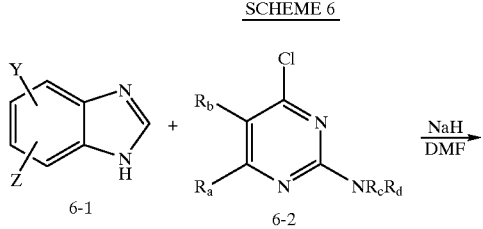

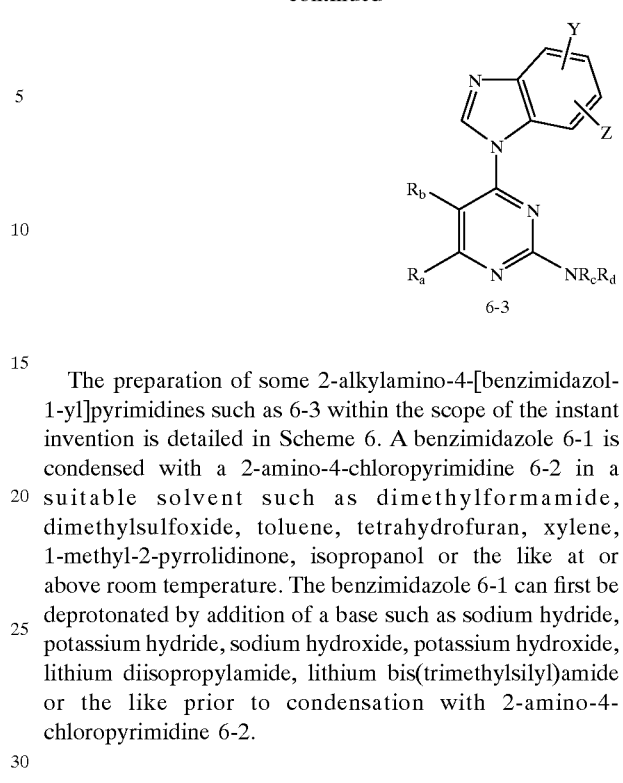

The preparation of some 2-alkylamino-4-[benzimidazol-1-yl]pyrimidines such as 6-3 within the scope of the instant invention is detailed in Scheme 6. A benzimidazole 6-1 is condensed with a 2-amino-4-chloropyrimidine 6-2 in a suitable solvent such as dimethylformamide, dimethylsulfoxide, toluene, tetrahydrofuran, xylene, 1-methyl-2-pyrrolidinone, isopropanol or the like at or above room temperature. The benzimidazole 6-1 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-amino-4-chloropyrimidine 6-2.

SCHEME 7

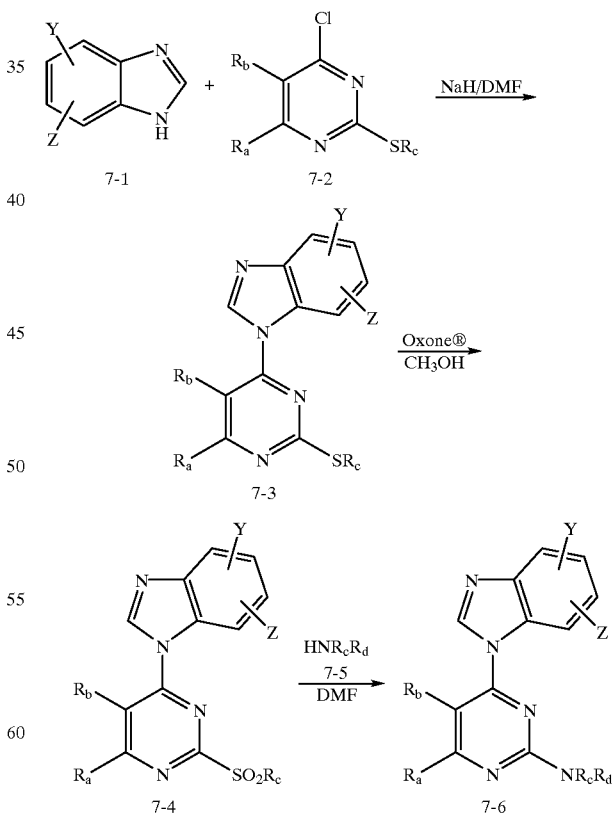

The preparation of some 2-alkylamino-4-[benzimidazol-1-yl]pyrimidines such as 7-6 within the scope of the instant invention is detailed in Scheme 7. A benzimidazole 7-1 is condensed with a 2-alkylthio-4-chloropyrimidine 7-2 in a suitable solvent such as dimethylformamide, dimethylsulfoxide, toluene, tetrahydrofuran, xylene, 1-methyl-2-pyrrolidinone, isopropanol or the like at or above room temperature to afford a 2-alkylthio-4-[benzimidazol-1-yl]pyrimidine 7-3. The benzimidazole 7-1 can first be deprotonated by addition of a base such as sodium hydride, potassium hydride, sodium hydroxide, potassium hydroxide, lithium diusopropylamide, lithium bis(trimethylsilyl)amide or the like prior to condensation with 2-alkylthio-4-chloropyrimidine7-2. The 2-alkylthio-group of 7-3 can be displaced by an alkyl amine 7-5 or preferably, the alkylthio group of 7-3 can first be oxidized to the corresponding sulfoxide or sulfone using hydrogen peroxide, sodium periodate, sodium chlorite, sodium hypochlorite, peracids, Oxone® or the like and then displaced with an alkylamine 7-5 to give 2-alkylamino-4-[benzimidazol-1-yl]pyrimidines such as 7-6.

SCHEME 8

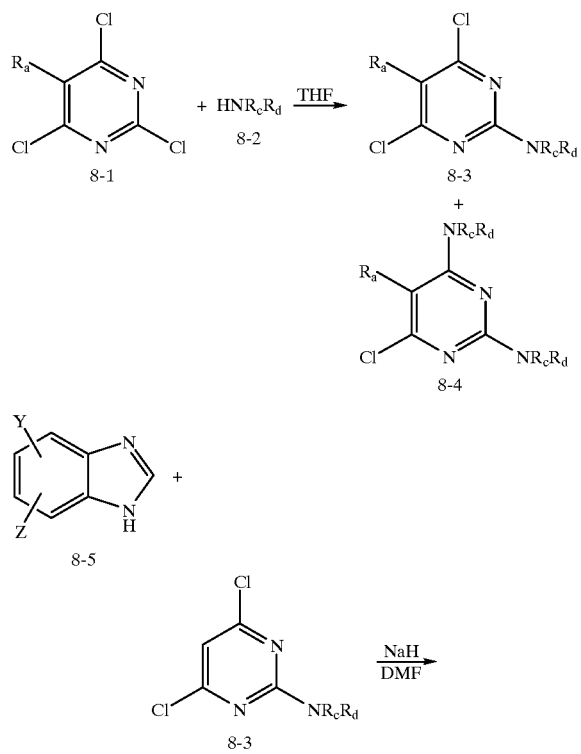

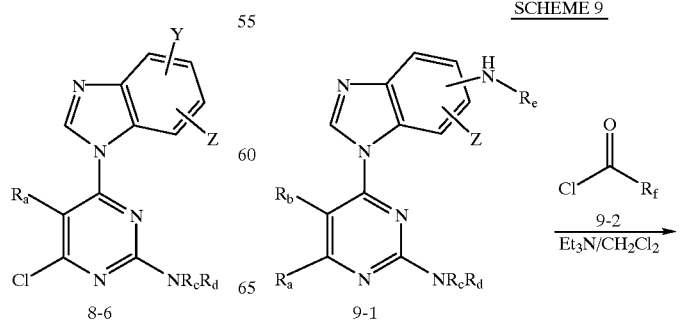

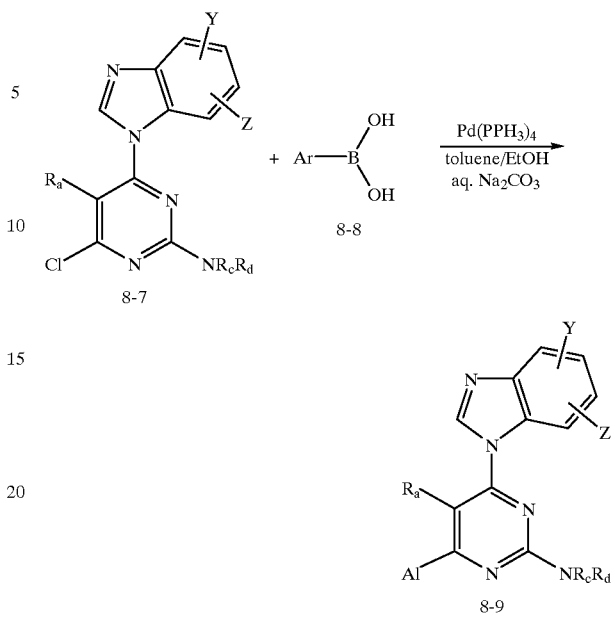

The preparation of some 2-alkylamino-4-[benzimidazol-1-yl]-6-arylpyrimidines such as 8-9 within the scope of the instant invention is detailed in Scheme 8. A 2,4,6-trichloropyrimidinc 8-1 is condensed with an alkylamine 8-2 in ethanol, methanol, isopropanol, tetrahydrofuran, ether, methylene chloride, chloroform or other suitable solvent with or without the presence of a tertiary amine base to afford a 2-alkylamino-4,6-dichloropyrimidine 8-3. A benzimidazole 8-5 is condensed with 2-alkylamino-4,6-dichloropyrimidine 8-3 in a suitable solvent such as dimethylformamide, dimethylsulfoxide, toluene, tetrahydrofuran, xylene, 1-methyl-2-pyrrolidinone, isopropanol or the like at or above room temperature to afford the 2-alkylamino-4-[benzimidazol-1-yl]-6-chloropyrimidine 8-6. The benzimidazole 8-5 can first be deprotonated by addition of a base such as sodium hydride, potassium hydride, sodium hydroxide, potassium hydroxide, lithium diusopropylamide, lithium bis(trimethylsilyl)amide or the like prior to condensation with 2-alkylamino-4,6-dichloropyrimidine 8-3. The 2-alkylamino-4-benzimidazol-1-yl-6-chloropyrimidine 8-6 is arylated via a palladium mediated coupling with an arylboronic acid or an aryltrialkyltin reagent to give 2-alkylamino-4-[benzimidazol-1-yl]-6-arylpyrimidine such as 8-9.

SCHEME 9

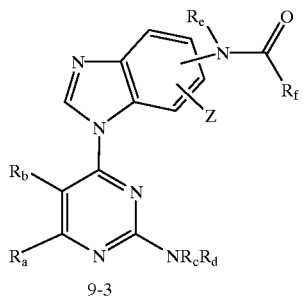

9-3

The preparation of 2-alkylamino-4-[acylamino-benzimidazol-1-yl]pyrimidines such as 9-3 within the scope of the instant invention is detailed in Scheme 9. A 2-aminoalkyl-4-[aminobenzimidazol-1-yl]pyrimidine 9-1 is treated with an acid chloride 9-2 in pyridine or in a non-protic solvent such as methylene chloride, chloroform, tetrahydrofuran, toluene or the like in the presence of a tertiary amine base to give 2-alkylamino-4-facylamino-benzimidazol-1-yl]pyrimidines such as 9-3. In place of the acid chloride one can use another acid halide, or other acylating agent such as acid anhydrides, esters, isocyanates, chloroformates, alkylsulfonylchlorides, arylsulfonylchlorides, or an acid with a coupling reagent such as 1-(3-dimethylaminopropyl)-3-ethylcarbodiimide hydrochloride, 1,3-dicyclohexylcarbodiimide or the like. Alternatively, the acylation can be carried out on a 1-N-protected-amino-benzimidazole. The protecting group for the benzimidazole can be, but is not limited to, a trimethylsilylethoxymethyl (SEM) group. After removal of the 1-N-protecting group the acylamino-benzimidazole can be incorporated onto the pyrimidine nucleus as outlined in Scheme 6, Scheme 7 or Scheme 8 to give compounds of the instant invention.

SCHEME 10

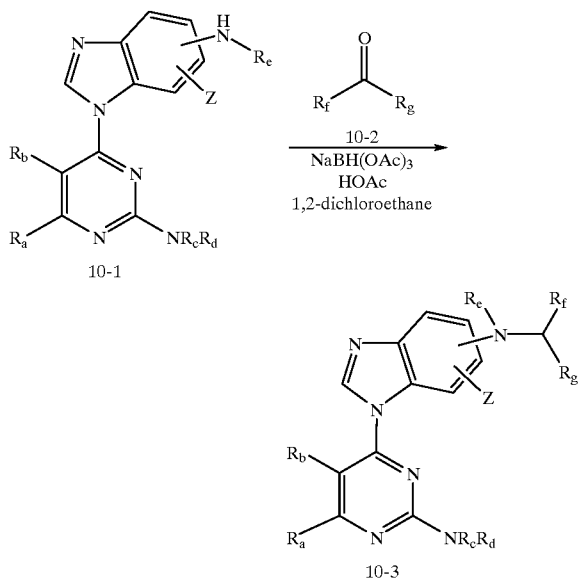

10-1

10-3

The preparation of 2-alkylamino-4[-alkylamino-benzimidazol-1-yl]pyrimidines such as 10-3 within the scope of the instant invention is detailed in Scheme 10. A 2-aminoalkyl-4-[aminobenzimidazol-1-yl]pyrimidine 10-1 is treated with an aldehyde or ketone 10-2 in a suitable solvent such as dichloromethane, dichloroethane, tetrahydrofuran methanol, ethanol, acetic acid or the like to which is added a hydride source such as sodium borohydride, sodium cyanoborohydride, borane, sodium triacetoxyborohydride or the like to give 2-alkylamino-4-[alkylamino-benzimidazol-1-yl]pyrimidines such as 10-3. An alternative method of preparation of 2-alkylamino-4-[alkylamino-benzimidazol-1-yl]pyrimidines such as 10-3 is by the reduction of the amide group of a 2-alkylamino-4-[acylamino-benzimidazol-1-yl]pynimidine using borane, lithium aluminum hydride or the like. An alternative method of preparation of 2-alkylamino-4-[alkylamino-benzimidazol-1-yl]pyrimidines such as 10-3 is by alkylation of a 2-aminoalkyl-4-[aminobenzimidazol-1-yl]pyrimidine 10-1 with an alkyihalide or alkylsulfonate. Alternatively, the alkylation can be carried out on a 1-N-protected-amino-benzimidazole. The protecting group for the benzimidazole can be, but is not limited to, a trimethylsilylethoxymethyl (SEM) group. After removal of the 1-N-protecting group the alkylamino-benzimidazole can be incorporated onto the pyrimidine nucleus as outlined in Scheme 6, Scheme 7 or Scheme 8 to give compounds of the instant invention.

SCHEME 11

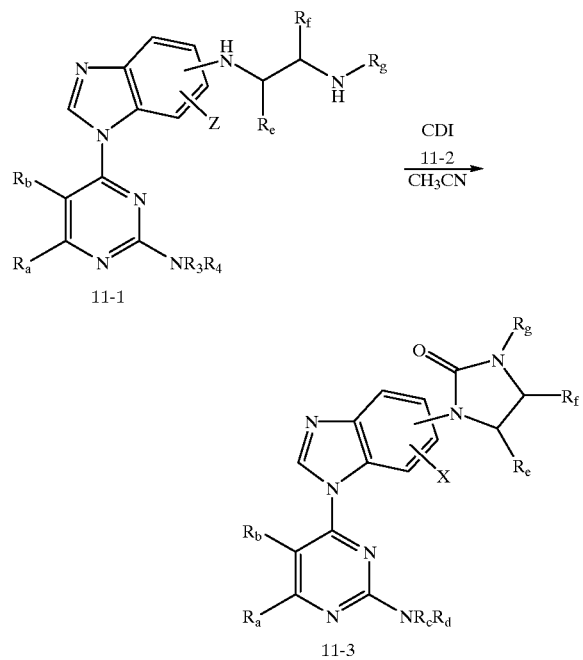

11-1

11-3

The preparation of 2-alkylamino-4-[imidazolidin-2-one-1-yl-benzimidazol-1-yl]pyrimidines such as 11-3 within the scope of the instant invention is detailed in Scheme 11. A 2-alkylamino-4-[(aminoalkyl)amino-benzimidazol-1-yl] pyrimidine 11-1 is treated with carbonyldilmidazole 11-2 or phosgene, triphosgene, 4-nitrophenylchloroformate or the like in a suitable solvent such as dichloromethane, dichloroethane, tetrahydrofuran, acetonitrile, dimethylformamide or the like with or without the presence of a tertiary amine base such as triethylamine, diisopropylethylamine, 4-dimthylaminopyridine or the like to afford the 2-alkylamino-4-[imidazolidin-2-one-1-yl-benzimidazol-1-yl]pyrimidine 11-3. Alternatively, the cyclization can be carried out on a 1-N-protected-(aminoalkyl)amino-benzimidazole. The protecting group for the benzimidazole can be, but is not limited to, a trimethylsilylethoxymethyl (SEM) group. After removal of the 1-N-protecting group the imidazolidin-2-one-1-yl-benzimidazole can be incorporated onto the pyrimidine nucleus as outlined in Scheme 6, Scheme 7 or Scheme 8 to give compounds of the instant invention.

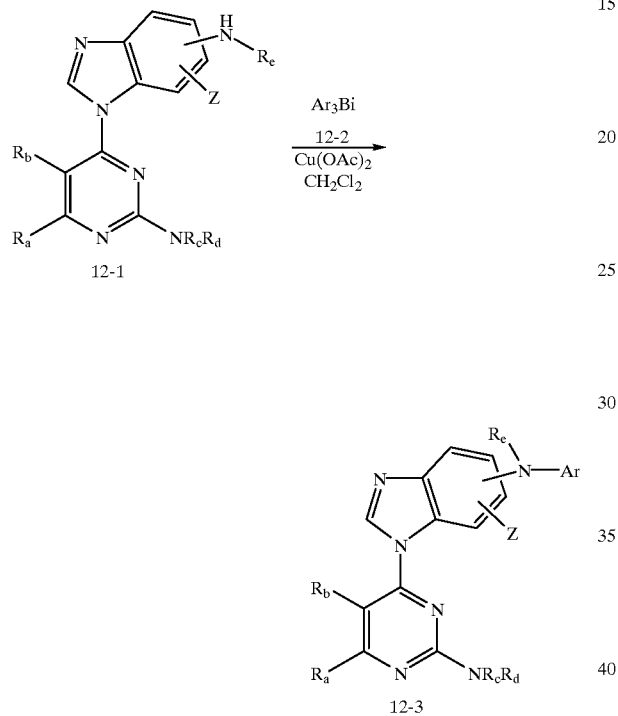

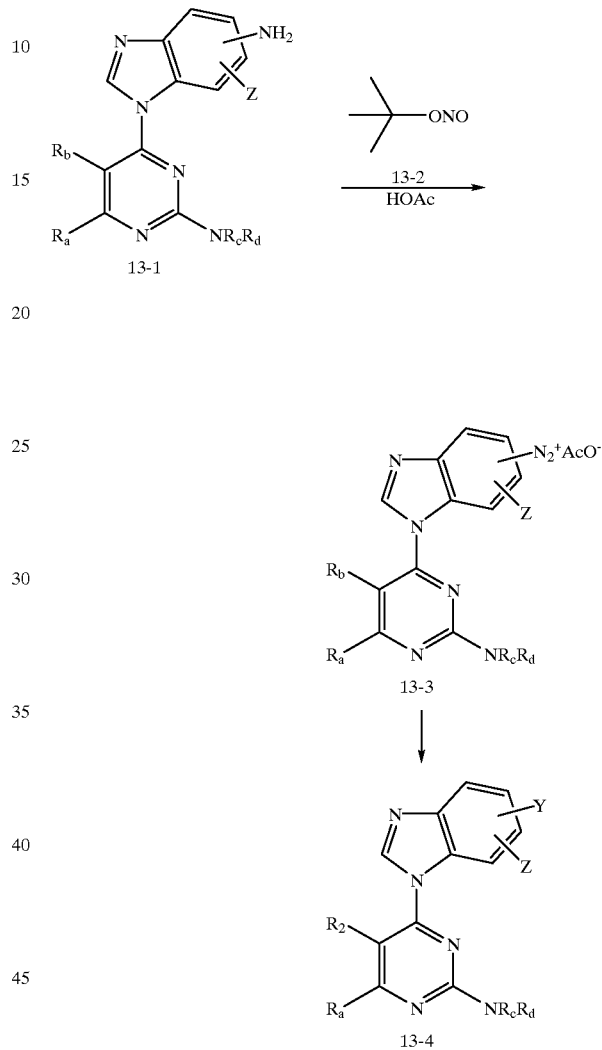

The preparation of 2-alkylamino-4-[arylaminobenzimidazol-1-yl]pyrimidines such as 12-3 within the scope of the instant invention is detailed in Scheme 12. A 2-aminoalkyl-4-[aminobenzimidazol-1-yl]pyrimidine 12-1 is treated with a triarylbismuth 12-2 in the presence of stoichiometric copper(II)acetate or with a triarylbismuth diacetate or other pentavalent organobismuth in the presence of catalytic copper(II)acetate. An alternate procedure involves reaction of a 2-aminoalkyl-4-[aminobenzimidazol-1-yl]pyrimidine 12-1 with an aryl halide in the presence of a palladium catalyst and strong base according to the procedure of Buchwald et al (J. Am. Chem. Soc. 1997, 119, 8451). Alternatively, the arylation can be carried out on a 1-N-protected-amino-benzimidazole. The protecting group for the benzimidazole can be, but is not limited to, a trimethylsilylethoxymethyl (SEM) group. After removal of the 1-N-protecting group the arylaminobenzimidazole can be incorporated onto the pyrimidine nucleus as outlined in Scheme 6, Scheme 7 or Scheme 8 to give compounds of the instant invention.

The preparation of 2-alkylamino-4-[substituted-benzimidazol-1-yl]pyrimidine such as 13-4 within the scope of the instant invention is detailed in Scheme 13. A 2-aminoalkyl-4-[aminobenzimidazol-1-yl]pyrimidine 13-1 is treated with an acid such as acetic acid, tetrafluoroboric acid, hydrochloric acid or the like followed by isoamylnitrite, sodium nitrite, nitrous acid or the like to afford the diazonium salt 13-3. The 2-alkylamino-4-[diazonium-benzimidazol-1-yl]pyrimidines 13-3 can then be treated with cuprous chloride or cuprous bromide or sodium iodide or potassium iodide or the like to afford the corresponding 2-alkylamino-4-[halo-benzimidazol-1-yl] pyrimidine. The 2-alkylamino-4-[diazonium-benzimidazol-1-yl]pyrimidines 13-3 can also be treated with cuprous cyanide to afford the corresponding 2-alkyamino-4-[cyano-benzimidazol-1-yl]pyrimidine. The 2-alkylamino-4-[diazonium-benzimidazol-1-yl]pyrimidines 13-3 can also be treated with sodium azide to afford the corresponding 2-alkylamino-4-[azido-benzimidazol-1-yl]pyrimidine. The 2-alkylamino-4-[diazonium-benzimidazol-1-yl]pyrimidines 12-3 can also be treated with an olefin, a vinylstannane, an arylboronic acid, an arylstannane or the like in the presence of a palladium catalyst to afford the corresponding 2-alkylamino-4-[(aryl or vinyl)-benzimidazol-1-yl]pyrimidine. The stannane couplings can also be done in the presence of carbon monoxide to afford the carbonyl insertion products.

Alternatively, the diazotization and subsequent substitution reaction can be carried out on a 1-N-protected-amino-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

benzimidazole can be incorporated onto the pyrimidine nucleus as outlined in Scheme 6, Scheme 7 or Scheme 8 to give compounds of the instant invention.

SCHEME 15

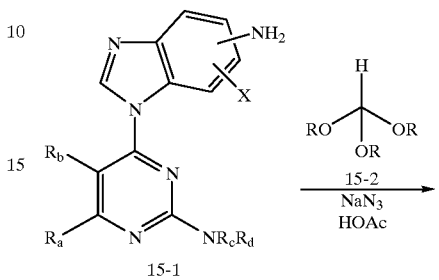

SCHEME 14

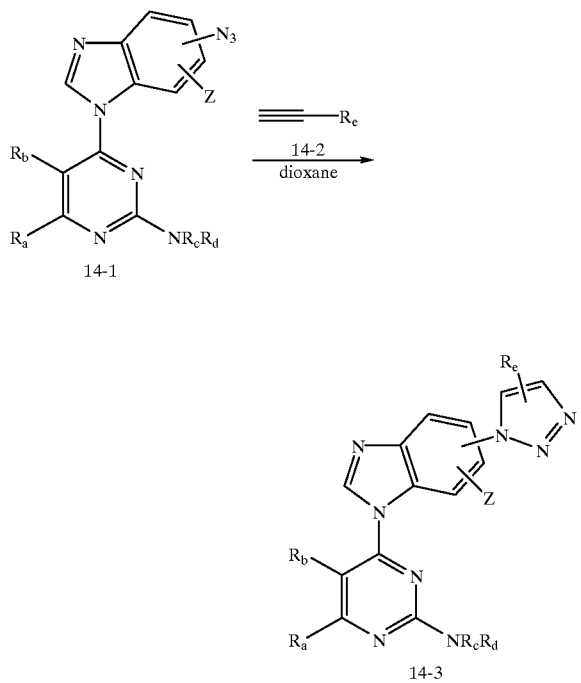

The preparation of 2-alkylamino-4-[tetrazol-1-yl-benzimidazol-1-yl]pyrimidines such as 15-3 within the scope of the instant invention is detailed in Scheme 15. A 2-alkylamino-4-[amino-benzimidazol-1-yl]pyrimidine 15-1 is treated with a trialkyl orthoformate 15-2 followed by treatment with sodium azide to give the 2-alkylamino-4-[tetrazolyl-benzimidazol-1-yl]pyrimidine 15-3. Alternatively, the tetrazole formation can be carried out on a 1-N-protected-amino-benzimidazole. The protecting group for the benzimidazole can be, but is not limited to, a trimethylsilylethoxymethyl (SEM) group. After removal of the 1-N-protecting group the tetrazol-1-yl-benzimidazole can be incorporated onto the pyrimidine nucleus as outlined in Scheme 6, Scheme 7 or Scheme 8 to give compounds of the instant invention.

The preparation of 2-alkylamino-4-[triazol-1-yl-benzimidazol-1-yl]pyrimidine such as 14-3 within the scope of the instant invention is detailed in Scheme 14. A 2-alkylamino-4-[azido-benzimidazol-1-yl]pyrimidine can be treated with an alkyne or aminoacrylate with heating to afford the 2-alkylamino-4-[triazolyl-benzimidazol-1-yl]pyrimidine. When the alkyne used is tributylethynylstannane, the resulting tributylstannyltriazole ($R_5$=bu$_3$Sn) can be used for further palladium catalysed couplings with aryl or olefinic groups or can be protodestannylated. Alternatively, the triazole formation can be carried out on a 1-N-protected-azido-benzimidazole. The protecting group for the benzimidazole can be, but is not limited to, a trimethylsilylethoxymethyl (SEM) group. After removal of the 1-N-protecting group the thiazol-1-yl-

SCHEME 16

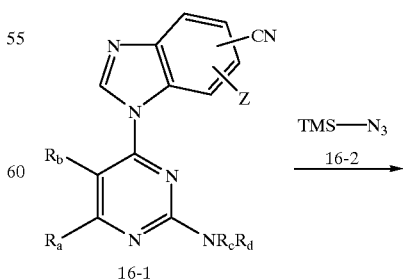

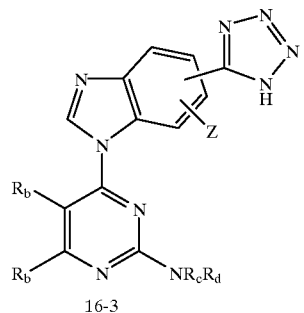

16-3

The preparation of 2-alkylamino-4-[tetrazol-5-yl-benzimidazol-1-yl]pyrimidines such as 16-3 within the scope of the instant invention is detailed in Scheme 16. A 2-alkylamino-4-[cyano-benzimidazol-1-yl]pyrimidine 16-1 is treated with trimethylsilyl azide 16-2 or trialkyltin azide or sodium azide or the like at or above room temperature to give the 2-alkylamino-4-[tetrazol-5-yl-benzimidazol-1-yl]pyrimidine 16-3. Alternatively, the tetrazole formation can be carried out on a 1-N-protected-cyano-benzimidazole. The protecting group for the benzimidazole can be, but is not limited to, a trimethylsilylethoxymethyl (SEM) group. After removal of the 1-N-protecting group the tetrazol-5-yl-benzimidazole can be incorporated onto the pyrimidine nucleus as outlined in Scheme 6, Scheme 7 or Scheme 8 to give compounds of the instant invention.

SCHEME 17

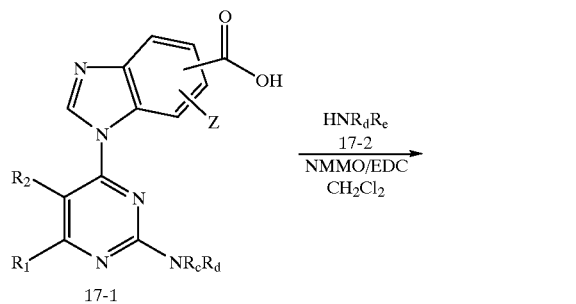

The preparation of 2-alkylamino-4-[(alkylaminocarbonyl)-benzimidazol-1-yl]pyrimidines such as 17-3 within the scope of the instant invention is detailed in Scheme 17. A 2-alkylamino-4-[carboxy-benzimidazol-1-yl]pyrimidine 17-1 is treated with an amine 17-2 in the presence of a tertiary amine such as N-methylmorpholine, triethylamine or the like and a coupling reagent such as 1,3-dicyclohexylcarbodiimide, 1-(3-dimethylaminopropyl)-3-ethylcarbodiimide hydrochloride or the like to give the 2-alkylamino-4-[(alkylaminocarbonyl)-benzimidazol-1-yl]pyrimidine 17-3. Alternatively, the amide formation can be carried out on a 1-N-protected-carboxy-benzimidazole. The protecting group for the benzimidazole can be, but is not limited to, a trimethylsilylethoxymethyl (SEM) group. After removal of the 1-N-protecting group the (alkylaminocarbonyl)-benzimidazole can be incorporated onto the pyrimidine nucleus as outlined in Scheme 6, Scheme 7 or Scheme 8 to give compounds of the instant invention.

SCHEME 18

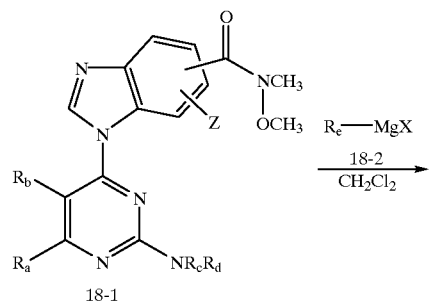

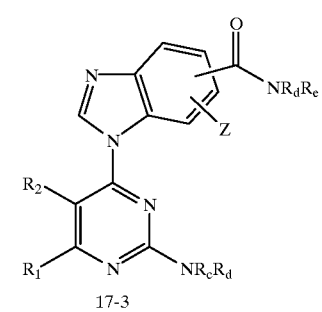

18-3

The preparation of 2-alkylamino-4-[alkyl (or aryl) carbonyl-benzimidazol-1-yl]pyrimidines such as 18-3 within the scope of the instant invention is detailed in Scheme 18. A 2-alkylamino-4-[(N-methyl-N-methoxyamino)carbonyl-benzimidazol-1-yl]pyrimidine 18-1 is treated with an organomagnesium halide 18-2 or organolithium or the like in a suitable solvent such as dichloromethane, ether, tetrahydrofuran, dichloroethane, dioxane or the like to give the 2-alkylamino-4-[alkyl (or aryl)carbonyl-benzimidazol-1-yl]pyrimidine 18-3. Alternatively, the ketone formation can be carried out on a 1-N-protected-(N-methyl-N-methoxyamino)carbonyl-benzimidazole. The protecting group for the benzimidazole can be, but is not limited to, a trimethylsilylethoxymethyl (SEM) group. After removal of the 1-N-protecting group the alkyl (or aryl)carbonyl-benzimidazole can be incorporated onto the pyrimidine nucleus as outlined in Scheme 6, Scheme 7 or Scheme 8 to give compounds of the instant invention.

SCHEME 19

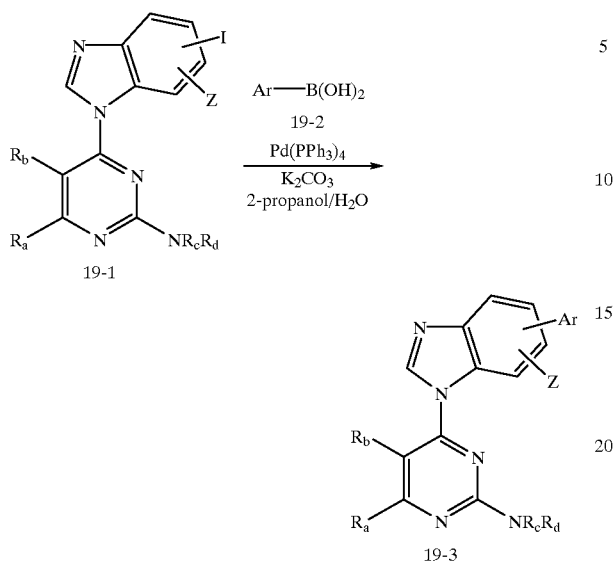

The preparation of 2-alkylamino-4-[substituted-benzimidazol-1-yl]pyrimidine such as 19-3 within the scope of the instant invention is detailed in Scheme 19. A 2-aminoalkyl-4-[iodobenzimidazol-1-yl]pyrimidine 19-1 or 2-aminoalkyl-4-[bromobenzimidazol-1-yl]pyrimidine or 2-aminoalkyl-4-[chlorobenzimidazol-1-yl]pyrimidine is treated with an olefin, arylstannane, vinylstannane, arylboronic acid, vinylboronic acid or the like in the presence of a palladium catalyst to afford the corresponding 2-alkylamino-4-[(aryl or vinyl)-benzimidazol-1-yl]pyrimidine 19-3. The stannane couplings can also be done in the presence of carbon monoxide to afford carbonyl insertion products. Alternatively, the 2-aminoalkyl-4-[iodobenzimidazol-1-yl]pyrimidine 19-1 or 2-aminoalkyl-4-[bromobenzimidazol-1-yl]pyrimidine or 2-aminoalkyl-4-[chlorobenzimidazol-1-yl]pyrimidine can be treated with hexabutylditin or hexamethylditin in the presence of a palladium catalyst to afford the corresponding 2-aminoalkyl-4-[trialkylstannylbenzimidazol-1-yl]pyrimidine which can also be employed in palladium mediated couplings with arylboronic acids, vinyl boronic acids, arylhalides, vinyl halides or the like. Alternatively, the arylation or vinylation can be carried out on a 1-N-protected-halo (or stannyl)-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

Scheme 20

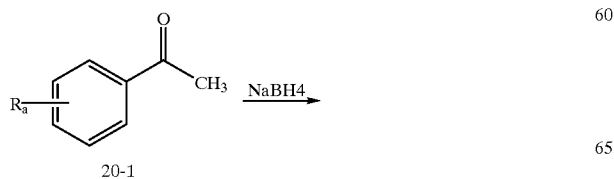

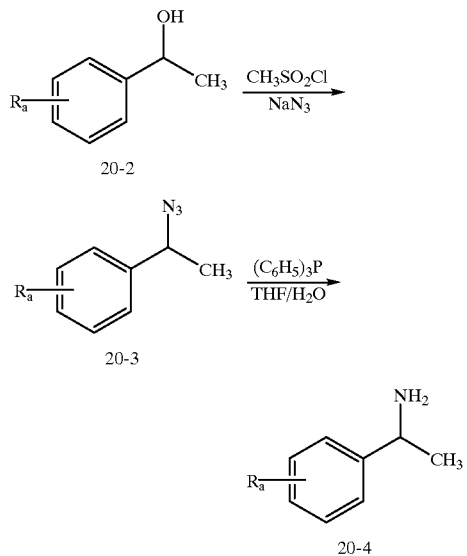

The preparation of some 1-phenylethylamines such as 20-4 as intermediates that can be used for the synthesis of compounds within the scope of the instant invention is detailed in Scheme 20. I-phenylethylamines of structure 20-4 can be obtained commercially or can be synthesized by the reduction of an acetophenone to the corresponding alcohol. Activation of the alcohol towards displacement by formation of the methanesulfonate, toluenesulfonate, halhalide or the like followed by substitution with the azide anion affords azido compound 20-3. Reduction of the azide by treatment with triphenylphosphine in aqueous THF or by hydrogenation over a palladium catalyst affords the amine 20-4. Other methods of amine formation can be used (see March J. "Advanced Organic Chemistry", 4th ed., John Wiley & Sons, New York, pp. 1276–1277(1992)).

Scheme 21

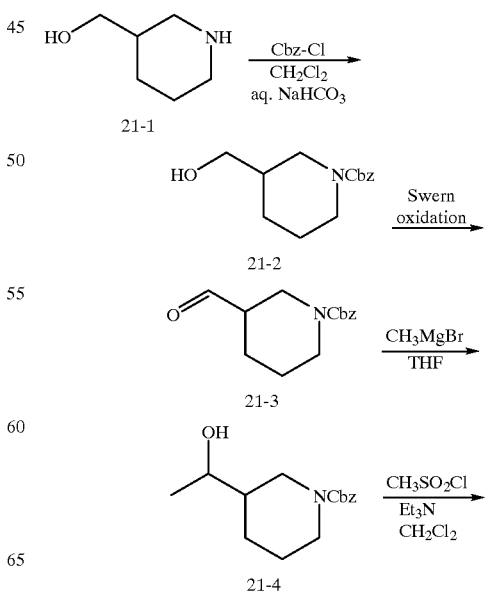

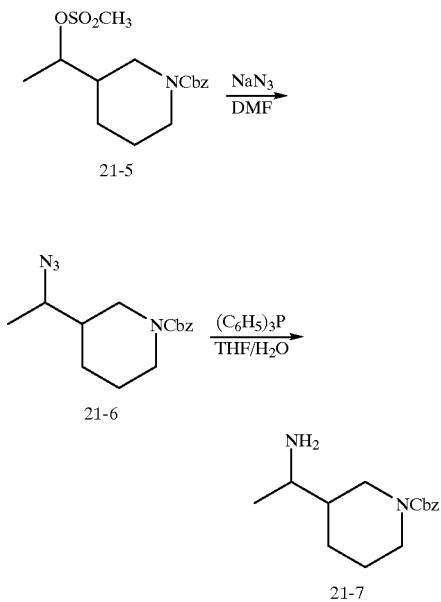

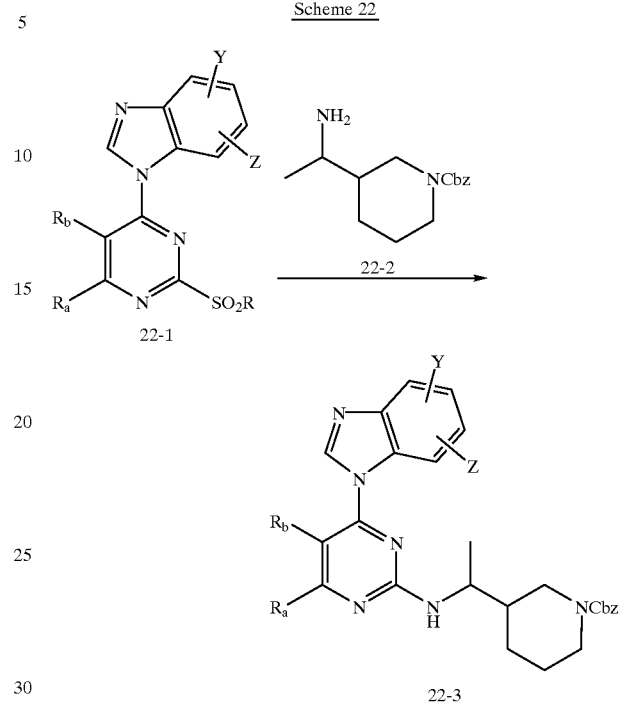

The preparation of piperidine substituted ethylamines such as 21-7 as intermediates that can be used for the synthesis of compounds within the scope of the instant invention is detailed in Scheme 21. The nitrogen of the commercially available 3-piperidinemethanol can be protected with a benzyloxycarbonyl group or other suitable protecting group such as tert-butyloxycarbonyl-, allyloxycarbonyl- or the like to afford 21-2. The hydroxyl group of 21-2 can be oxidized to the corresponding carbonyl group under Swein oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Addition of methyl magnesium bromide or methyl lithium can afford the secondary alcohol 21-4. The hydroxyl group of 21-4 can be activated towards displacement by formation of methanesulfonate, toluenesulfonate, halide or the like. Treatment of 21-5 with sodium azide in dimethylformamide or other suitable solvent affords azido compound 21-6. Alternatively, 21-4 can be treated with azide ion under Mitsunobu coupling conditions to give azide 21-6 directly. Reduction of the azide to the corresponding amine by treatment of the azide with triphenylphosphine in aqueous THF gives the desired amine 21-7. Alternatively, the azide can be reduced by hydrogenation over a suitable catalyst. Alkylamines substituted with other heterocycles such as, but not limited to, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be prepared in like manner.

The preparation of 2-(piperidin-3-yl)ethylamino-4-[benzimidazol-1-yl]pyrimidines such as 22-3 within the scope of the instant invention is detailed in Scheme 22. Sulfone 22-1 described in Scheme 7 can be reacted with a piperidine-substituted alkylamines such as 22-2 in dimethyformamide, dimethylsulfoxide, toluene, 1-methyl-2-pyrrolidinone, isopropanol or other suitable solvent with or without heating to give the N-benzyloxycarbonyl-protected heterocycle 22-3. Alternatively, the (piperidin-3-yl)ethylamino can be affixed to the pyrimidine ring prior to the benzimidazole as described in Scheme 3, Scheme 6 and Scheme 8. Additionally, other (heterocyclic)alkylamines such as alkylamines substituted with, for example, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be used.

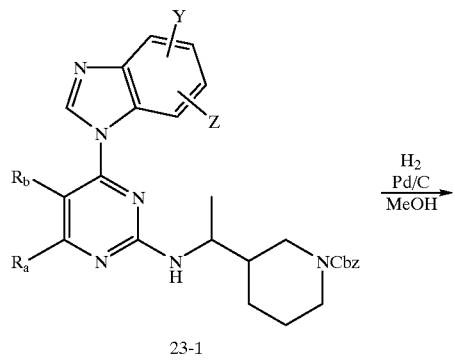

Scheme 24

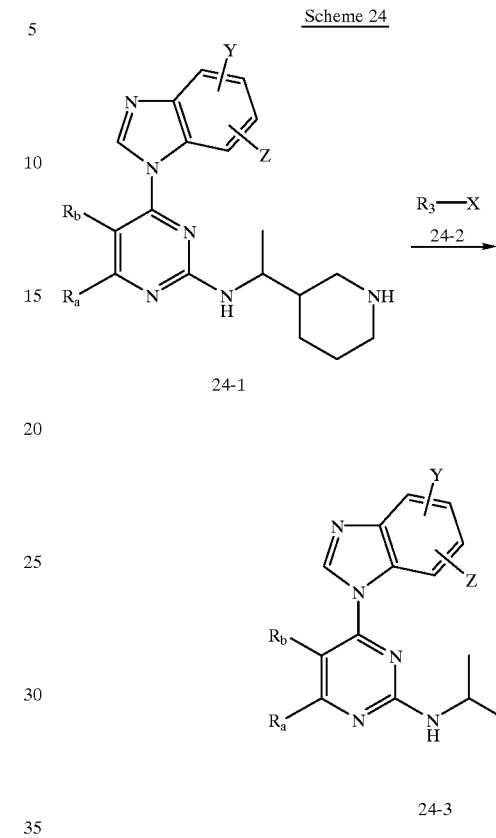

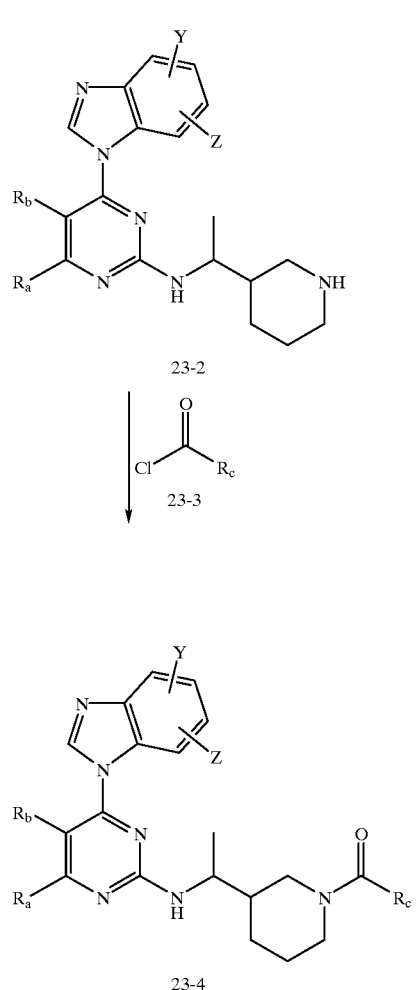

The preparation of 2-(piperidin-3-yl)ethylamino-4-[benzimidazol-1-yl]pyrimidines such as 24-3 within the scope of the instant invention is detailed in Scheme 24. Treatment of piperidine 24-1 with an alkyl halide, or alkylsulfonate or the like in dichloromethane, dichloroethane, tetrahydrofuran, dioxane, dimethylformamide, dimethylsulfoxide acetone or other suitable solvent in the presence of a tertiary amine base such as triethylamine, diusopropylethylamine or the like affords the alkylpiperidine derivative 24-3. Alternatively, 24-1 can be treated with an aldehyde or ketone under reductive alkylation conditions to give the alkylpiperidine derivative 24-3. Alternatively, the alkylation can be carried out on the (heterocyclic)alkylamine prior to incorporation onto the pyrimidine ring of the instant invention.

The preparation of 2-(piperidin-3-yl)ethylamino-4-[benzimidazol-1-yl]pyrimidines such as 23-4 within the scope of the instant invention is detailed in Scheme 23. Removal of the benzyloxycarbonyl protecting group of 23-1 via hydrogenolysis using a palladium catalyst or by solvolysis using HBr in acetic acid affords the deprotected compound 23-2 within the scope of the instant invention. Subsequent acylation with an acid chloride 22-3 in pyridine or in a solvent such as methylene chloride, chloroform, tetrahydrofuran, toluene or the like in the presence of a tertiary amine base gives 22-4. In place of the acid chloride one can use another acid halide, or other acylating agent such as acid anhydrides, esters, isocyanates, chloroformates, alkylsulfonyl halides, arylsulfonyl halides or an acid with a coupling reagent such as 1-(3-dimethylaminopropyl)-3-ethylcarbodiimide hydrochloride or 1,3- dicyclohexylcarbodiimide or the like. Alternatively, the acylation can be carried out on the (heterocyclic)alkylamine prior to incorporation onto the pylimidine ring of the instant invention.

SCHEME 25

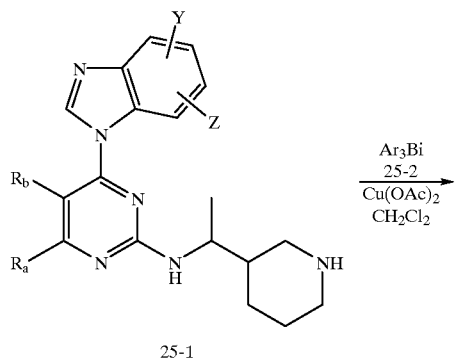

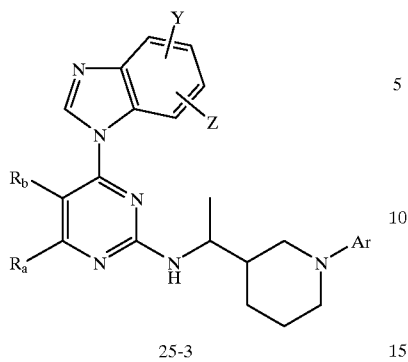

25-3

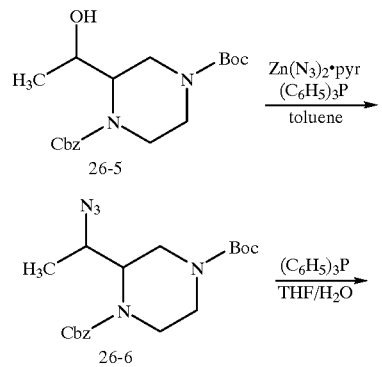

26-5

The preparation of 2-(N-arylpiperidine)ethylamino-4-[benzimidazol-1-yl]pyrimidines such as 25-3 within the scope of the instant invention is detailed in Scheme 12. A 2-(piperidin-3-yl)ethylamino-4-[benzimidazol-1-yl] pyrimidine 25-1 is treated with a triarylbismuth 25-2 in the presence of stoichiometric copper(II)acetate or with a triarylbismuth diacetate or other pentavalent organobismuth in the presence of catalytic copper(II)acetate to afford 25-3. An alternate procedure involves reaction of a 2-(piperidin-3-yl) ethylamino-4-[benzimidazol-1-yl]pyrimidine 25-1 with an aryl halide in the presence of a palladium catalyst and strong base according to the procedure of Buchwald et al (J. Am. Chem. Soc. 1997, 119, 8451). Alternatively, the arylation can be carried out on the (heterocyclic)alkylamine prior to incorporation onto the pyrimidine ring of the instant invention.

SCHEME 26

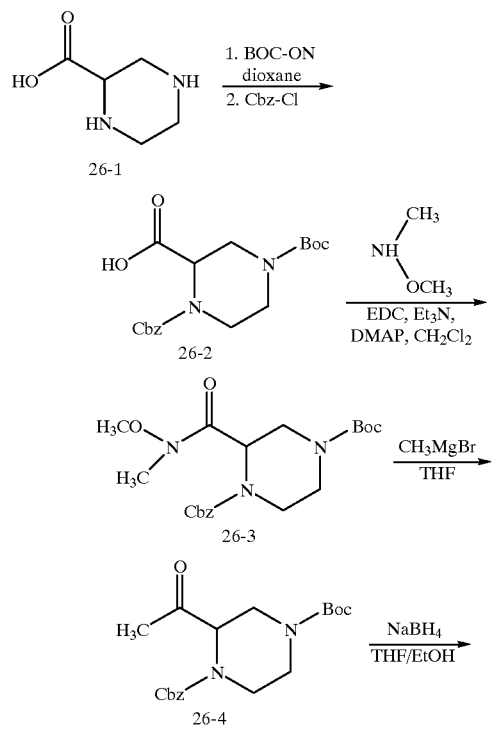

The preparation of piperazine substituted alkylamines such as 26-7 as intermediates that can be used for the synthesis of compounds within the scope of the instant invention is detailed in Scheme 26. The nitrogens of the commercially available piperazine-2-carboxylic acid can be sequentially protected with a tert-butyloxycarbonyl group using tert-(butoyxcarbonyloxyimino)-2-phenylacetonitrile (BOC-ON) and benzyloxycarbonyl group using benzylchloroformate to afford 26-2. Condensation of the carboxylic acid group of 26-2 with N-methoxy-N-methyl amine using a coupling agent such as 1,3-dicyclohexylcarbodiimide, 1-(3-dimethylaminopropyl)-3-ethylcarbodiimide hydrochloride or the like affords the corresponding amide 26-3. Addition of methylmagnesium bromide affords the acetylpiperazine 26-4. The carbonyl of 26-4 is reduced using sodium borohydride to give alcohol 26-5. Treatment of 26-5 with zinc azide.pyridine complex in the presence of triphenylphosphine in toluene affords azido compound 26-6. Reduction of the azide to the corresponding amine by treatment with triphenylphosphine in aqueous THF gives the desired amine 26-7. Alternatively, the azide can be reduced by hydrogenation over a catalyst.

Scheme 27

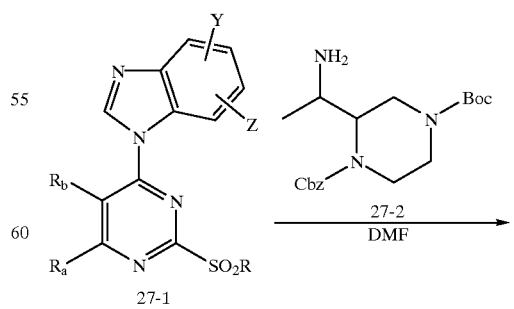

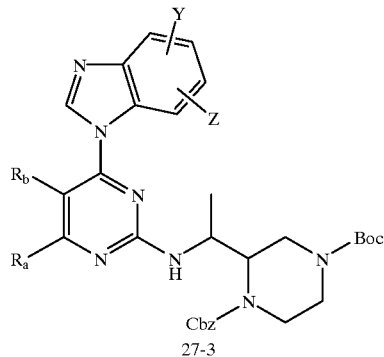
27-3

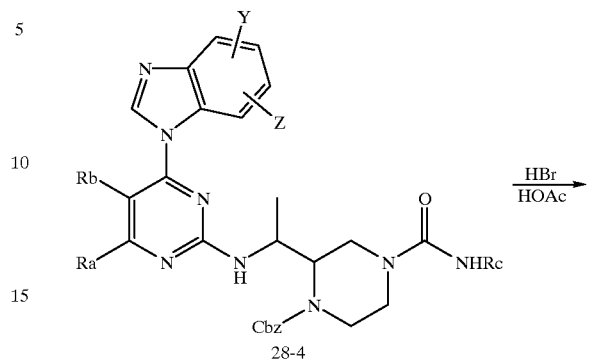
28-4

The preparation of 2-(piperazin-2-yl)ethylamino-4-[benzimidazol-1-yl]pyrimidines such as 27-3 within the scope of the instant invention is detailed in Scheme 27. Sulfone 27-1 described in Scheme 7 can be reacted with a piperazine-substituted alkylamines such as 27-2 in dimethyformamide, dimethylsulfoxide, toluene, 1-methyl-2-pyrrolidinone, isopropanol or other suitable solvent with or without heating to give the N-benzyloxycarbonylprotected heterocycle 27-3. Alternatively, the (piperidin-3-yl)ethylamino can be affixed to the pyrimidine ring prior to the benzimidazole as described in Scheme 3, Scheme 6 and Scheme 8.

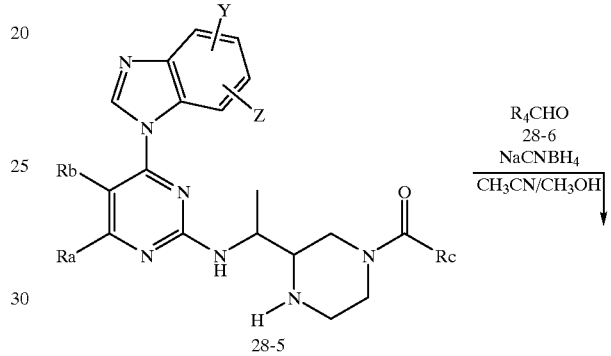
28-5

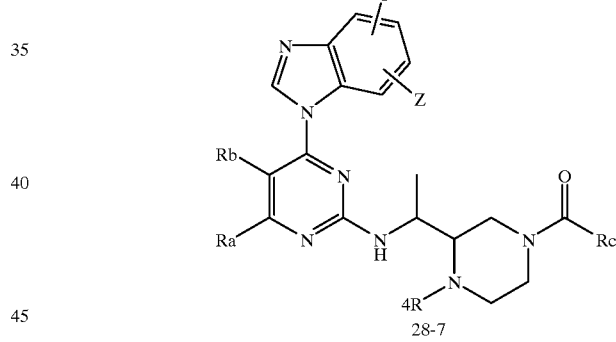
28-7

Scheme 28

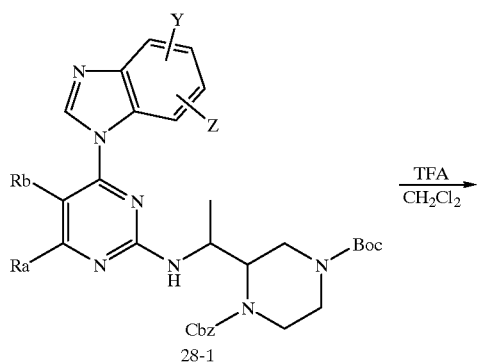
28-1

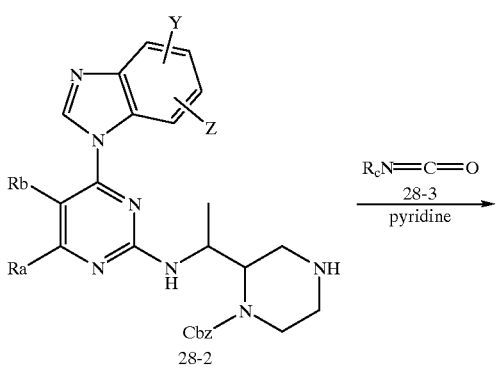
28-2

The preparation of 2-(piperazin-2-yl)ethylamino-4-[benzimidazol-1-yl]pyrimidines such as 28-7 within the scope of the instant invention is detailed in Scheme 23. Removal of the tert-butyloxycarbonyl protecting group of 28-1 via hydrolysis using trifluoroacetic acid affords the mono-deprotected compound 28-2 within the scope of the instant invention. Subsequent acylation with an isocyanate 28-3 in pyridine gives 28-4. Alternatively, acylation can be carried out using an acid chloride or another acid halide, or other acylating agents such as acid anhydrides, esters, chloroformates, alkylsulfonyl halides, arylsulfonyl halides in pyridine or in a non-protic solvent such as methylene chloride, chloroform, tetrahydrofuran, toluene or the like in the presence of a tertiary amine base. Additionally, acylation can be carried out with an acid employing a coupling reagent such as 1-(3-dimethylaminopropyl)-3-ethylcarbodiimide hydrochloride or 1,3-dicyclohexylcarbodiimide or the like. Alternatively, the secondary amine of the piperazine of compound 28-2 may be alkylated as described in Scheme 24 or arylated as described in Scheme 25. Deprotection of the benzyloxycarbonyl group can be effected by HBr in acetic acid to afford 28-5. Alkylation of 28-5 can be achieved by condensation with an aldehyde 28-6 followed by reduction using sodium borohydride, sodium cyanoborohydride, sodium triacetoxyborohydride or the like. Alternatively, the secondary amine of compound 28-5 can be acylated, alkylated or arlated as described above. Alternatively, modification of the piperazine-substituted-ethylamine can be carried out prior to incorporation onto the pyrimidine ring of the instant invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims, which follow, and that such claims be interpreted as broadly as is reasonable.

EXAMPLE 1

2-Methanesulfonyl-4-[benzimidazol-1-yl]pyrimidine

Step A: 2-Methylthio-4-[benzimidazol-1-yl]pyrimidine

A mixture of NaH (0.548 mg, 22.8 mmol), benzimidazole (0.52 g, 21.3 mmol) and 4-chloro-2-methylthiopyrimidine (2.48 mL, 21.3 mmol) in 30 mL of DMF was heated to 100° C. for 30 min. The reaction was quenched with $H_2O$ and extracted with EtOAc. The combined organic fractions were washed with brine, dried over $MgSO_4$, filtered and concentrated. The residue was purified by chromatography (silica, 0–10% MeOH:$CH_2Cl_2$) to give 1.99 g of the title compound. $^1$H NMR (500 MHz, $CDCl_3$): $\delta$8.69 (s, 1H); 8.64 (d, J=5.5 Hz, 1H); 8.22 (dd, J=1.4, 7.3 Hz); 7.89 (dd, J=1.6, 7.3 Hz); 7.44 (m, 2H); 7.23 (d, J=5.7 Hz, 1H); 2.69 (s, 3H).

Step B: 2-Methanesulfonyl-4-[benzimidazol-1-yl] pyrimidine

To a solution of 2-methylthio-4-[benzimidazol-1-yl] pyrimidine (1.99 g, 8.21 mmol) in $CH_2Cl_2$ (50 mL) at 0° C. was added 3-chloroperoxybenzoic acid (2.8 g, 16 mmol). The reaction was permitted to warm to room temperature and stirred. After 24 h, 2.8 g more of 3-chloroperoxybenzoic acid was added. After 24 h, saturated $NaHCO_3$ solution was added and the mixture was extracted twice with $CH_2Cl_2$. The combined organic fractions were washed with brine, dried over $MgSO_4$, filtered and the filtrate was concentrated. The residue was purified by chromatography (silica, 1:1 hexanes: EtOAc) give 0.59 g of the title compound. $^1$H NMR (500 MHz, $CDCl_3$): $\delta$9.00 (d, J=5.7 Hz, 1H); 8.72 (s, 1H); 8.40 (d, J=8.2 Hz, 1H); 7.91 (d, J=7.7 Hz, 1H); 7.76 (d, J=5.7 Hz, 1H); 7.53 (m, 1H); 7.48 (m, 1H); 3.46 (s, 3H).

EXAMPLE 2

2-Hexanethio-4-[benzimidazol-1-yl]pyrimidine

Step A: 2-Hexanethio-4-hydroxypyrimidine

To a stirred suspension of 10 g of thiouracil in THF (100 mL) was added triethylamine (22 mL) and todohexane (11.5 mL). The mixture was heated to and maintained at reflux for 3 h. The heating bath was removed and the mixture was stirred overnight. Todohexane (2 mL) was added and the mixture was brought to and maintained at reflux for 8 h. The heating bath was removed and the mixture was stirred overnight. Todohexane (2 mL) was added and the mixture was brought to and maintained at reflux for 3 h. The mixture was allowed to cool to room temperature and the THF was removed under reduced pressure. The residue was diluted with water and extracted 3× with ethyl acetate. The organic extracts were combined, dried over anhydrous $Na_2SO_4$, filtered and concentrated. The product was recrystallized from hexanes giving 8.45 g of the title compound. $^1$H NMR (500 MHz, $CDCl_3$): $\delta$7.78 (1H,d, J=7 Hz); 6.23 (1H, d, J=7 Hz); 3.20 (2H, t, J=7.5 Hz); 1.73 (2H, m); 1.44 (2H, m); 1.32 (4H, m); 0.90 (3H, t, J=7 Hz).

Step B: 4-Chloro-2-hexanethiopyrimidine

To a stirred solution of 2-hexanethio-4-hydroxypyrimidine (8.45 g) in $CHCl_3$ (passed over basic alumina) at 0° C. under $N_2$ was added chloromethylenedimethylammonium chloride (7.64 g) in two portions. The mixture was stirred 10 min at 0° C. and the cooling bath was removed. The mixture was stirred 2.5 h under $N_2$, then poured into a separatory funnel containing water plus saturated aqueous $NaHCO_3$. The layers were mixed carefully (much $CO_2$ liberation). The layers were separated and the aqueous layer was extracted 2× with $CH_2Cl_2$. The organic extracts were combined, dried over anhydrous $Na_2SO_4$, filtered and concentrated. The residue was loaded onto a large silica gel plug and eluted with 5:1 hexanes/acetone. The product containing fractions were concentrated giving 7.8 g of the title compound. $^1$H NMR (500 MHz, $CDCl_3$): $\delta$8.37 (1H, d, J=5.5 Hz); 6.99 (1H, d, J=5.5 Hz); 3.16 (2H), t, J=7.5 Hz); 1.74 (2H, m); 1.47 (2H, m); 1.34 (4H, m); 0.91 (3H, t, J=7 Hz).

Step C: 2-Hexanethio-4-[benzimidazol-1-yl]pyrimidine

To a stirred solution of benzimidazole (1 g) in DMF (20 mL) at 0° C. under $N_2$ was added NaH (in two portions totalling 340 mg of a 60% dispersion in oil). After 15 min the cooling bath was removed and the mixture stirred. After an additional 15 min the benzimidazole sodium salt solution was added to a solution of 4-chloro-2-hexanethiopyrimidine (1.63 g) in DMF (20 mL) via syringe. The resulting mixture was stirred overnight under $N_2$. The DMF was removed under reduced pressure. The residue was diluted with $CH_2Cl_2$ and washed with water. The aqueous layer was back extracted with $CH_2Cl_2$. The organic extracts were combined, dried over anhydrous $Na_2SO_4$, filtered and concentrated. The residue was triturated with diethyl ether to afford 1.3 g of the title compound. $^1$H NMR (500 MHz, $CDCl_3$): $\delta$8.68 (1H, s); 8.63 (1H, d, J=5.5 Hz), 8.21 (1H, m); 7.89 (1H, m); 7.44 (2H, m); 7.22 (1H, d, J=5.5 Hz); 3.26 (2H, t, J=7.5 Hz); 1.83 (2H, m); 1.53 (2H, m); 1.36 (4H, m); 0.92 (3H, t, J=7 Hz).

EXAMPLE 3

2-Methylthio-4-[5-aminobenzimidazol-1-yl]pyrimidine and 2-methylthio-4-[6-aminobenzimidazol-1-yl]pyrimidine Step A: 5-Aminobenzimidazole To a stirred solution of 5-nitrobenzimidazole (1 g, 6.13 mmol, 1 eq) in THF (100 mL) was added 10% palladium on carbon (385 mg). The flask was purged with $H_2$ and the mixture was stirred under a balloon of $H_2$ for several hours. The flask was purged with $N_2$. The catalyst was filtered and washed with MeOH. The solution was concentrated under reduced pressure giving 800 mg of the desired product.

Step B: 2-Methylthio-4-[5-aminobenzimidazol-1-yl]pyrimidine and 2-methylthio-4-[6-aminobenzimidazol-1-yl]pyrimidine To a stirred solution of 5-aminobenzimidazole (700 mg, 5.26 mmol, 1 eq) in DMF (21 mL) was added NaH (231 mg, 5.78 mmol, 1.1 eq, (60% suspension in oil)). The mixture was allowed to stir until gas evolution ceased. To the DMF solution was added 2-methylthio-4-chloropyrimidine (0.612 mL, 5.26 mmol, 1 eq) dropwise via syringe. The mixture was allowed to stir overnight. The DMF was removed under reduced pressure and the residue was diluted with water and extracted 3× with $CH_2Cl_2$. The organic extracts were combined, dried over anhydrous $Na_2SO_4$, filtered and concentrated under reduced pressure. The mixture was purified by preparative thin layer chromatography (eluted 2× with 3.5% MeOH/$CH_2Cl_2$) to give 149 mg 2-methylthio-4-[6-aminobenzimidazol-1-yl]pyrimidine (faster regioisomer) and 89 mg 2-methylthio-4-[5-aminobenzimidazol-i-yl]pyrimidine (slower regioisomer). 2-methylthio-4-[6-aminobenzimidazol-1-yl]pyrimidine (faster regioisomer): $^1$H NMR (500 MHz, $CD_3OD$): δ8.68 (1H, s); 8.58 (1H, d, J=5.5 Hz); 7.68 (1H, d, J=2 Hz); 7.45 (2H, m); 6.81 (IH, dd, J=2 Hz, J=8.5 Hz); 2.67 (3H, s). 2-methylthio-4-[5-aminobenzimidazol-1-yl]pyrimidine (slower regioisomer): $^1$H NMR (500 MHz, $CD_3OD$): δ8.81 (1H, s); 8.56 (1H, d, J=5.5 Hz); 8.11 (1H, d, J=8.5 Hz); 7.46 (1H, d, J=5.5 Hz); 7.04 (1H, d, J=2 Hz); 6.87 (1H, dd, J=2 Hz, J=8.5 Hz); 2.65 (3H, s).

EXAMPLE 4

2-Hexanethio-4-[5-aminobenzimidazol-1-yl]pyrimidine and 2-hexanethio-4-[6-aminobenzimidazol-1-yl]pyrimidine To a stirred solution of 5-aminobenzimidazole (2.15 g) in DMF (40 mL) at 0° C. under $N_2$ was added NaH (in three portions totalling 645 mg of a 60% dispersion in oil). After 15 min the cooling bath was removed and the mixture stirred. After an additional 15 min the benzimidazole sodium salt solution was added to a solution of 4-chloro-2-hexanethiopyrimidine (3.1 g) in DMF (40 mL) via syringe. The resulting mixture was stirred overnight under $N_2$. The DMF was removed under reduced pressure. The residue was diluted with $CH_2Cl_2$ and washed with water. The aqueous layer was back extracted with $CH_2Cl_2$. The organic extracts were combined, dried over anhydrous $Na_2SO_4$, filtered and concentrated. The residue was purified by column chromatography on silica gel (eluted with 1.75%MeOH in $CH_2Cl_2$) affording the title compounds. 2-hexanethio-4-[6-aminobenzimidazol-1-yl]pyrimidine (faster regioisomer): $^1$H NMR (500 MHz, $CD_3OD$): δ8.66 (1H, s); 8.58 (1H, d, J=5.5 Hz); 7.63 (1H, d, J=2 Hz); 7.45 (2H, m); 6.82 (1H, dd, J=8.5 Hz, J=2 Hz); 3.25 (2H, t, J=7.5 Hz); 1.78 (2H, m); 1.50 (2H, m); 1.33 (4H, m); 0.89 (3H, t, J=7 Hz). 2-hexanethio-4-[5-aminobenzimidazol-1-yl]pyrimidine (slower regioisomer): $^1$H NMR (500 MHz, $CD_3OD$): δ8.80(1H, s); 8.55 (1H, d, J=5.5 Hz); 8.09 (1H, d, J=8.5 Hz); 7.46 (1H, d, J=5.5 Hz); 7.05 (1H, d, J=2 Hz); 6.86 (1H, dd, J=8.5 Hz, J=2 Hz); 3.22 (2H, t, J=7.5 Hz); 1.78 (2H, m); 1.50 (2H, m); 1.34 (4H, m); 0.90 (3H, t, J=7 Hz).

EXAMPLE 5

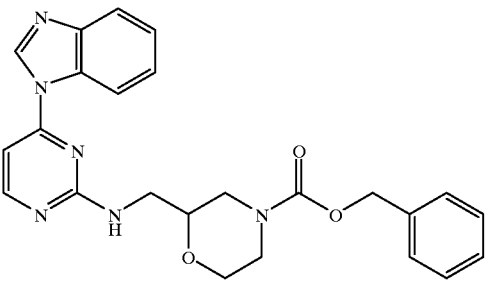

2-[(1-(Benzyloxycarbonyl)morpholin-2-yl)-methylamino]-4-[benzimidazol-1-yl 3-pyrimidine Step A: Methyl 4-fluorenyloxycarbonyl-morpholine-2-carboxylate To a solution of 3.00 g of 4-fluorenyloxycarbonylmorpholine-2-carboxylic acid in 150 mL of acetone was added 1.77 g of potassium carbonate and 1.33 g of dimethyl sulfate. The mixture was heated to reflux and stirred at this temperature for 6 h, then cooled, filtered, and concentrated. The residue was dissolved in 125 mL of $Et_2O$ and washed with 50 mL each of saturated $NaHCO_3$, water, and brine. The organic phase was dried over $MgSO_4$ and concentrated to yield 3.10 g of the title compound, which was used without further purification. $^1$H NMR (500 MHz, $CDCl_3$): δ7.76 (d, J=7.6 Hz, 2H), 7.57 (br d, J=6.6 Hz, 2H), 7.40 (t, J=7.3 Hz, 2H), 7.32 (t, J=7.6 Hz, 2H), 4.51 (br s, 2H), 4.25 (br t, J=6.2 Hz, 1H), 3.90–4.10 (m, 4H), 3.80 (s, 3H), 3.40–3.70 (m, 1H), 3.04–3.23 (m, 2H).

Step B: 2-Hydroxymethyl-4-fluorenyloxycarbonyl-morpholine

To a solution of 3.56 g of methyl 4-fluorenyloxycarbonyl-morpholine-2-carboxylate in 25 mL of THF was added 0.58 g of lithium chloride, 0.52 g of sodium borohydride, and 25 mL of ethanol. The mixture was stirred overnight at room temperature, concentrated, and redissolved in 200 mL of $CH_2Cl_2$. This $CH_2Cl_2$ solution was washed with 2×100 mL of water and 100 mL of brine, dried over $MgSO_4$, and concentrated. The residue was purified by flash chromatography, eluting with 1:1 hexanes-EtOAc, to yield 2.34 of the title compound as a colorless oil. $^1$H NMR (500 MHz, $CDCl_3$): δ7.77 (d, J=7.6 Hz, 2H), 7.56 (d, J=7.3 Hz, 2H), 7.40 (t, J=7.6 Hz, 2H), 7.32 (t, J=7.3 Hz, 2H), 4.49 (br s, 2H), 4.24 (t, J=6.4 Hz, 1H), 3.24–4.03 (m, 7H), 2.97 (br s, 1H), 2.80 (br t, J=11.7 Hz, 1H).

Step C: 2-Hydroxymethyl-4-benzyloxycarbonyl-morpholine

To a solution of 2.20 g of 2-hydroxymethyl-4-fluorenyloxycarbonyl-morpholine in 25 mL of $CH_2Cl_2$ was added 1.29 g of piperidine. The mixture was stirred at room temperature for 2 days. Diisopropylethylamine (7.15 g) and 6.30 g of benzyl chloroformate were added and the mixture was stirred overnight at room temperature, then diluted with 100 mL of EtOAc and washed with 50 mL each of 1N HCl, saturated $NaHCO_3$, and brine, dried over $MgSO_4$, and concentrated. The residue was purified by flash chromatography, eluting with a gradient system of 20:1 $CH_2Cl_2$-acetone to 9:1 $CH_2Cl_2$-acetone, to yield 638 mg of the title compound. $^1$H NMR (500 MHz, $CDCl_3$): δ7.30–7.40 (m, 5H), 5.15 (ABq, J=12.4 Hz, 2H), 3.93 (br s, 3H), 3.68 (br s, 1H), 3.47–3.63 (m, 3H), 3.02 (br s, 1H), 2.85 (br s, 1H), 1.90 (br s, 0.6H). IR (neat) 3427, 2862, 1693, 1432, 1354, 1236, 1129 $cm^{-1}$.

Step D: 2-Aminomethyl-4-benzyloxycarbonyl-morpholine

To a 0° C. solution of 668 mg of 2-hydroxymethyl-4-benzyloxy-carbonylmorpholine in 10 mL of $CH_2Cl_2$ was added 515 mg of diisopropylethylamine, then 365 mg of methanesulfonyl chloride. The mixture was allowed to warm to room temperature over 2 h, then diluted with 50 mL of EtOAc and washed with 25 mL of saturated $NaHCO_3$, 2×25 mL of 1N HCl, 25 mL of saturated $NaHCO_3$, and 25 mL of brine. The organic phase was dried over $MgSO_4$ and concentrated to a yellow oil. This oil was dissolved in 10 mL of DMF and 260 mg of sodium azide was added. The mixture was heated to 100° C. and stirred for 5 h at this temperature, then cooled, diluted with 50 mL of EtOAc, and washed with 3×25 mL of water and 25 ml of brine. The organic phase was dried over $MgSO_4$ and concentrated to a yellow oil. This oil was dissolved in 10 mL of 9:1 THF-water and 837 mg of triphenylphosphine was added. The mixture was heated to 50° C. and stirred at this temperature for 15 h, then cooled, poured into 50 mL of 1N HCl, and extracted with 2×10 mL of EtOAc. The aqueous phase was made very basic (pH>12) by addition of 5 N NaOH, then extracted with 5×25 mL of EtOAc. The combined organic extracts were washed with 10 mL of brine, dried over $MgSO_4$, and concentrated. The residue was purified by flash chromatography, eluting with 95:5 $CH_2Cl_2$-2M $NH_3$ in MeOH, to yield 519 mg of the title compound as a colorless oil. 1H NMR (500 MHz, DMSO-d6, 75° C.): δ7.27–7.40 (m, 5H), 5.10 (ABq, J=12.8 Hz, 2H), 3.91 (d, J=13.0 Hz, 1H), 3.73–3.85 (m, 2H), 3.41 (dt, J=2.1, 11.7 Hz, 1H), 2.88–3.30 (m, 4H), 2.94 (br t, J=11.9 Hz, 1H), 2.68 (br t, J=12.1 Hz, 1H), 2.52–2.65 (m, 2H), 1.32 (br s, 1.5H).

Step E: 2-[(1-(Benzyloxycarbonyl)morpholin-2-yl)methylamino]-4-[benzimidazol-1-yl]pyrimidine To a solution of 200 mg of 2-methanesulfonyl-4-[benzimidazol-1-yl]pyrimidine (EXAMPLE 1 Step B) in 3 mL of DMF was added a solution of 230 mg of 2-aminomethyl-4-benzyloxycarbonyl-morpholine in 3 mL of toluene. The mixture was heated to 100° C. and stirred at this temperature for 16 h, then cooled, diluted with 50 mL of EtOAc, and washed with 4×20 mL of water and 25 ml of brine. The organic phase was dried over $MgSO_4$ and concentrated. The residue was purified by flash chromatography, eluting with a gradient system of 9:1 $CH_2Cl_2$-acetone to 4:1 $CH_2Cl_2$-acetone, to yield 142 mg of the title compound. $^1$H NMR (500 MHz, $CDCl_3$): δ8.61 (s, 1H), 8.39 (d, J=5.3 Hz, 1H) 8.17 (d, J=8.5 Hz, 1H), 7.86 (d, J=8.7 Hz, 1H), 7.29–7.45 (m, 5H), 6.82 (d, J=5.5 Hz, 1H), 5.75 (br s, 1H), 5.14 (ABq, J=12.1 Hz, 2H), 3.84–4.22 (m, 3H), 3.40–3.80 (m, 4H), 3.06 (br s, 1H) 2.88 (br, s, 1H). Mass spectrum (ESI) 445.2 (M+1).

EXAMPLE 6

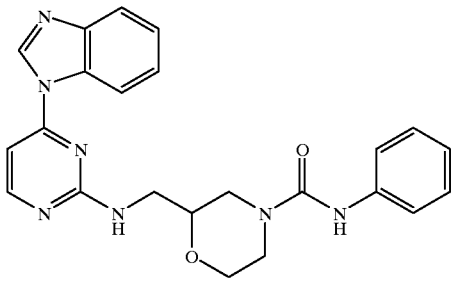

2-[(1-(N-Phenylcarbamoyl)morpholin-2-yl)-methylamino]-4-[benzimidazol-1-yl]-pyrimidine Step A: 2-[(Morpholin-2-yl)-methylamino]-4-[benzimidazol-1-yl]pyrimidine To a 0° C. solution of 150 mg of 2-[(1-(benzyloxy-carbonyl)morpholin-2-yl)-methylamino]-4-[benzimidazol-1-yl]pyrimidine (from EXAMPLE 5, step E) in 3 mL of $CH_2Cl_2$ was added 1 mL of 30% HBr in acetic acid. The cooling bath was removed after 20 min and the mixture was stirred at room temperature for 1 h, then diluted with 20 mL of water and extracted with 2×10 mL of $CH_2Cl_2$. The pH of the aqueous phase was adjusted to 11 with 5N NaOH, and the aqueous phase was extracted with 5×10 mL of EtOAc, with continuous monitoring of the pH. The combined EtOAc extracts were dried over $MgSO_4$ and concentrated to yield 80 mg of the title compound as an off-white solid. $^1$H NMR (500 MHz, $CDCl_3$): δ8.60 (s, 1H), 8.36 (d, J=5.3 Hz, 1H) 8.15 (d, J=7.6 Hz, 1H), 7.82 (d, J=7.6 Hz, 1H), 7.31–7.40 (m, 2H), 6.76 (dd, J=0.9, 5.5 Hz, 1H), 5.90 (br s, 1H), 3.90 (br d, J=11.2 Hz, 1H), 3.57–3.76 (m, 3H), 3.45 (br s, 1H), 2.97 (d, J=1.4 Hz, 1H) 2.76–2.94 (m, 2H), 2.69 (t, J=10.8 Hz, 1H).

Step B: 2-[(1-(N-Phenylcarbamoyl)morpholin-2-yl)-methylamino]-4-[benzimidazol-1-yl]pyrimidine To a solution of 20 mg of 2-[(morpholin-2-yl)-methylamino]-4-[benzimidazol-1-yl]pyrimidine in 0.5 mL of $CH_2Cl_2$ was added 7.7 mg of phenyl isocyanate. The mixture was stirred at room temperature overnight, then added directly to a silica gel column and purified by flash chromatography, eluting with a gradient system of 2:1 $CH_2Cl_2$-acetone to 1:1 $CH_2Cl_2$-acetone, to yield 26 mg of the title compound. $^1$H NMR (500 MHz, $CDCl_3$): δ8.61 (s, 1H), 8.39 (d, J=5.3 Hz, 1H) 8.17 (d, J=7.6 Hz, 1H), 7.85 (d, J=7.3 Hz, 1H), 7.22–7.45 (m, 5H), 7.03 (t, J=7.3 Hz, 1H), 6.81 (d, J=5.5 Hz, 1H), 6.51 (s, 1H), 5.75 (br s, 1H), 3.97–4.09 (m, 2H), 3.73–3.88 (m, 3H), 3.54–3.70 (m, 2H), 3.12 (dt, J=3.9, 13.1 Hz, 1H), 2.92 (dd, J=10.5, 12.8 Hz, 1H), 1.90 (br s, 0.6H). Mass spectrum (ESI) 430.6 (M+1).

EXAMPLE 7

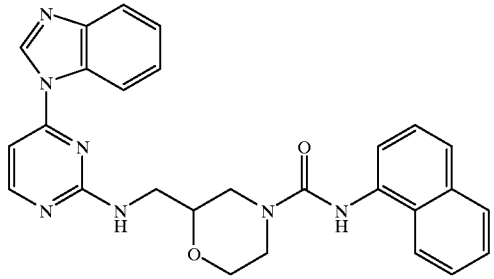

2-[(1-(N-Naphth-1-yl-carbamoyl)morpholin-2-yl)-methylamino]-4-[benzimidazol-1-yl]pyrimidine To a solution of 20 mg of 2-[(morpholin-2-yl)-methylamino]-4-[benzimidazol-1-yl]pyrimidine (from EXAMPLE 6, step A) in 0.5 mL of $CH_2Cl_2$ was added 11.8 mg of naphthyl isocyanate. The mixture was stirred at room temperature overnight, then added directly to a silica gel column and purified by flash chromatography, eluting with a gradient system of 2:1 $CH_2Cl_2$-acetone to 1:1 $CH_2Cl_2$-acetone, to yield 29 mg of the title compound. $^1$H NMR (500 MHz, $CDCl_3$): δ8.61 (s, 1H), 8.39 (d, J=5.3 Hz, 1H) 8.17 (d, J=8.2 Hz, 1H), 7.78–7.85 (m, 3H), 7.66 (d, J=8.2 Hz, 1H), 7.60 (d, J=7.3 Hz, 1H), 7.33–7.51 (m, 4H), 6.81 (d, J=5.5 Hz, 1H), 6.69 (s, 1H), 5.65 (br s, 1H), 4.08 (d, J=12.6 Hz, 1H), 4.02 (dd, J=2.0, 11.7 Hz, 1H), 3.87 (d, J=12.8 Hz, 1H), 3.73–3.84 (m, 2H), 3.69 (dt, J=2.8, 11.7 Hz, 1H), 3.54–3.64

(m, 1H), 3.20 (dt, J=3.2, 12.6 Hz, 1H), 2.98 (dd, J=10.5, 12.8 Hz, 1H). Mass spectrum (ESI) 480.6 (M+1).

EXAMPLE 8

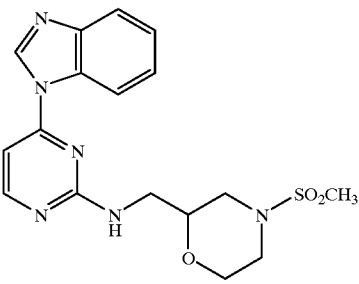

2-[(1-Methanesulfonylmorpholin-2-yl)-methylamino]-4-[benzimidazol-1-yl]-pyrimidine To a 0° C. solution of 20 mg of 2-[(morpholin-2-yl)-methylamino]-4-[benzimidazol-1-yl]pyrimidine (from EXAMPLE 6, step A) in 0.5 mL of CH$_2$Cl$_2$ was added 7.4 mg of diisopropylethylamine, then 9.6 mg of methanesulfonyl chloride. The mixture was allowed to warm to room temperature overnight, then added directly to a silica gel column and purified by flash chromatography, eluting with a gradient system of 4:1 CH$_2$Cl$_2$-acetone to 2:1 CH$_2$Cl$_2$-acetone, to yield 19 mg of the title compound. $^1$H NMR (500 MHz, CDCl$_3$): δ8.61 (s, 1H), 8.41 (d, J=5.5 Hz, 1H) 8.17 (d, J=8.0 Hz, 1H), 7.86 (d, J=7.8 Hz, 1H), 7.35–7.45 (m, 2H), 6.84 (d, J=5.5 Hz, 1H), 4.06 (ddd, J=1.4, 3.2, 11.7 Hz, 1H), 3.85 (br s, 1H), 3.69–3.81 (m, 3H), 3.65–3,54 (m, 2H), 2.88 (dt, J=3.4, 10.3 Hz, 1H), 2.79 (s, 3H), 2.69 (br t, J=11.0 Hz, 1H). Mass spectrum (ESI) 489.5 (M+1).

EXAMPLE 9

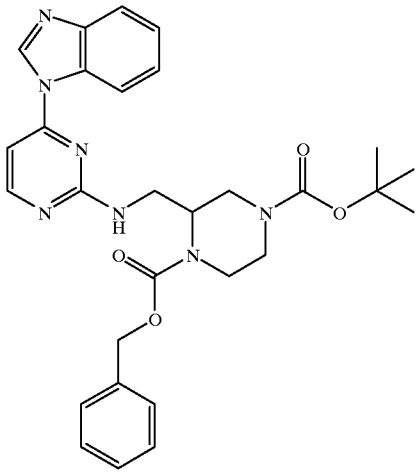

2-[(1-(Benzyoxycarbonyl)-4-(tert-butyloxycarbonyl)-piperazin-2-yi)-methylamino]-4-[benzimidazol-1-yl]pyrimidine Step A: 1-(Benzyloxycarbonyl)-2-hydroxymethyl-4-(tert-butyloxycarbonyl)-piperazine To a solution of 3.00 g of piperazine-2-carboxylic acid in 100 mL of 1:1 dioxane-water at pH 11 was added dropwise a solution of 4.0 g of 2-(tert-butoxycarbonyloxyimino)-2-phenylacetonitrile in 25 nL of dioxane, maintaining the pH of the solution at 11 during the addition with the use of 5N NaOH. The mixture was stirred for 6 h at room temperature, then cooled to 0° C. The pH was adjusted to 9.5 with the use of 1N HCl. Benzyl chloroformate (2.8 g) was added dropwise, maintaining the pH of the solution at 9.5 during the addition with the use of 5N NaOH. The mixture was allowed to warm to room temperature and stirred for 20 h, then extracted with 2×75 mL of Et$_2$O, acidified to pH≦2 with 1N HCl, and extracted with 4×50 mL of EtOAc. The combined EtOAc extracts were washed with 50 mL of brine, dried over MgSO$_4$, and concentrated to a pale yellow oil. This oil was dissolved in 150 mL of acetone. Dimethyl sulfate (2.25 g) and potassium carbonate (2.89 g) were added. The mixture was heated to reflux and stirred at this temperature for 6 h, then cooled, filtered, and concentrated. The residue was dissolved in 125 mL of Et$_2$O and washed with 50 mL each of saturated NaHCO$_3$, water, and brine. The organic phase was dried over MgSO$_4$ and concentrated to yield 6.06 g of the methyl ester. This methyl ester (5.32 g) was dissolved in 30 mL of THF and 834 mg of lithium chloride, 744 mg of sodium borohydride, and 30 mL of ethanol were added. The mixture was stirred overnight at room temperature, concentrated, and redissolved in 200 mL of CH$_2$Cl$_2$. This CH$_2$Cl$_2$ solution was washed with 100 mL of water and 100 mL of brine, dried over MgSO$_4$, and concentrated. The residue was purified by flash chromatography, eluting with a gradient system of 2:1 hexanes-EtOAc to 1:1 hexanes-EtOAc, to yield 2.65 g of the title compound as a colorless oil. $^1$H NMR (500 MHz, CDCl$_3$): δ7.30–7.40 (m, 5H), 5.15 (ABq, J=12.4 Hz, 2H), 3.80–4.34 (m, 4H), 3.48–3.75 (m, 2H), 2.80–3.20 (m, 3H), 1.47 (br s, 9H).

Step B: 1-(Benzyloxycarbonyl )-2-aminomethyl-4-(tert-butyloxycarbonyl)-piperazine To a 0° C. solution of 1.30 g of 1-(benzyloxycarbonyl)-2-hydroxymethyl-4-(tert-butyloxycarbonyl)-piperazine in 20 mL of CH$_2$Cl$_2$ was added 720 mg of diisopropylethylamine, then 510 mg of methanesulfonyl chloride. The mixture was allowed to warm to room temperature over 2 h, then diluted with 50 mL of EtOAc and washed with 25 mL of saturated NaHCO$_3$, 2×25 mL of 1N HCl, 25 mL of saturated NaHCO$_3$, and 25 mL of brine. The organic phase was dried over MgSO$_4$ and concentrated to a yellow oil. This oil was dissolved in 10 mL of DMF and 360 mg of sodium azide was added. The mixture was heated to 100° C. and stirred overnight at this temperature, then cooled, diluted with 25 mL of EtOAc, and washed with 3×10 mL of water and 10 ml of brine. The organic phase was dried over MgSO$_4$ and concentrated to an oily yellow solid. Of this solid, 475 mg was dissolved in 5 mL of 9:1 THF-water and 398 mg of triphenylphosphine was added. The mixture was heated to 50° C. and stirred at this temperature for 16 h, then cooled, poured into 30 mL of 1N HCl, and extracted with 2×10 mL of EtOAc. The aqueous phase was made very basic (pH>12) by addition of 5N NaOH, then extracted with 5×20 mL of EtOAc. The combined organic extracts were dried over MgSO$_4$, and concentrated to yield 48 mg of the title compound. $^1$H NMR (500 MHz, CDCl$_3$): δ7.28–7.40 (m, 5H), 5.15 (ABq, J=12.4 Hz, 2H), 3.82–4.22 (m, 4H), 2.66–3.30 (m, 5H), 1.45 (br s, 9H).

Step C: 2-[(1-(Benzyloxycarbonyl)-4-(tert-butyloxycarbonyl) piperazin-2-yl)-methylamino]-4-[benzimidazol-1-yl]pyrimidine To a solution of 34 mg of 2-methanesulfonyl-4-[benzimidazol-1-yl]pyrimidine (EXAMPLE 1 Step B) in 0.75 mL of DMF was added a solution of 48 mg of 1-(benzyloxycarbonyl)-2-aminomethyl-4-(tertbutyloxycarbonyl)piperazine in 3 mL of toluene. The mixture was heated to 100° C. and stirred at this temperature for 6 h, then cooled, diluted with 20 mL of EtOAc, and washed with 4×10 mL of water and 10 ml of brine. The organic phase was dried over MgSO$_4$ and concentrated. The residue was purified by flash chromatography, eluting with a gradient system of 9:1 CH$_2$Cl$_2$-acetone to 4:1 CH$_2$Cl$_2$-acetone, to yield 27 mg of the title compound. R$_f$: 0.33 (4:1 hexanes-acetone). $^1$H NMR (500 MHz, DMSO-d6, 75° C.): δ8.93 (s, 1H), 8.43 (br s, 1H), 8.35 (d, J=5.5 Hz, 1H), 7.75 (dd, J=2.1, 7.1 Hz, 1H), 7.30–7.40 (m, 3H), 7.06 (d, J=5.5 Hz, 1H), 5.01 (d, J=12.6 Hz, 1H), 4.88 (br s, 1H), 4.54 (br s, 1H), 3.98 (d, J=13.7 Hz, 1H), 3.84–3.94 (m, 2H), 3.58–3.66 (m, 1H), 3.46–3.54 (m, 1H), 3.18–3.26 (m, 1H), 3.02–3.10 (m, 1H), 2.80–2.89 (m, 1H), 1.39 (m, 9H). Mass spectrum (ESI) 544.3 (M+1).

EXAMPLE 10

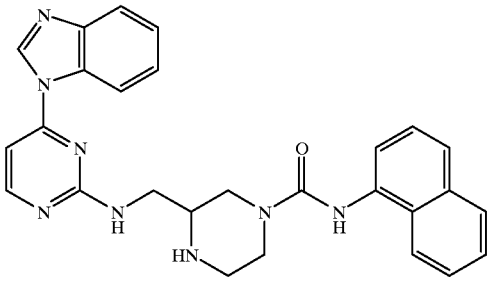

2-[1(4-(N-Naphth-1-yl-carbamoyl)piperazine-2-yl)-methylamino]-4-[benzimidazol-1-yl]pyrimidine Step A: 2-[(1-(Benzyloxycarbonyl)-4-(N-naphth-1-yl-carbamoyl)-piperazine-2-yl)-methyylamino]-4-[benzimidazol-1-yl]pyrmidine To a solution of 65 mg of 2-[(1-(benzyloxycarbonyl)4-(tert-butyloxycarbony)-piperazin-2-yl)-methylamino]-4-[benzimidazol-1-yl]pyrimidine (from EXAMPLE 9, step C) in 1 mL of CH$_2$Cl$_2$ was added 1 mL of trifluoroacetic acid. The mixture was stirred at room temperature for 1 h, then concentrated and redissolved in 1 mL of pyridine. Naphthyl isocyanate (24 mg) was added, and the mixture was stirred at room temperature for 2 h, then diluted with 30 mL of CH$_2$C$_2$ and washed with 2×10 mL of 1M NaHSO$_4$ and 10 mL of saturated NaHCO$_3$. The organic phase was dried over MgSO$_4$, concentrated, and purified by preparative thin layer chromatography, eluting with 2:1 CH$_2$Cl$_2$-acetone, to yield 40.7 mg of the title compound. R$_f$: 0.49 (10% 2M NH$_3$—MeOH in CH$_2$Cl$_2$). $^1$H NMR (500 MHz, CDCl$_3$): δ 8.55 (br s, 1H), 7.96–8.16 (m, 3H), 7.76–7.93 (m, 3H), 7.59–7.73 (m, 2H), 7.20–7.54 (m, 9H), 6.62 (br s, 1H), 5.18 (br s, 2H), 4.54 (br s, 1H), 3.56–4.42 (m, 5H), 2.92–3.45 (m, 3H).

Step B: 2-[(4-(N-Naphth-1-yl-carbamoyl)piperazine-2-yl) methylamino]-4-[benzimidazol-1-yl]pyrimidine To a 0° C. solution of 38 mg of 2-[(1-(benzyloxycarbonyl)-4-(N-naphth-1-yl-carbamoyl) piperazine-2-yl)-methylamino]-4-[benzimidazol-1-yl] pyrimidine in 1 mL of CH$_2$Cl$_2$ was added 0.3 mL of 30% HBr in acetic acid. The cooling bath was removed after 20 min and the mixture was stirred at room temperature for 1 h, then diluted with 15 mL of water and extracted with 2×5 mL of CH$_2$Cl$_2$. The pH of the aqueous phase was adjusted to 11 with 5N NaOH and the aqueous phase was extracted with 5×10 mL of EtOAc, with continuous monitoring of the pH. The combined EtOAc extracts were dried over MgSO$_4$ and concentrated to yield 22 mg of the title compound as a white solid. This solid could be further purified by preparative thin layer chromatography, eluting with 9:1 CH$_2$Cl$_2$-2M NH$_3$ in MeOH. R$_f$: 0.34 (10% 2M NH$_3$—MeOH in CH$_2$Cl$_2$). $^1$H NMR (500 MHz, CD$_3$OD): δ 8.89 (s, 1H), 8.43 (br s, 1H), 8.36 (d, J=5.3 Hz, 1H), 7.89 (br s, 1H), 7.82 (d, J=9.2 Hz, 1H), 7.70 (dd, J=3.2, 8.2 Hz, 2H), 7.28–7.45 (m, 5H), 7.02 (d, J=5.5 Hz, 1H), 4.24 (br d, J=12.1 Hz, 1H), 4.06 (br d, J=13.3 Hz, 1H), 3.50–3.62 (m, 2H), 3.04–3.18 (m, 3 H), 2.82–2.94 (m, 2H).

EXAMPLE 11

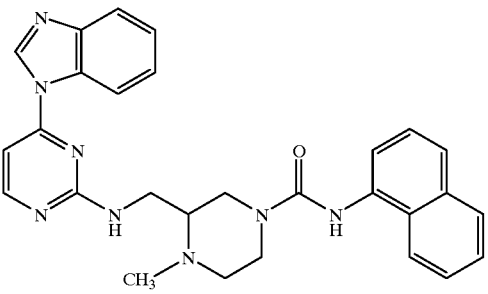

2-[(1-Methyl-4-(N-naphth-1-yl -carbamoyl)piperazine-2-yl) methylamino]-4-benzimidazol-1-yl]pyrimidine To a solution of 10 mg of 2-[(4-(N-naphth-1-yl-carbamoyl)piperazine-2-yl)-methylamino]-4-[benzimidazol-1-yl]pyrimidine (from EXAMPLE 10, step B) in 0.5 mL of 1:1 CH$_3$CN—MeOH was added 10 μL of a 37% aqueous solution of formaldehyde. After stirring 15 min at room temperature, 2 mg of sodium cyanoborohydride was added and the mixture was stirred for 16 h at room temperature, then diluted with 5 mL of EtOAc and poured into 15 mL of 1N HCl. The phases were separated and the aqueous phase was extracted with 5 mL of EtOAc. The aqueous phase was made very basic (pH>10) by addition of 5N NaOH, then extracted with 5×10 mL of EtOAc. The combined organic extracts were washed with 10 mL of brine, dried over MgSO$_4$, and concentrated. The residue was purified by preparative thin layer chromatography, eluting with 20:1 CH$_2$C$_2$—MeOH, to yield 9.2 mg of the title compound as an off-white solid. $^1$H NMR (500 MHz, CDCl$_3$): δ8.62 (s, 1H), 8.36 (d, J=5.5 Hz, 1H), 8.17 (br d, J=7.6 Hz, 1H), 7.81–7.88 (m, 2H), 7.66 (d, J=8.0 Hz, 1H), 7.60 (br d, J=7.3 Hz, 1H), 7.35–7.49 (m, 4H), 6.90 (br s, 1H), 6.78 (d, J=5.5 Hz, 1H), 6.00 (br s, 1H), 3.99 (br d, J=11.9 Hz, 1H), 3.87 (br d, J=12.6 Hz, 1H), 3.76–3.84 (m, 1H), 3.29 (br s, 2H), 2.88 (dt, J=3.2, 11.9 Hz, 1H), 2.34–2.60 (m, 5H).

EXAMPLE 12

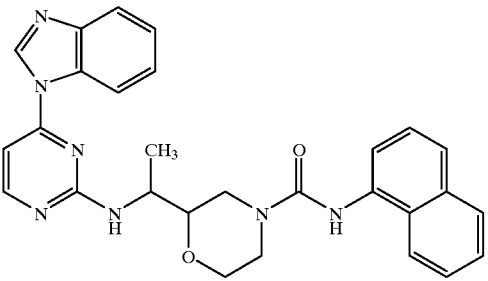

2-[1-(4-(N-Naphth-1-yl-carbamoyl)morpholine-2-yl) ethylamino]-4-[benzimidazol-1-yl]pyrimidine, diastereomer 1

Step A: 4-Fluorenyloxycarbonylmorpholine-2-(N-methyl-N-methoxy)-carboxamide

To a solution of 5.00 g of 4-fluorenyloxycarbonylmorpholine-2-carboxylic acid in 150 mL of CH$_2$Cl$_2$ were added sequentially 1.52 g of N,O-dimethylhydroxylamine, 3.00 g of 1-(3-dimethylaminopropyl)-3-ethylcarbodiimide hydrochloride, 4.31 g of triethylamine, and 350 mg of dimethylaminopyridine. The mixture stirred overnight at room temperature, poured into 200 mL of water. The phases were separated and the aqueous phase was extracted with 100 mL of CH$_2$Cl$_2$. The combined organics were washed with 100 mL each of 1N HCl, water, and brine, dried over Na$_2$SO$_4$, and concentrated to yield 5.57 g of the title compound as a pale yellow foam, which was used without further purification. $^1$H NMR (500 MHz, DMSO-d6): δ7.87 (d, J=7.6 Hz, 2H), 7.62 (d, J=7.3 Hz, 2H), 7.40 (app t, J=7.6 Hz, 2H), 7.33 (dd, J=7.3, 7.3 Hz, 2H), 412–4.52 (m, 4H), 3.38–3.94 (m, 7H), 3.11 (br s, 3H), 2.99 (br s, 2H).

Step B: 4-Benzyloxycarbonyl-morpholine-2-(N-methyl-N-methoxy)-carboxamide

To a solution of 4.70 g of 4-fluorenyloxycarbonylmorpholine-2-(N-methyl-N-methoxy)carboxamide in 100 mL of DMF was added 4.72 g of potassium fluoride, 2.58 g of triethylamine, and 4.00 g of N-benzyloxycarbonyloxy-5-norbornene-2,3-dicarboxamide. The mixture was stirred overnight at room temperature, then diluted with 400 mL EtOAc and poured into 400 mL of water. The phases were separated and the organic phase was extracted with 100 mL each of 1 N HCl, water, and brine, dried over Na$_2$SO$_4$, and concentrated. The residue was purified by flash chromatography, eluting with a gradient system of 2:1 hexanes-EtOAc to 1:1 hexanes-EtOAc, to yield 1.39 g of the title compound as a colorless oil. $^1$H NMR (500 MHz, CDCl$_3$): δ7.29–7.39 ((m, 4H), 5.16 (AB q, J=12.4 Hz, 2H), 3.84–4.46 (m, 4H), 3.54–3.81 (m, 4H), 3.02–3.28 (s, 5H).

Step C: 2-Acetyl-4-benzyoxycarbonyl-morpholine

To a solution of 2.06 g of 4-benzyl oxycarbonyl-morpholine-2-(N-methyl-N-methoxy)carboxamide in 50 nL of THF at 0° C. was added 14 mL of a 1.4M solution of methylmagnesium bromide in toluene. The cooling bath was removed after 15 min and the mixture was stirred at room temperature for 1 h. The reaction was quenched by addition of ca. 25 mL of saturated NH$_4$Cl and the mixture was stirred vigorously for 15 min at room temperature, then diluted with 74 mL of water and 50 mL of Et$_2$O. The phases were separated and the aqueous phase was extracted with 2×50 mL of Et$_2$O. The combined organics were washed with 50 mL of brine, dried over Na$_2$SO$_4$, and concentrated to yield 1.38 g of a yellow liquid that was used without further purification. $^1$H NMR (500 MHz, CDCl$_3$): δ7.28–7.42 (m, 4H), 5.15 (AB q, J=12.4 Hz , 2H), 4.24 (br s, 1H), 3.78–4.05 (m, 3H), 3.51–3.66 (m, 1H), 2.96–3.13 (m, 1H), 2.81–2.96 (m, 2H), 2.23 (s, 3H).

Step D: 2-(1-Hydroxyethyl)-4-benzyloxycarbonylmorpholine

To a solution of 1.38 of 2-acetyl-4-benzyloxycarbonylmorpholine in 50 mL of 1:1 THF-EtOH was added 400 mg of sodium borohydride, in several portions. The mixture was stirred at room temperature for 2 h, then quenched by addition of 25 mL of saturated NaHCO$_3$. The mixture was diluted with 75 mL of water and 25 mL of EtOAc. The phases were separated and the aqueous phase was extracted with 2×25 mL of EtOAc. The combined organics were washed with 25 mL of brine, dried over Na$_2$SO$_4$, and concentrated. The residue was purified by flash chromatography, eluting with 2:1 hexanes-EtOAc, to yield 383 mg of diastereomer 1, 341 mg of diastereomer 2, and 436 mg of a mixture of the two isomers. Data for diastereomer 1. R$_f$ 0.35 (1:1 hexanes-EtOAc) $^1$H NMR (500 MHz, CDCl$_3$): δ7.30–7.43 (m, 4H), 5.12–5.23 (m, 2H), 3.80–4.18 (m, 4H), 3.57 (br t, J=11.0Hz, 1H), 3.32 (br s, 1H), 2.84–3.11 (m, 2H), 2.05 (br s, 1H),1.22 (d, J=6.5 Hz, 3H). Data for diastereomer 2. R$_f$ 0.28 (1:1 hexanes-EtOAc).

Step E: 2-(1-Aminoethyl)-4-benzyloxycarbonylmorpholine, diastereomer 1

To a 0° C. solution of 100 mg of 2-(1-hydroxyethyl)-4-benzyloxy-carbonylmorpholine, diastereomer 1, in 4 mL of CH$_2$Cl$_2$ was added 73 mg of diisopropylethylamine, then 52 mg of methanesulfonyl chloride. The mixture was allowed to warm to room temperature over 2 h, then diluted with 20 mL of EtOAc and washed with 10 mL of saturated NaHCO$_3$, 2×10 mL of 1N HCl, 10 mL of saturated NaHCO$_3$, and 10 mL of brine. The organic phase was dried over Na2SO$_4$ and concentrated. The residue was dissolved in 3 mL of DMF and 124 mg of sodium azide was added. The mixture was heated to 125° C. and stirred for 2 h at this temperature, then cooled, diluted with 20 mL of EtOAc, and washed with 3×10 mL of water and 10 ml of brine. The organic phase was dried over Na$_2$SO$_4$ and concentrated. The residue was dissolved in 3 mL of 9:1 THF-water and 270 mg of triphenylphosphine was added. The mixture was heated to 75° C. and stirred at this temperature overnight, then cooled, poured into 25 mL of 1N HCl, and extracted with 2×10 mL of EtOAc. The aqueous phase was made very basic (pH>12) by addition of 5N NaOH, then extracted with 5×10 mL of EtOAc. The combined organic extracts were washed with 10 mL of brine, dried over Na$_2$SO$_4$, and concentrated to yield 46 mg of the title compound, which was used without further purification. $^1$H NMR (500 MHz, CDCl$_3$): δ7.28–7.40 (m, 4H), 5.15 (br s, 2H), 3.82–4.14 (m, 3H), 3.51 (br s, 1H), 3.08 (br t, J=8.0 Hz, 1H), 2.60–3.02 (m, 3H), 1.10 (d, J=6.5 Hz, 3H).

Step F: 2-[1-(4-(Benzyloxycarbonyl)morpholine-2-yl)ethylamino]-4-[benzimidazol-1-yl]pyrimidine, diastereomer 1

To a solution of 62 mg of 2-methanesulfonyl-4-[benzimidazol-1-yl]pyrimidine (EXAMPLE 1 Step B) in 1 mL of DMF was added a solution of 40 mg of 2-(1-aminoethyl)-4-benzyloxycarbonyl-morpholine, diastereomer 1, in 1 mL of toluene. The mixture was heated to 100° C. and stirred at this temperature for 16 h, then cooled, diluted with 10 mL of EtOAc, and washed with 4×5 mL of water and 5 ml of brine. The organic phase was dried over Na$_2$SO$_4$ and concentrated. The residue was purified by flash chromatography, eluting with a gradient system of 1:1 hexanes-acetone to 1:2 hexanes-acetone, to yield 24 mg of the title compound. $^1$H NMR (500 MHz, CDCl$_3$): δ8.61 (s, 1H), 8.37 (d, J=4.8 Hz, 1H), 8.15 (d, J=8.2 Hz, 1H), 7.86 (d, J=8.7 Hz, 1H), 7.28–7.43 (m, 5H), 6.81 (d, J=5.5 Hz, 1H), 5.08–5.18 (m, 2H), 4.29 (br s, 1H), 3.84–4.18 (m, 3H), 3.45–3.62 (m, 2H) 3.01 (br s, 2H), 1.37 (d, J=6.5 Hz, 3H).

Step G: 2-[1-(4-(N-Naphth-1-yl-carbamoyl)morpholine-2-yl)ethylamino]-4-[benzimidazol-1-yl]pyrimidine, diastereomer 1

To a 0° C. solution of 24 mg of 2-[1-(4-(benzyloxycarbonyl)morpholine-2-yl)ethylamino]-4-[benzimidazol-1-yl]pyrimidine, diastereomer 1, in 1 mL of CH$_2$Cl$_2$ was added 0.3 mL of 30% HBr in acetic acid. The cooling bath was removed after 10 min and the mixture was stirred at room temperature for 30 min, then diluted with 10 mL of water and extracted with 2×5 mL of CH$_2$Cl$_2$. The pH of the aqueous phase was adjusted to 11 with 5N NaOH, and the aqueous phase was extracted with 5×5 mL of EtOAc, with continuous monitoring of the pH. The combined EtOAc extracts were dried over Na$_2$SO$_4$ and concentrated. The residue was dissolved in 1 mL of CH$_2$Cl$_2$ and 9 mg of naphthyl isocyanate was added. The mixture was stirred at room temperature overnight, then added directly to a silica gel column and purified by flash chromatography, eluting with a gradient system of 2:1 $CH_2Cl_2$-acetone to 1:1 $CH_2Cl_2$-acetone. Further purification by preparative thin-layer chromatography, eluting with 1:1 $CH_2Cl_2$-acetone, provided 15.4 mg of the title compound as a white solid. Mass spectrum (ESI) 494.2 (M+1). $^1$H NMR (500 MHz, $CDCl_3$): δ8.61 (s, 1H), 8.37 (d, J=5.3 Hz, 1H), 8.16 (d, J=8.0 Hz, 1H), 7.78–7.88 (m, 3H), 7.65 (d, J=8.0 Hz, 1H), 7.59 (d, J=7.6 Hz, 1H), 7.34–7.50 (m, 5H), 6.79 (d, J=5.3 Hz, 1H), 6.67 (s, 1H), 4.33 (br s, 1H), 4.03 (br t, J=13.5 Hz, 2H), 3.88 (br d, J=12.6 Hz, 1H), 3.62–3.72 (m, 2H) 3.05–3.18 (m, 2H), 1.39 (d, J=6.6 Hz, 3H).

EXAMPLE 13

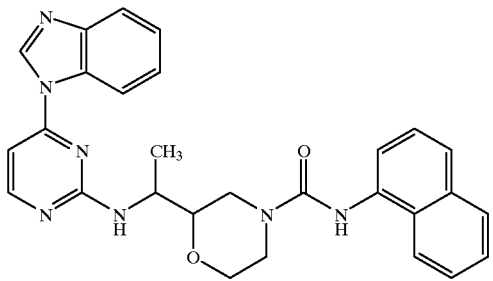

2-[1-(4-(N-Naphth-1-yl-carbamoyl)morpholine-2-yl)ethylamino]-4-[benzimidazol-1-yl]pyrimidine, diastereomer 2

Step A: 2-(1-Aminoethyl)-4-benzyloxycarbonyl-morpholine, diastereomer 2

The title compound (141 mg) was prepared from 200 mg of 2-(1-hydroxyethyl)-4-benzyloxycarbonyl-morpholine, diastereomer 2, 146 mg of diisopropylethylamine, 104 mg of methanesulfonyl chloride, 244 mg of sodium azide, and 590 mg of triphenylphosphine, by a procedure analogous to that described in EXAMPLE 12, Step E. $^1$H NMR (500 MHz, $CDCl_3$): δ7.28–7.40 (m, 4H), 5.14 (br s, 2H), 3.78–4.16 (m, 3H), 3.48–3.59 (m, 1H), 3.33 (br s, 1H), 2.62–3.17 (m, 5H), 1.16 (br d, J=5.0 Hz, 3H).

Step B: 2-[1-(4-(Benzyloxycarbonyl)morpholine-2-yl)ethylamino]4-[benzimidazol-1-yl]pyrimidine, diastereomer 2

To a 0° C. solution of 250 mg of 2-hexanethio-4-[benzimidazol-1-yl]pyrimidine (EXAMPLE 2) in 4.5 mL of MeOH and 0.5 mL of $CH_2Cl_2$ was added a suspension of 1.48 g of Oxone® in 4 mL of water. The mixture was stirred 5 min at 0° C.; then the cooling bath was removed and the mixture was stirred for an additional 2 h. The mixture was then diluted with 25 mL of water and extracted with 3×15 mL of $CH_2Cl_2$. The combined organic extracts were washed with 10 mL of brine, dried over $Na_2SO_4$, and concentrated to a red-brown foam. This foam was dissolved in 3 mL of toluene and a solution of 140 mg of 2-(1-aminoethyl)-4-benzyloxycarbonyl-morpholine, diastereomer 2, in 2 mL of toluene was added. The mixture was stirred at 100° C. overnight, then cooled, diluted with 20 mL of EtOAc, and washed with 2×10 mL of water and 10 ml of brine. The organic phase was dried over $Na_2SO_4$ and concentrated. The residue was purified by flash chromatography, eluting with 4:1 $CH_2Cl_2$-acetone to yield 74 mg of the title compound. $^1$H NMR (500 MHz, $CDCl_3$): δ8.60 (s, 1H), 8.39 (br s, 1H), 8.15 (d, 1H), 7.86 (d,1H), 7.28–7.43 (m, 5H), 6.82 (d, 1H), 5.03–5.10 (m, 2H), 4.30 (br s, 1H), 3.85–4.20 (m, 3H), 3.45–3.65 (m, 2H) 2.80–3.10 (m, 2H), 1.30 (br s, 3H). Mass spectrum (ESI) 459.2 (M+1).

Step C: 2-[1-(4-(N-Naphth-1-yl-carbamoyl)morpholine-2-yl)ethylamino]-4-[benzimidazol-1-yl]pyrimidine, diastereomer 2

The title compound was prepared from 70 mg of 2-[1-(4-(benzyloxycarbonyl)morpholine-2-yl)ethylamino]-4-[benzimidazol-1-yl]pyrimidine, diastereomer 2, and 34 mg of naphthyl isocyanate, by a procedure analogous to that described in EXAMPLE 12, Step G. Mass spectrum (ESI) 494.2 (M+1). $^1$H NMR (500 MHz, $CDCl_3$): δ8.57 (s, 1H), 8.32 (d, J=5.3 Hz, 1H), 8.13 (d, J=8.0 Hz, 1H), 7.7–7.86 (m, 3H), 7.62 (d, J=8.0 Hz, 1H), 7.55 (br d, J=6.0 Hz, 1H), 7.31–7.47 (m, 5H), 6.83 (br s, 1H), 6.74 (d, J=5.5 Hz, 1H), 4.29 (br s, 1H), 3.98 (br d, J=1 1.2 Hz, 1H), 3.84 (br d, J=12.8 Hz, 1H), 3.52–3.66 (m, 2H) 3.13 (br t, J=l 1.5 Hz, 1H), 2.97 (br t, J=11.7 Hz, 1H), 1.32 (d, J=6.6 Hz, 3H).

EXAMPLE 14

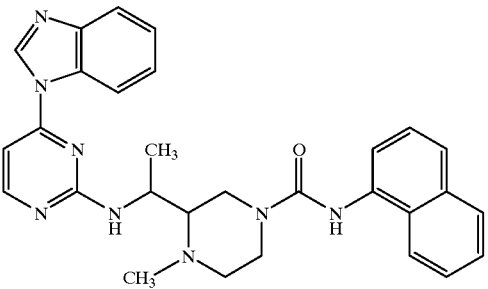

2-[1-(1-Methyl-4-(N-naphth-1-yl-carbamoyl)piperazine-2-yl)-ethylamino]-4-[benzimidazol-1-yl]pyrimidine, diastereomer 1

Step A: 1-Benzyloxycarbonyl-4-tert-butyloxycarbonylpiperazine-2-(N-methyl-N-methoxy)carboxamide To a solution of 10.00 g of piperazine-2-carboxylic acid in 250 mL of 1:1 dioxane-water at pH 11 was added dropwise a solution of 13.3 g of 2-(tert-butoxycarbonyloxyimino)-2-phenylacetonitrile in 75 mL of dioxane, maintaining the pH of the solution at 11 during the addition with the use of 5N NaOH. The mixture was stirred for 6 h at room temperature, then cooled to 0° C. The pH was adjusted to 9.5 with the use of 1N HCl. Benzyl chloroformate (9.2 g) was added dropwise, maintaining the pH of the solution at 9.5 during the addition with the use of 5N NaOH. The mixture was allowed to warm to room temperature and stirred for 20 h, then extracted with 2×200 mnL of $Et_2O$, acidified to pH<2 with 1N HCl, and extracted with 4×100 mL of EtOAc. The combined EtOAc extracts were washed with 100 mL of brine, dried over $MgSO_4$, and concentrated to a pale yellow oil. This oil was dissolved in 200 mL of $CH_2Cl_2$, and 5.3 g N,O-dimethylhydroxylamine, 10.3 g of 1-(3-dimethylaminopropyl)-3-ethylcarbodiimide hydrochloride, 14.9 g of triethylamine, and 1.2 g of dimethylaminopyridine were added sequentially. The mixture stirred overnight at room temperature, then poured into 400 mL of water. The phases were separated and the aqueous phase was extracted with 200 mL of $CH_2Cl_2$. The combined organics were washed with 100 mL each of 1N HCl, water, and brine, dried over $Na_2SO_4$, and concentrated. The residue was purified by flash chromatography, eluting with a gradient system of 2:1 hexanes-EtOAc to 1:1 hexanes-EtOAc to yield 13.5 g of the title compound as a colorless oil. $^1$H NMR (500 MHz, DMSO-d6, 80° C.): δ7.24–7.40 (m, 5H), 5.00–5.18 (m, 2H), 4.80 (br s, 1H), 4.18 (br d, J=10.0 Hz, 1H), 3.85 (br d, J=12.8 Hz, 1H), 3.40–3.80 (m, 5H), 3.30 (dd, J=5.0, 14.2 Hz, 1H),1.37 (s, 9H).

Step B: 1-Benzyloxycarbonyl-2-acetyl-4-tert-butyloxycarbonylpiperazine

To a solution of 13.5 g of 1-benzyloxycarbonyl-4-tert-butyloxy-carbonylpiperazine-2-(N-methyl-N-methoxy)carboxamide in 300 mL of THF at 0° C. was added 71 mL of a 1.4M solution of methylmagnesium bromide in toluene. The cooling bath was removed after 15 min and the mixture was stirred at room temperature for 1 h. The reaction was quenched by addition of ca. 200 mL of saturated $NH_4Cl$ and the mixture was stirred vigorously for 15 min at room temperature, then diluted with 100 mL of water. The phases were separated and the aqueous phase was extracted with 2×100 mL of $Et_2O$. The combined organics were washed with 100 mL of brine, dried over $Na_2SO_4$, and concentrated to yield 11.6 g of a yellow oil that was used without further purification. $^1H$ NMR (500 MHz, $CDCl_3$): δ7.20–7.35 (m, 5H), 5.00–5.16 (m, 2H), 4.42–4.70 (m, 2H), 3.70–4.18 (m, 2H), 3.00–3.32 (m, 2H), 2.68–2.96 (m, 1H), 2.20–2.36 (m, 3H),1.40 (s, 9H).

Step C: 1-Benzyloxycarbonyl-2-(1-hydroxyethyl)-4-tert-butyloxycarbonyl-piperazine To a solution of 6.50 g of 1-benzyloxycarbonyl-2-acetyl-4-tert-butyloxycarbonyl-piperazine in 150 mL of 1:1 THF-EtOH was added 1.35 g of sodium borohydride, in several portions. The mixture was stirred at room temperature for 30 min, then quenched by slow addition of 100 mL of saturated $NaHCO_3$. The mixture was diluted with 150 mL of water and the phases were separated. The aqueous phase was extracted with 2×100 mL of EtOAc. The combined organics were washed with 100 mL of brine, dried over $MgSO_4$, and concentrated. The residue was purified by flash chromatography, eluting with 2:1 hexanes-EtOAc, to yield 3.05 g of diastereomer 1 and 272 g of diastereomer 2. Data for diastereomer 1. $R_f$ 0.63 (1:1 hexanes-EtOAc). $^1H$ NMR (500 MHz, DMSO-d6, 75° C.): δ7.24–7.40 (m, 5H), 5.10 (s, 2H), 4.52 (d, J=5.0 Hz, 1H), 4.20 (d, J=13.1 Hz, 1H), 3.71–3.92 (m, 4H), 2.76–2.96 (m, 3H),1.40 (s, 9H), 1.00 (d, J=5.5 Hz, 3H). Mass spectrum (ESI) 309.1 (M-BOC). Data for diastereomer 2. $R_f$ 0.53 (1:1 hexanes-EtOAc). $^1H$ NMR (500 MHz, DMSO-d6, 75° C.): δ7.23–7.40 (m, 5H), 5.08 (s, 2H), 4.41 (br s, 1H), 3.74–3.92 (m, 5H), 3.02–3.11 (m, 1H),2.98 (dd, J=3.4, 13.5 Hz, 1H), 2.28 (br t, J=11.7 Hz, 1H), 1.40 (s, 9H), 1.16 (d, J=6.0 Hz, 3H).

Step D: 1-Benzyloxycarbonyl-2-(1-aminoethyl)-4-tert-butyloxycarbonyl-piperazine, diastereomer 1

To a solution of 1.84 g of 1-benzyloxycarbonyl-2-(1-hydroxyethyl)-4-tert-butyloxycarbonylpiperazine, diastereomer 1, in 100 mL of toluene was added 860 mg of imidazole, 3.71 g of triphenylphosphine, and 3.42 g of $Zn(N_3)_2 \cdot pyr_2$, successively. Diisopropylazodicarboxylate (2.86 g) was then added dropwise. A thick orange sludge formed, which was stirred at room temperature for 2 h. The solvent was decanted into a separatory funnel and the sludge was rinsed with 2×100 mL of EtOAc, and the rinses were added to the funnel. The sludge was then dissolved in 200 mL of 1N HCl, and this solution was added to the funnel. The phases were separated and the organic phase was washed with 100 mL of 1N HCl, saturated $NaHCO_3$, and brine, dried over $Na_2SO_4$ and concentrated. The residue was dissolved in minimal $CH_2Cl_2$ and preadsorbed onto 20 g of silica gel. Flash chromatography, eluting with 4:1 hexanes-EtOAc provided 1.70 g of the desired product, contaminated with minor amounts of reaction by-products. This mixture was dissolved in 50 mL of 9:1 THF-water and 1.62 g of triphenylphosphine was added. The mixture was heated to 50° C. and stirred at this temperature for 5 h; then another 540 mg of triphenylphosphine was added and the mixture was heated to 75° C. for 3 h. The mixture was then cooled, poured into 25 mL of 1N HCl, and extracted with 2×10 mL of EtOAc. The aqueous phase was made very basic (pH>12) by addition of 5N NaOH, then extracted with 5×10 mL of EtOAc. The combined organic extracts were washed with 10 mL of brine, dried over $Na_2SO_4$, and concentrated to yield 268 mg of the title compound, which was used without further purification. Concentration of the organic washes of the acidic aqueous solution provided a white oily solid; flash chromatography of this solid, eluting with 95:5 $CH_2Cl_2$—MeOH provided an additional 658 mg of amine. $^1H$ NMR (500 MHz, $CDCl_3$): δ7.27–7.40 (m, 5H), 5.16 (ABq, J=12.4 Hz, 2H), 3.64–4.22 (m, 4H), 2.68–3.15 (m, 4H), 1.40–1.60 (m, 11H), 1.18–1.28 (m, 3H).

Step E: 2-[1-(1-(Benzyloxycarbonyl)-4-(tert-butyloxycarbonyl)-piperazin-2-yl)-ethylamino]-4-[benzimidazol-1-yl]pyrimidine, diastereomer 1

To a solution of 82 mg of 2-methanesulfonyl-4-[benzimidazol-1-yl]pyrimidine (EXAMPLE 1 Step B) in 0.5 mL of DMF was added a solution of 125 mg of 1-benzyloxycarbonyl-2-(1-aminoethyl)-4-tert-butylcarbonylpiperazine, diastereomer 1, in 1 mL of toluene. The mixture was heated to 100° C. and stirred at this temperature for 16 h, then cooled, diluted with 20 mL of EtOAc, and washed with 2×10 mL of water and 10 ml of brine. The organic phase was dried over $Na_2SO_4$ and concentrated. The residue was purified by flash chromatography, eluting with 4:1 $CH_2Cl_2$-acetone. Further purification by preparative thin layer chromatography, eluting with 4:1 $CH_2C_2$-acetone, provided 39 mg of the title compound. $^1H$ NMR (500 MHz, $CDCl_3$): δ8.57 (br s, 1H), 8.34 (br s, 1H), 8.04–8.26 (m, 1H), 7.85 (d, J=10 Hz, 1H), 7.26–7.50 (m,4H), 7.08 (br s, 1H), 6.68–6.84 (m, 1H), 5.45–5.80 (m, 1H), 4.82–5.60 (m, 2H), 4.62 (br s, 1H), 3.75–4.40 (m, 4H), 2.95–3.30 (m, 2H), 2.82 (br s, 1H), 1.35–1.60 (m, 12H). Mass spectrum (ESI) 558.3 (M−1).

Step F: 2-[1-(1-(Benzyloxycarbonyl)-4-(N-naphth-1-yl-carbamoyl)-piperazin-2-yl)-ethylamino]-4-[benzimidazol-1-yl]pyrimidine, diastereomer 1

To a 0° C. solution of 35 mg of 2-[1-(1-(benzyloxycarbonyl)-4-(tert-butyloxycarbonyl)-piperazin-2-yl)-ethylamino]-4-[benzimidazol-1-yl]pyrimidine, diastereomer 1, in 1 mL of $CH_2Cl_2$ was added 1 mL of trifluoroacetic acid. The mixture was stirred at room temperature for 30 min, then concentrated. The residue was dissolved in 0.5 mL of pyridine and 13 mg of naphthyl isocyanate was added. The mixture was stirred at room temperature for 4 h, then diluted with 15 mL of $CH_2Cl_2$ and washed with 2×5 mL of 1M $NaHSO_4$ and 5 mL of brine, dried over $Na_2SO_4$, and concentrated. Purification by preparative thin-layer chromatography, eluting with 2:1 $CH_2Cl_2$-acetone, provided 29 mg of the title compound as a white solid. $^1H$ NMR (500 MHz, $CD_3OD$, 50° C.): δ8.86 (s, 1H), 8.47 (d, J=5.5 Hz, 1H), 8.23 (d J=8.0 Hz, 1H), 8.00 (br d, J=6.9 Hz, 1H), 7.87 (d, J=9.4 Hz, 1H), 7.79 (d, J=7.6 Hz, 1H), 7.75 (d, J=8.2 Hz, 1H), 7.38–7.53 (m, 7H), 6.90–7.08 (m, 5H), 4.88–5.00 (m, 2H), 4.72–4.81 (m, 1H), 4.67 (br d, J=13.7 Hz, 1H), 4.21–4.47 (m, 3H), 3.70–3.82 (m, 1H), 3.34–3.44 (m, 2H), 1.41 (d, J=6.5 Hz, 3H). Mass spectrum (ESI) 627.3 (M+1).

Step G: 2-[1-(1-Methyl-4-(N-naphth-1-yl-carbamoyl)piperazine-2-yl)-ethylamino]-4-[benzimidazol-1-yl] pyrimidine, diastereomer 1

To a 0° C. solution of 35 mg of 2-[1-(1-(benzyloxycarbonyl)-4-(N-naphth-1-yl-carbamoyl)- piperazin-2-yl)-ethylamino]-4-[benzimidazol-1-yl]-pyrimidine, diastereomer 1, in 1 mL of CH₂Cl₂ was added 0.3 mL of 30% HBr in acetic acid. The cooling bath was removed after 10 min and the mixture was stirred at room temperature for 1 h, then diluted with 15 mL of water and extracted with 10 mL of EtOAc. The phases were separated and the aqueous phase was extracted with 5 mL of EtOAc. The pH of the aqueous phase was adjusted to >11 with 5 N NaOH, and the aqueous phase was extracted with 5×5 mL of EtOAc, with continuous monitoring of the pH. The combined EtOAc extracts were dried over Na₂SO₄ and concentrated. The residue was dissolved in 1 mL of 1:1 CH₃CN—MeOH and 23 μL of a 37% aqueous solution of formaldehyde was added. After stirring 15 min at room temperature, 4.3 mg of sodium cyanoborohydride was added and the mixture was stirred for overnight at room temperature, then diluted with 5 mL of EtOAc and poured into 15 mL of 1N HCl. The phases were separated and the aqueous phase was extracted 5 mL of EtOAc. The aqueous phase was made very basic (pH>10) by addition of 5N NaOH, then extracted with 5×5 mL of EtOAc. The combined organic extracts were washed with 10 mL of brine, dried over Na₂SO₄, and concentrated. The residue was purified by preparative thin layer chromatography, eluting with 19:1 CH₂Cl₂—MeOH, to yield 8.3 mg of the title compound as an off-white solid. ¹H NMR (500 MHz, CDCl₃): δ8.57 (s, 1H), 8.29 (br s, 1H), 8.06–8.13 (m, 1H), 7.82–7.88 (m, 1H), 7.72–7.81 (m, 2H), 7.57 (d, J=8.0 Hz, 1H), 7.51 (d, J=7.3 Hz, 1H), 7.30–7.44 (m, 4H),7.00 (br s, 1H), 6.71 (d, J=5.5 Hz, 1H), 5.90 (br s, 1H), 4.48–4.59 (m, 1H), 4.05 (br d, J=13.1 Hz, 1H), 3.84 (br d, J=12.6 Hz, 1H), 3.08 (br t, J=9.6 Hz, 1H), 2.90–2.96 (m, 1H), 2.78–2.83 (m, 1H),2.40–2.48 (m, 4H), 2.30–2.39 (m, 1H), 1.27 (d, J=6.9 Hz, 3H). Mass spectrum (ESI) 507.3 (M+).

EXAMPLE 15

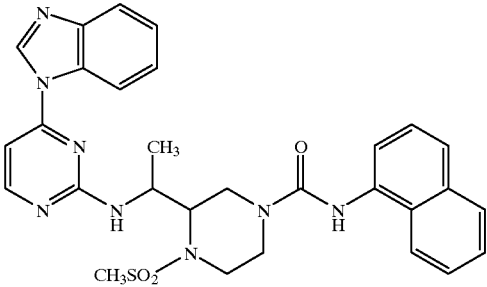

2-[1-(1-Methanesulfonyl-4-(N-naphth-1-yl-carbamoyl)-piperazin-2-yl)ethylamino]-4-[benzimidazol-1-yl]pyrimidine, diastereomer 1

To a 0° C. solution of 35 mg of 2-[1-(1-(benzyloxycarbonyl)-4-(N-naphth-1-yl-carbamoyl)-piperazin-2-yl)-ethylamino]-4-[benzimidazol-1-yl]-pyrimidine, diastereomer 1, (from EXAMPLE 14, step F) in 1 mL of CH₂Cl₂ was added 0.3 mL of 30% HBr in acetic acid. The cooling bath was removed after 15 min and the mixture was stirred at room temperature for 45 min, then diluted with 15 mL of water and extracted with 10 mL of EtOAc. The phases were separated and the aqueous phase was extracted with 5 mL of EtOAc. The pH of the aqueous phase was adjusted to >11 with 5N NaOH, and the aqueous phase were extracted with 5×5 mL of EtOAc, with continuous monitoring of the pH. The combined EtOAc extracts were dried over Na₂SO₄ and concentrated. The residue was dissolved in 0.5 mL of CH₂Cl₂ and 6.2 mg of diisopropylethylamine, then 4.4 mg of methanesulfonyl chloride were added. The mixture was stirred 1 h at room temperature, then diluted with 10 mL of EtOAc and extracted with 2×5 mL of 1M NaHSO₄ and 2×5 mL of saturated NaHCO₃. The organic phase was dried over Na₂SO₄ and concentrated, then purified by preparative thin layer chromatography, eluting with 95:5 CH₂Cl₂—MeOH to yield the title compound as a white solid. ¹H NMR (500 MHz, CDCl₃): δ 8.61 (br s, 1H), 8.39 (br s, 1H), 8.18 (d, J=8.2 Hz, 1H), 7.80–7.90 (m, 2H), 7.70 (t, J=8.2 Hz, 2H), 7.63 (d, J=7.6 Hz, 1H), 7.30–7.55 (m, 4H), 6.80 (d, J=5.3 Hz, 1H), 6.69 (s, 1H), 4.76 (br s, 1H), 4.38 (d, J=14.2 Hz, 1H), 3.76–4.04 (m, 2H), 3.40–3.68 (m, 2H), 3.15–3.31 (m, 2H), 2.87 (s, 3H), 1.46 (d, J=5.0 Hz, 3H). Mass spectrum (ESI) 571.2 (M+1).

EXAMPLE 16

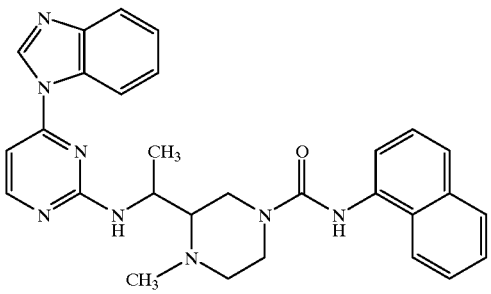

2-[1-(1-Methyl-4-(N-naphth-1-yl-carbamoyl)-piperazin-2-yl)-ethylamino]-4-[benzimidazol-1-yl]pyrimidine, diastereomer 2

Step A: 1-Benzyloxycarbonyl-2-(1-aminoethyl)-4-tert-butyloxycarbonylpiperazine, diastereomer 2

The title compound (608 mg) was prepared from 1.66 g of 1-benzyloxycarbonyl-2-(1-hydroxyethyl)-4-tert-butyloxycarbonylpiperazine, diastereomer 2, 780 mg of imidazole, 3.35 g of triphenylphosphine, 3.08 g of Zn(N₃)₂·pyr₂, 2.58 g of diisopropylazodicarboxylate, and then 1.51 g of triphenylphosphine, by a procedure analogous to that described in EXAMPLE 14, step D. ¹H NMR (500 MHz, CDCl₃): δ7.27–7.40 (m, 5H), 5.15 (br s, 2H), 4.20–4.45 (m, 1H), 3.50–4.20 (m, 5H), 2.70–3.20 (m, 4H), 1.47 (br s, 9H), 1.04 (br s, 3H).

Step B: 2-[1-(1-(Benzyloxycarbonyl)-4-(tert-butyloxycarbonyl)-piperazin-2-yl)-ethylamino]-4-[benzimidazol-1-yl]pyrimidine, diastereomer 2

The title compound (15 mg) was prepared from 82 mg of 2-methanesulfonyl-4-[benzimidazol-1-yl]pyrimidine (EXAMPLE 1 Step B) and 125 mg of 1-benzyloxycarbonyl-2-(1-aminoethyl)-4-tert-butyloxycarbonylpiperazine, diastereomer 2, by a procedure analogous to that described in EXAMPLE 14, step E. ¹H NMR (500 MHz, CDCl₃): δ8.56–8.66 (m, 1H), 8.32–8.42 (m, 1H), 8.06–8.16 (m, 1H), 7.82–7.88 (m, 1H), 7.29–7.44 (m, 4H), 6.76–6.86 (m, 11H), 5.18 (br s, 2H), 4.64 (br s, 1H), 3.70–4.34 (m, 4H), 2.72–3.20 (m, 3H), 1.00–1.38 (m, 12H). Mass spectrum (ESI) 558.3 (M−1).

Step C: 2-[1-(1-(Benzyloxycarbonyl)-4-(N-naphth-1-yl-carbamoyl)-piperazin-2-yl)-ethylaminol-4-lbenzimidazol-1-yl]pyrimidine, diastereomer 2

The title compound (7 mg) was prepared from 15 mg of 2-[1-(1-(benzyloxycarbonyl)-4-(tert-butyloxycarbonyl)-piperazin-2-yl)-ethylamino]-4-[benzimidazol-1-yl]pyrimidine, diastereomer 2 and 5.5 mg of naphthyl isocyanate by a procedure analogous to that described in EXAMPLE 14, step F. $^1$H NMR (500 MHz, CDCl$_3$): δ8.32–8.42 (m, 1H), 7.16–8.05 (m, 13H), 6.39 (d, J=5.0 Hz, 1H), 5.14–5.30 (m, 2H), 4.78–4.90 (m, 1H), 4.08–4.40 (m, 4H), 3.23–3.38 (m, 1H), 3.11 (br s, 1H), 2.83–3.00 (m, 1H), 1.24–1.32 (m, 3H).

Step D: 2-[1-(1-Methyl-4-(N-naphth-1-yl-carbamoyl)-piperazin-2-yl)-ethylamino]-4-[benzimidazol-1-yl] pyrimidine, diastereomer 2

The title compound (3.8 mg) was prepared from 7 mg of 2-[1-(1-(benzyloxycarbonyl)-4-(N-naphth-1-yl-carbamoyl)-piperazin-2-yl)-ethylamino]-4-[benzimidazol-1-yl] pyrimidine, diastereomer 2, 5.5 µL of 37% aqueous formaldehyde, and 1 mg NaBH$_3$CN of by a procedure analogous to that described in EXAMPLE 14, step G. $^1$H NMR (500 MHz, CDCl$_3$): δ8.61 (br s, 1H), 8.37 (d, J=4.8 Hz, 1H), 8.12 (d, J=7.1 Hz, 1H), 7.80–7.89 (m, 3H), 7.66 (t, J=8.2 Hz, 2H), 7.72–7.81 (m, 2H), 7.34–7.50 (m, 4H), 6.78 (d, J=5.3 Hz, 1H), 6.68 (br s, 1H), 5.70 (br s, 1H), 4.50 (br s, 1H), 4.18 (br d, J=11.2 Hz, 1H), 3.85 (br d, J=12.6 Hz, 1H), 3.29–3.39 (m, 1H), 3.05–3.18 (m, 1H), 2.93 (br d, J=11.9 Hz, 1H), 2.45–2.55 (m, 1H), 2.39 (s, 3H), 2.25–2.37 (m, 1H), 1.35 (d, J=6.9 Hz, 3H).

EXAMPLE 17

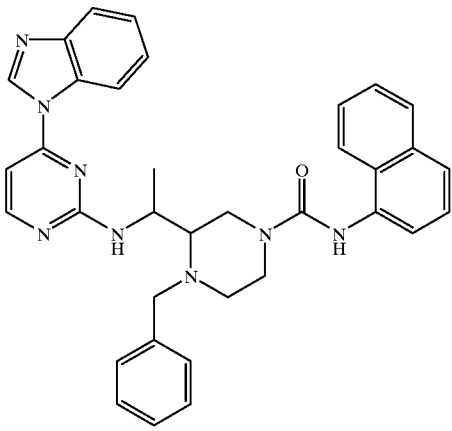

2-[1-(1-Benzyl-4-(N-naphth-1-yl-carbamoyl)piperazin-2-yl)-ethylamino]-4-[benzimidazol-1-yl]-pyrimidine Step A: 2-Chloro-4-(benzimidazol-1-yl)-5-bromopyrimidine To a suspension of NaH (23 mg) in 1.5 mL of DMF was added benzimidazole (111 mg). After gas evolution ceased, the mixture was stirred at room temperature for 10 min, then added to a solution of 2,4-dichloro-5-bromopyrimidine (178 mg) in 1 mL of DMF. The mixture was stirred for 3 h at room temperature, then diluted with 10 mL of EtOAc and quenched with 5 mL of water. The phases were separated and the organic phase was washed with 5 mL of water and 5 mL of brine, then dried over Na$_2$SO$_4$ and concentrated. The residue was purified by flash chromatography, eluting with 4:1 hexanes-acetone to provide 151 mg of the title compound (polar isomer) and 15 mg of the regioisomer 2-(benzimidazol-1-yl)-4-chloro-5-bromopyrimidine (nonpolar isomer). Mass spectrum (ESI) 310.9 (M+1).

Step B: 2-[1-(1-(Benzyloxycarbonyl)-4-(tert-butyloxycarbonyl)-piperazin-2-yl)ethylamino]-4-(benzimidazol-1-yl)-5-bromopyrimidine A solution of 2-chloro-4-(benzimidazol-1-yl)-5-bromopyrimidine (100 mg) and 1-benzyloxycarbonyl-2-(1-aminoethyl)-4-tert-butyloxycarbonylpiperazine, diastereomer 1 (EXAMPLE 14 Step D; 115 mg), in 10 mL of toluene was heated to 100° C. and stirred overnight (14 h) at this temperature. The mixture was then cooled and diluted with 20 mL of EtOAc and 30 mL of water. The phases were separated and the aqueous phase was extracted with 2×20 mL of EtOAc. The combined organics were dried over MgSO$_4$ and concentrated. The residue was purified by flash chromatography, eluting with 20:1 hexanes-acetone to provide 133 mg of the title compound. Mass spectrum (ESI) 638.4 (M+1).

Step C: 2-[1-(4-(Tert-butyloxycarbonyl)-piperazin-2-yl)-ethylamino]-4-(benzimidazol-1-yl)-pyrimidine A solution of 2-[1-(1-(benzyloxycarbonyl)-4-(tert-butyloxycarbonyl)-piperazin-2-yl)-ethylamino]-4-(benzimidazol-1-yl)-5-bromopyrimidine (83 mg) in 1 mL of iPrOH was stirred over Pd(OH)$_2$/C (75 mg) under an H$_2$ atmosphere (balloon) for 2 days, then filtered through Celite®, washing liberally with MeOH, and concentrated. The residue was dissolved in 10 mL of 0.2 N HCl and washed with 2×5 mL of CH$_2$Cl$_2$. The aqueous phase was basified (pH>11) with 1N NaOH and extracted with 4×10 mL of EtOAc. The combined organics were dried over Na2SO$_4$ and concentrated, and the residue was purified by preparative thin-layer chromatography, eluting with 9:1 CH$_2$Cl$_2$—MeOH to provide 17 mg of the title compound. Mass spectrum (ESI) 368.3 (M–tBu).

Step D: 2-[1-(1-Benzyl-4-(N-naphth-1-yl-carbamoyl) piperazine-2-yl)-ethylamino]-4-[benzimidazol-1-yl]-pyrimidine To a solution of 2-[1-(4-(tert-butyloxycarbonyl)-piperazine-2-yl)-ethylamino]-4-(benzimidazol-1-yl)-pyrimidine (2 mg) in 0.5 mL of DMF was added benzyl bromide (1.1 µL) and K$_2$CO$_3$ (1.3 mg). The mixture was stirred overnight at room temperature, then diluted with 5 mL of EtOAc and poured into 10 mL of 1N HCl. The phases were separated and the aqueous phase was basified (pH>11) with 5N NaOH and extracted with 4×5 mL of EtOAc. The combined organics were dried over Na2SO$_4$ and concentrated. The residue was dissolved in 0.5 mL of CH$_2$Cl$_2$ and 0.25 mL of trifluoroacetic acid was added. The mixture was stirred for 2 h at room temperature, then concentrated. The residue was dissolved in 0.5 mL of pyridine and naphthyl isocyanate (1 µL) was added. The mixture was stirred overnight at room temperature, then co-concentrated with heptane. The residue was purified by preparative thin-layer chromatography, eluting with 95:5 CH$_2$Cl$_2$—MeOH to provide 0.9 mg of the title compound. Mass spectrum (ESI) 583.5 (M+1).

EXAMPLE 18

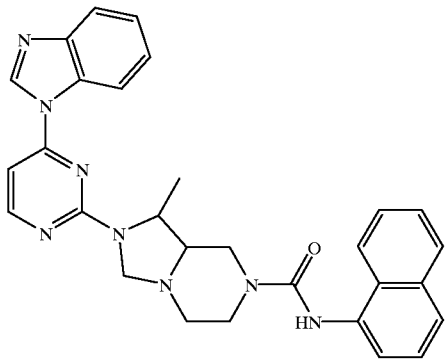

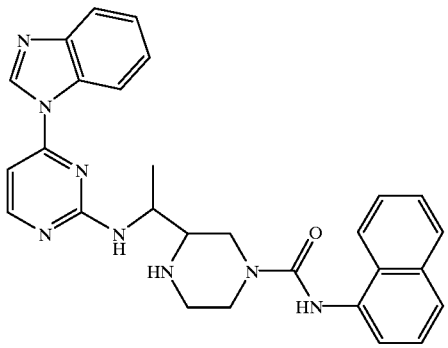

2-[1-(4-(N-naphth-1-yl-carbamoyl)-piperazine-2-yl)-ethylamino]-4-(benzimidazol-1-yl)pyrimidine and 2-[7-methyl-4-(N-naphth-1-y-carbamoyl)-1,4,8-triazabicyclo-[4,3,0]nonan-8-yl]-4-[benzimidazol-1-yl]-pyrimidine Step A: 2-[1-(1-(Benzyloxycarbonyl)-4-(N-naphth-1-yl-carbamoyl)-piperazin-2-yl)-ethylamino]-4-(benzimidazol-1-yl)-5-bromopyrimidine To a solution of 2-[1-(1-(benzyloxycarbonyl)-4-(tert-butyloxycarbonyl)piperazin-2-yl)ethylamino]-4-(benzimidazol-1-yl)-5-bromopyrimidine (EXAMPLE 17, Step B; 135 mg) in 1 mL of CH$_2$Cl$_2$ was added 0.5 mL of trifluoroacetic acid. The mixture was stirred for 2 h at room temperature, then concentrated. The residue was dissolved in 1 mL of pyridine and 1 mL of CH$_2$Cl$_2$ and naphthyl isocyanate (37 μL) was added. The mixture was stirred overnight at room temperature, then concentrated, redissolved in CH$_2$C$_2$—MeOH and preadsorbed onto 500 mg of silica gel. The compound was purified by flash chromatography, eluting with 4:1 CH$_2$Cl$_2$-acetone to provide 142 mg of the title compound. Mass spectrum (ESI) 707.1 (M+1).

Step B: 2-[1-(4-(N-naphth-1-yl-carbamoyl)-piperazine-2-yl)-ethylamino]-4-(benzimidazol-1-yl)pyrimidine and 2-[7-methyl-4-(N-naphth-1-yl-carbamoyl)-1,4,8-triazabicyclo[4,3,0]nonan-8-yl]-4-[benzimidazol-1-yl]pyrimidine A solution of 2-[1-(1-(benzyloxycarbonyl)-4-(N-naphth-1-yl-carbamoyl)-piperazin-2-yl)-ethylamino]-4-(benzimidazol -1-yl)-5-bromopyrimidine 140 mg) in 2 mL of MeOH was stirred over Pd(OH)$_2$/C (140 mg) under an H$_2$ atmosphere (balloon) overnight, then filtered through Celite®, washing liberally with MeOH, and concentrated. The residue was purified by preparative thin-layer chromatography, eluting with 9:1 CH$_2$Cl$_2$—2M NH$_3$ in MeOH to provide 5 mg of the title compound. Mass spectrum (ESI) 505.2 (M+1). The major product (17 mg) of this reaction was 2-[1-(4-(N-naphth-1-yl-carbamoyl)-piperazine-2-yl)-ethylamino]-4-(benzimidazol-1-yl)pyrimidine. Mass spectrum (ESI) 493.2 (M+1).

EXAMPLE 19

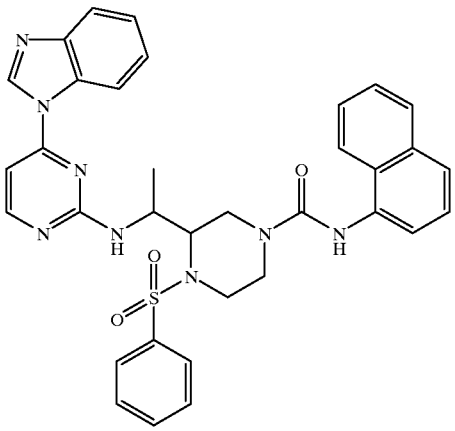

2-[1-(1-Benzenesulfonyl-4-(N-naphth-1-yl-carbamoyl)piperazin-2-yl)ethylamino]-4-[benzimidazol-1-yl]-pyrimidine To a solution of 2-[1-(4-(N-naphth-1-yl-carbamoyl)-piperazin-2-yl)-ethylamino]-4-(benzimidazol-1-yl) (EXAMPLE 18, Step B; 8.5 mg) in 0.5 mL of CH$_2$Cl$_2$ was added diisopropylethylamine (5 μL) and benzenesulfonyl chloride (3 μL). The mixture was stirred overnight at room temperature, then concentrated. The residue was purified by flash chromatography, eluting with 9:1 CH$_2$Cl$_2$—MeOH to provide 3.5 mg of the title compound. Mass spectrum (ESI) 633.2 (M+1).

EXAMPLE 20

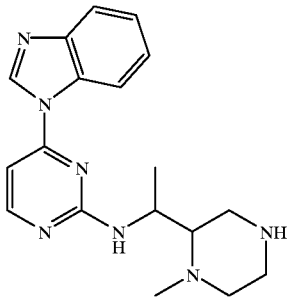

2-[1-(1-Methylpiperazin-2-yl)-ethylamino]-4-[benzimidazol-1-yl]-pyrimidine

A solution of 2-[1-(1-(benzyloxycarbonyl)-4-(tert-butyloxycarbonyl)-piperazin-2-yl)-ethylamino]-4-(benzimidazol-1-yl)-pyrimidine (EXAMPLE 14, Step E; 30 mg) in 3 mL of MeOH was stirred over Pd(OH)$_2$/C (30 mg) under an H$_2$ atmosphere (balloon) for 4 h, then filtered through Celite®, washing liberally with MeOH, and concentrated. The residue was dissolved in 1 mL of MeOH and NaBH$_3$CN (6.8 mg) and 37% aqueous formaldehyde (26 μL) were added and the mixture was stirred for 5 h at room temperature, then diluted with 5 mL of EtOAc and poured into 10 mL of water. The phases were separated and the aqueous phase was extracted with 2×5 mL of EtOAc. The aqueous phase was basified (pH>10) by addition of 5N NaOH, then extracted with 5×5 mL of EtOAc. The combined organic extracts were washed with 5 mL of brine, dried over Na$_2$SO$_4$, and concentrated. The residue (16 mg) was dissolved in 1 mL of CH$_2$Cl$_2$ and 0.5 mL of trifluoroacetic acid was added. The mixture was stirred for 1 h at room temperature, then poured into 10 mL of water and extracted with 2×5 mL of CH$_2$Cl$_2$. The aqueous phase was basified (pH>10) by addition of 5N NaOH, then extracted with 4×5 mL of EtOAc. The combined organic extracts were washed with 5 mL of brine, dried over Na$_2$SO$_4$, and concentrated. The residue was purified by preparative thin-layer chromatography, eluting with 9:1 CH$_2$Cl$_2$—2M NH$_3$ in MeOH to provide 9.4 mg of the title compound. Mass spectrum (ESI) 338.3 (M+1).

EXAMPLE 21

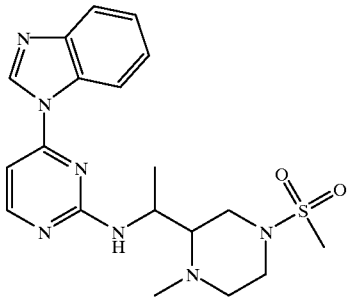

2-[1-(1-Methyl-4-(methanesulfonyl)-piperazin-2-yl)-ethylamino1-4-[benzimidazol-1-yl]pyrimidine To a 0° C. solution of 2-[1-(1-methylpiperazine-2-yl)-ethylamino]-4[-benzimidazol-1-yl]-pyrimidine (EXAMPLE 20; 6 mg) in 1 mL of CH$_2$Cl$_2$ and 0.5 mL of pyridine was added methanesulfonyl chloride (2.5 mg). The mixture was allowed to warm to room temperature and stirred overnight, then poured into 10 mL of 1M NaHSO$_4$, extracted with 2×5 mL of CH$_2$Cl$_2$, basified (pH>10) with 5N NaOH, and extracted with 5×5 mL of EtOAc. The combined EtOAc extracts were washed with 5 mL of brine, dried over Na$_2$SO$_4$ and concentrated. The residue was purified by preparative thin-layer chromatography, eluting with 9:1 CH$_2$Cl$_2$—2M NH$_3$ in MeOH to provide 1.0 mg of the title compound. Mass spectrum (ESI) 416.3 (M+1).

EXAMPLE 22

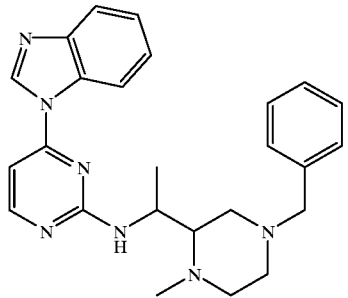

2-[1-(1-Methyl-4-benzyl-piperazine-2-yl)-ethylamino]-4-[benzimidazol-1-yl]-pyrimidine To a solution of 2-[1-(1-methylpiperazine-2-yl)-ethylamino]-4-[benzimidazol-1-yl]-pyrimidine (EXAMPLE 20; 3 mg) in 4 mL of DMSO was added benzyl bromide (2 μL) and K$_2$CO$_3$ (2.2 mg). The mixture was stirred for 2d at room temperature, then diluted with 5 mL of EtOAc and poured into 10 mL of 1N HCl. The phases were separated and the aqueous phase was basified (pH>11) with 5N NaOH and extracted with 4×5 mL of EtOAc. The combined organ-ics were dried over Na$_2$SO$_4$ and concentrated. The residue was purified by preparative thin-layer chromatography, eluting with 95:5 CH$_2$Cl$_2$—MeOH to provide 1.9 mg of the title compound. Mass spectrum (ESI) 428.4 (M+1).

EXAMPLE 23

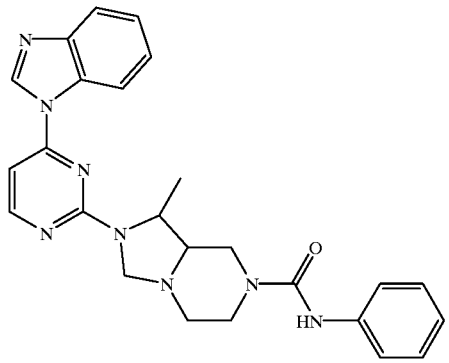

2-[7-methyl-4-(N-phenyl -carbamoyl)-1,4,8-triazabicyclo[4,3,0]nonan-8-yl]-4-[benzimidazol-1-yl]-pyrimidine Step A: 2-[7-methyl-4-(N-tert-butyloxycarbonyl)-1,4,8-triazabicyclo[4,3,0]-nonan-8-yl]-4-[benzimidazol-1-yl]-pyrimidine To a solution of 2-[1-(1-(benzyloxycarbonyl)-4-(tert-butyloxycarbonyl)-piperazine-2-yl)-ethylamino]-4-(benzimidazol-1-yl)-5-bromopyrimidine (EXAMPLE 17, Step B;) (113 mg) in 2 mL of MeOH was stirred over K2CO$_3$ (25 mg) and Pd(OH)$_2$/C under an H$_2$ atmosphere (balloon) overnight, then filtered through Celite®, washing liberally with MeOH, and concentrated. The residue was dissolved in 1 mL of MeOH and 1 mL of CH$_3$CN; NaBH$_3$CN (21 mg) and 37% aqueous formaldehyde (80 μL) were added and the mixture was stirred overnight at room temperature, then diluted with 5 mL of EtOAc and poured into 10 mL of 1N HCl. The phases were separated and the aqueous phase was extracted with 2×5 mL of EtOAc. The aqueous phase was basified (pH>10) by addition of 5N NaOH, then extracted with 4×5 mL of EtOAc. The combined organic extracts were washed with 5 mL of brine, dried over Na$_2$SO$_4$, and concentrated. The residue was purified by preparative thin-layer chromatography, eluting with 95:5 CH$_2$C$_2$—MeOH to provide 15 mg of a mixture of the title compound [mass spectrum (ESI) 436.4 (M+1)] and 2-[7-methyl-4-(N-phenyl-carbamoyl)-1,4,8-triazabicyclo[4,3,0]nonan-8-yl]-4-methoxy-pyrimidine [mass spectrum (ESI) 350.3 (M+1)].

Step B: 2-[7-methyl-4-(N-phenyl-carbamoyl)-1,4,8-triazabicyclo[4,3,0]nonan-8-yl]-4-[benzimidazol-1-yl]-pyrimidine To a solution of the product mixture from EXAMPLE 23, Step A (15 mg of the mixture) in 0.5 mL of CH$_2$Cl$_2$ was added 0.5 mL of trifluoroacetic acid, The mixture was stirred for 2 h at room temperature, then concentrated. The residue was dissolved in 0.5 mL of pyridine and phenyl isocyanate (4 μL) was added. The mixture was stirred overnight at room temperature, then diluted with 2 mL of EtOAc and 2 mL of 50% saturated NaHCO$_3$. The phases were separated and the aqueous phase was extracted with 2 mL of EtOAc. The combined organics were dried over MgSO$_4$ and concentrated. The residue was purified by preparative thin-layer chromatography, eluting with 95:5 CH$_2$Cl$_2$ MeOH to provide 5.5 mg of the title compound. Mass spectrum (ESI) 455.4 (M+1).

EXAMPLE 24

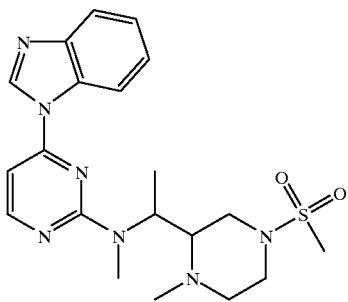

2-[1-(1-Methyl-4-(methanesulfonyl)piperazine-2-yl)-ethylaminomethyl]-4-[benzimidazol-1-yl]-pyrimidine
Step A: 2-[1-(1-Methyl-4-(tert-butyloxycarbonyl)piperazine-2-yl)-ethylamino]-4-[benzimidazol-1-yl]-pyrimidine To a solution of 2-[1-(4-(tert-butyloxycarbonyl)piperazine-2-yl)-ethylamino]-4-(benzimidazol-1-yl)-pyrimidine (EXAMPLE 17, Step C; 17 mg) in 1 mL of MeOH and 1 mL of $CH_3CN$ was added $NaBH_3CN$ (5 mg) and 37% aqueous formaldehyde (20 μL). The mixture was stirred overnight at room temperature, then diluted with 5 mL of EtOAc and poured into 10 mL of water. The phases were separated and the aqueous phase was extracted with 2×5 mL of EtOAc. The aqueous phase was basified (pH>10) by addition of 5 N NaOH, then extracted with 5×5 mL of EtOAc. The combined organic extracts were washed with 5 mL of brine, dried over $Na_2SO_4$, and concentrated to yield 15 mg of the title compound.
Step B: 2-[1-(1-Methyl-4-(methanesulfonyl)piperazine-2-yl)-ethylamino-methyl]-4-[benzimidazol-1-yl]-pyrimidine To solution of 2-[1-(1-methyl-4-(tert-butyloxycarbonyl)piperazine2-yl)ethylamino]-4-[benzimidazol-1-yl]-pyrimidine (6 mg) in 1 mL of $CH_2Cl_2$ was added 0.5 mL of trifluoroacetic acid. The mixture was stirred for 1 h at room temperature, then concentrated. The residue was dissolved in 1 mL of $CH_2Cl_2$ and diisopropylethylamine (10 μL) and methanesulfonyl chloride (2.5 mg) were added. The mixture was stirred overnight at room temperature, then concentrated. The residue was purified by preparative thin-layer chromatography, eluting with 9:1 $CH_2Cl_2$—MeOH to provide 1.7 mg of the title compound. Mass spectrum (ESI) 430.3 (M+1).

EXAMPLE 25

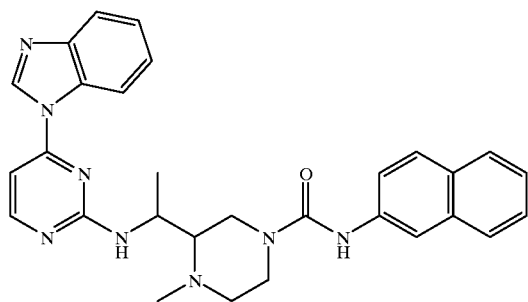

2-[1-(1-Methyl-4-(N-naphth-2-yl-carbamoyl)piperazine-2-yl)-ethylamino]-4-[benzimidazol-1-yl]-pyrimidine
To solution of 2-[1-(1-methyl-4-(tert-butyloxycarbonyl)piperazine-2-yl-4-[benzimidazol-1-yl]-pyrimidine (EXAMPLE 24, Step A; 6 mg) in 0.5 mL of $CH_2Cl_2$ was added 0.25 mL of trifluoroacetic acid. The mixture was stirred for 1 h at room temperature, then concentrated. The residue was dissolved in 0.5 mL of pyridine and 2-naphthyl isocyanate (5 mg) was added. The mixture was stirred overnight at room temperature, then co-concentrated with 2×5 mL of heptane. The residue was purified by preparative thin-layer chromatography, eluting with 9:1 $CH_2Cl_2$—MeOH to provide 1.2 mg of the title compound. Mass spectrum (ESI) 507.5 (M+1).

EXAMPLE 26

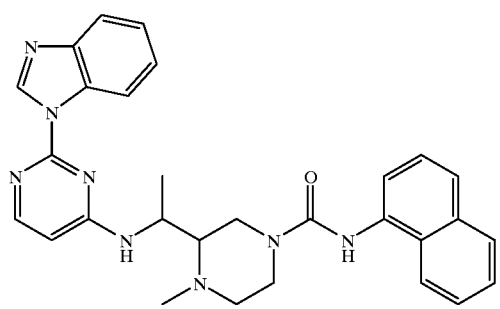

2-[Benzimidazol-1-yl]-4-[1-(1-methyl-4-(N-naphth-1-yl-carbamoyl)piperazine-2-yl)-ethylamino]pyrimidine
Step A: 2-[Benzimidazol-1-yl 1-4-methylthiopyrimidine To a 0° C. solution of benzimidazole (1.77 g) in 40 mL of DMF was added NaH (0.6 g) in portions. After gas evolution ceased, the cooling bath was removed and the mixture was stirred at room temperature for 10 min; then 4-chloro-2-methylthiopyrimidine (1.45 mL) was added via syringe. The mixture was heated to 80° C. and stirred for 5 h at this temperature, then cooled and poured into 100 mL of water. The phases were separated and the aqueous phase was extracted with 3×50 mL of EtOAc. The combined organics were washed with 50 mL of brine, dried over $Na_2SO_4$, and concentrated. The residue was purified by flash chromatography, eluting with a gradient system of 4:1 to 2:1 hexanes-acetone to provide 1.17 g of the title compound. Mass spectrum (ESI) 242.9 (M+1).
Step B: 2-[Benzimidazol-1-yl]-4-methanesulfonylpyrimidine The title compound was prepared from 2-(benzimidazol-1-yl)-4-ethylthiopyrimidine (1.15 g) and Oxone® (5.84 g) according to the procedure described in EXAMPLE 1, Step B. Mass spectrum (ESI) 275.1 (M+1).
Step C: 2-[Benzimidazol-1-yl]-4-[1-(1-benzyloxycarbonyl)-4-(tert-butyloxycarbonyl)-piperazine-2-yl)-ethylamino]pyrimidine The title compound was prepared from 2-(benzimidazol-1-yl)-4-methanesulfonylpyrimidine (302 mg) and 1-benzyloxycarbonyt-2-(1-aminoethyl)-4-tert-butyloxycarbonylpiperazine, diastereomer 1 (EXAMPLE 14, Step D; 400 mg) according to the procedure described in EXAMPLE 14, Step E, with the substitution of DMSO for DMF. Mass spectrum (ESI) 558.5 (M+]).
Step D: 2-[Benzimidazol-1-yl]-4-[1-(1-(benzyloxycarbonyl)-4-(N-naphth-1-y-carbamoyl)-piperazine-2-yl)ethylamino]pyrimidine The title compound was prepared from 2-[benzimidazol-1-yl]-4-f1-(1-benzyloxycarbonyl)-4-(tert-butyloxycarbonyl)-piperazine-2-yl)-ethylamino]pyrimidine (50 mg) and naphthyl isocyanate (17 mg) according to the procedure described in EXAMPLE 14, Step F. Mass spectrum (ESI) 627.8 (M+1).

Step E: 2-[Benzimidazol-1-yl]-4-[1-(1-methyl-4-(N-naphth-1-yl-carbamoyl)piperazine-2-yl)-ethylamino]pyrimidine The title compound was prepared from 2-[benzimidazol-1-yl]-4-[1-(1-(benzyloxycarbonyl)-4-(N-naphth-1-yl-carbamoyl)-piperazine-2-yl)ethylamino]pyrimidine (50 mg), 37% aqueous formaldehyde (17 μL), and NaBH$_3$CN (4.4 mg) according to the procedure described in EXAMPLE 14, Step G. Mass spectrum (ESI) 507.4 (M+1).

EXAMPLE 27

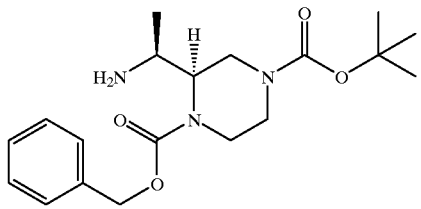

(S,S)-1-Benzyloxycarbonyl-2-(1-aminoethyl)-4-tert-butyloxycarbonylpiperazine

Step A: (S)-1-Benzyloxycarbonyl-4-tert-butyloxycarbonylpiperazine-2-(N-methyl-N-methoxy)carboxamide To a solution of (S)-piperazine-2-carboxylic acid (25 g) dissolved in 1 L of 1:1 dioxane:water at pH 11 was added a solution of [2-tert-butoxycarbonyloxyimino)-2-phenylacetonitrile] (33.35 g) in 250 mL of dioxane. The solution was maintained at pH 11 by addition of 5N NaOH and stirred for 3 hours at room temperature, then cooled to 0° C. The pH was adjusted to 9.5 using 2N HCl; then 19.3 mL of neat benzyl chloroformate was added while maintaining a pH of 9.5 with 5N NaOH. The reaction mixture was warmed to room temperature and stirred for 24 hours. The mixture was extracted with 2×500 mL of Et$_2$O. The aqueous phase was acidified to pH 2 using 2N HCl, then extracted with 4×500 mL of ethyl acetate. The combined organic extracts were washed with 500 mL of brine, dried with MgSO$_4$, and concentrated to a pale yellow oil. This oil (37 g) was dissolved in 730 mL of CH$_2$Cl$_2$. Then N,O-dimethylhydroxyl-amine, 4 g of 1-[3-(dimethylamino)propyl]-3-ethylcarbodiimide hydrochloride (2 g), triethylamine (8 mL), and 4-dimethylaminopyridine (0.461 g) were added, in that order, to the solution. After stirring for 18 hours at room temperature, the solution was poured into 800 mL of distilled water and extracted with 800 mL of CH$_2$Cl$_2$. The organic phase was washed with 400 mL each of 1N HCl and saturated Na$_2$HCO$_3$, and 800 mL of brine, and dried with Na$_2$SO$_4$, then concentrated to a yellow oil. The residue was purified by flash chromatography, eluting with 4:1→2:1→1:1 hexanes/ethyl acetate to yield 17.13 g of a colorless oil. Mass spectrum (ESI) 291.0 (M−116).

Step B: (S)-1-Benzyloxycarbonyl-2-acetyl-4-tert-butyloxycarbonylpiperazine

To a solution of (S)-1-benzyloxycarbonyl-4-tert-butyloxycarbonylpiperazine-2-(N-methyl-N-methoxy)carboxamide (17 g) in 510 mL of dry THF was added 1.4M methylmagnesium bromide in toluene (44.7 mL) dropwise at −42° C. over 15–20 minutes. The reaction mixture was stirred for an hour. Then an additional 15 mL of methylmagnesium bromide was added and the solution was stirred for another hour while warming to −20° C. The reaction was quenched by addition of 74 mL of saturated NH$_4$Cl dropwise. The mixture was warmed to 0° C.; then 56 mL of saturated NH$_4$Cl was poured into the mixture and extracted with 3×500 mL of Et$_2$O. The combined organics were washed with 500 mL of brine, dried with Na$_2$SO$_4$, then concentrated. The residue was purified by flash chromatography, eluting with 9:1 hexanes-ethyl acetate to provide 12.15 g of a yellow oil. Mass spectrum (ESI) 307.4 (M−55).

Step C: (S,R)-1-Benzyloxycarbonyl-2-(1-hydroxyethyl)-4-tert-butyloxycarbonylpiperazine Tetrahydro-1-methyl-3,3-diphenyl-1H,3H-pyrrolo[1,2-c][1,3,2]-oxazaboroleborane (6.5 g) was dissolved in 25 mL of CH$_2$Cl$_2$ and cooled to −20° C. A solution of (S)-1-benzyloxycarbonyl-2-acetyl-4-tert-butyloxycarbonyl-piperazine (8 g) dissolved in 22 mL of CH$_2$Cl$_2$ was added dropwise. The mixture was stirred for 2 hours at −20° C., then quenched with methanol and stirred overnight. Flash chromatography, eluting with 2:1 hexanes-ethyl acetate, provided 7.61 g of enantiomerically pure alcohol (HPLC: YMC chiralpak OJ, 9:1 hexanes-EtOH, 1 mL/min flow rate). Mass spectrum (ESI) 265.0 (M−99).

Step D: (S,S)-1-Benzyloxycarbonyl-2-(1-azidoethyl)-4-tert-butyloxycarbonylpiperazine (S,R)-1-benzyloxycarbonyl-2-(1-hydroxyethyl)-4-tert-butyloxycarbonyl-piperazine (7.6 g) was dissolved in 208 mL of toluene. While stirring, imidazole (3,5 g), triphenylphospine (15.31 g), and Zn(N$_3$)$_2$.pyr$_2$ (14.11 g) were added in that order. The mixture was cooled to 0° C. and diethylazodicarboxylate (10.2 g) was added dropwise. The mixture was warmed to room temperature and stirred for 1 hour, then decanted into a separatory funnel and extracted with 2×360 mL of ethyl acetate. Any solids in the reaction flask were dissolved with 1N HCl, poured into the separatory funnel, and extracted with 2×760 mL of ethyl acetate. The combined organics were washed with 760 mL each of saturated NaHCO$_3$ and brine, dried with Na$_2$SO$_4$, and concentrated. The residue was purified by flash chromatography, eluting with 4:1 hexanes-ethyl acetate to provide 4.19 g of the title compound. Mass spectrum (ESI) 334.1 (M−55).

Step E: (S,S)-1-Benzyloxycarbonyl-2-(1-aminoethyl)-4-tert-butyloxycarbonylpiperazine (S,S)-1-Benzyloxycarbonyl-2-(1-azidoethyl)-4-tert-butyloxycarbonylpiperazine (8.1 g) was dissolved in 255 mL of 9:1 THF-water and triphenylphosphine (10.9 g) was added. The mixture was heated to 75° C. and stirred at this temperature overnight. The reaction mixture was cooled, diluted with 286 mL of CH$_2$Cl$_2$, poured into 250 mL of 1N HCl, and extracted with 750 mL of CH$_2$Cl$_2$. The aqueous phase was basified to pH>10 by addition of 5N NaOH, then extracted with 5×750 mL of EtOAc. The combined organic extracts were washed with 750 mL of brine, dried over Na$_2$SO$_4$, and concentrated. The residue was purified by flash chromatography using 90:10 ethyl acetate-methanol to yield 3.07 g of the title compound. Mass spectrum (ESI) 308.3 (M−55).

EXAMPLE 28

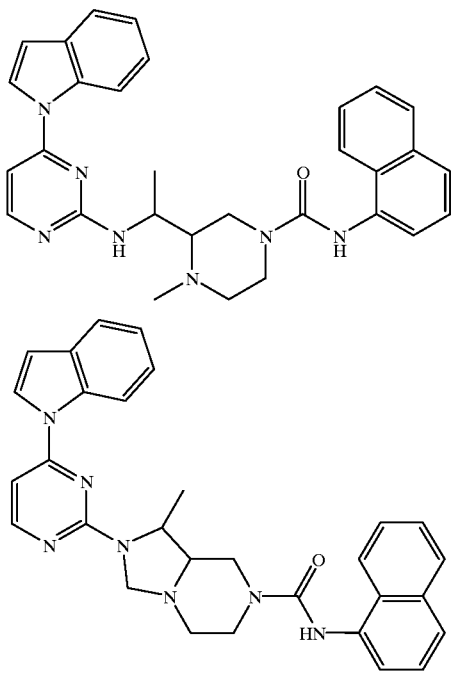

2-[1-(1-Methyl-4-(N-naphth-1-yl-carbamoyl)piperazine-2-yl)-ethylamino]-4-[indol-1-yl]pyrimidine and 2-[7-methyl-4-(N-naphth-1-yl-carbamoyl)-1,4,8-triazabicyclo-[4,3,0]nonan-8-yl]-4-[indol-1-yl]pyrimidine Step A: 2-Methanesulfonyl-4-[indol-1-yl]pyrimidine 2-Methylthio-4-[indol-1-yl]pyrimidine was prepared from indole (1.00 g), NaH (220 mg), and 4-chloro-2-methylthiopyrimidine (0.9 mL) according to the procedure described in EXAMPLE 1, Step A. The title compound was prepared from 2-[indol-1-yl]-4-methylthiopyrimidine (2.11 g) and oxone (10.5 g) according to the procedure described in EXAMPLE 1, Step B. Mass spectrum (ESI) 274.0 (M+1).

Step B: 2-[1-(1-(Benzyloxycarbonyl)-4-(tert-butyloxycarbonyl)-piperazine-2-yl)ethylamino]-4-(indol-1-yl)pyrimidine The title compound was prepared from 2-methanesulfonyl-4-[indol-1-yl]pyrimidine (125 mg) and 1-benzyloxycarbonyl-2-(1-aminoethyl)-4-tert-butyloxycarbonylpiperazine (EXAMPLE 28; 166 mg) according to the procedure described in EXAMPLE 14, Step E. Mass spectrum (ESI) 557.3 (M+1).

Step C: 2-[1-(1-(Benzyloxycarbonyl)-4-(N-naphth-1-yl-carbamoyl)-piperazine-2-yl)-ethylamino]-4-(indol-1-yl)pyrimidine The title compound was prepared from 2-[1-(1-(benzyloxycarbonyl)-4-(tert-butyloxycarbonyl)-piperazine-2-yl)-ethylamino]-4-(indol-1-yl)pyrimidine (68 mg) and naphthyl isocyanate (24 mg) according to the procedure described in EXAMPLE 14, Step F. Mass spectrum (ESI) 626.2 (M+1).

Step D: 2-[1-(1-Methyl-4-(N-naphth-1-yl-carbamoyl)-piperazine-2-yl)-ethylamino]-4-(indol-1-yl)pyrimidine and 2-[7-methyl-4-(N-naphth-1-ylcarbamoyl)-1,4,8-triazabicyclo[4,3,0]nonan-8-yl]-4-[indol-1-yl]-pyrimidine The title compounds were prepared from 2-[1-(1-(benzyloxycarbonyl)-4-(N-naphth-1-yl-carbamoyl)-piperazine-2-yl)-ethylamino]-4-(indol-1-yl)pynrmidine (42 mg) and 37% aqueous formaldehyde (22 μL), and NaBH₃CN (6 mg) according to the procedure described in EXAMPLE 14, Step G. Mass spectrum (ESI) of 2-[1-(1-methyl-4-(N-naphth-1-yl-carbamoyl)-piperazine-2-yl)-ethylamino]-4-(indol-1-yl)pyrimidine 506.5 (M+1). Mass spectrum (ESI) of 2-[7-methyl-4-(N-naphth-1-yl-carbamoyl)-1,4,8-triazabicyclo[4,3,0]nonan-8-yl]-4-[indol-1-yl]pyrimidine 504.5 (M+1).

EXAMPLE 29

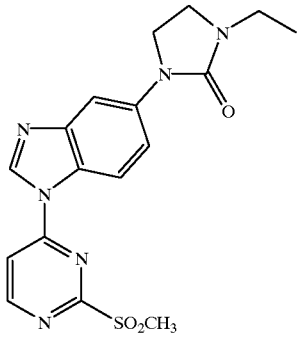

2-Methanesulfonyl-4-[5-(3-ethyl-imidazolidin-2-on-1-yl)benzimidazol-1-yl]-pyrimidine Step A: 2-(N-Tert-butyloxycarbonyl-N-ethyl)aminoethanol To a solution of 2-(ethylamino)ethanol (3 g, 33.65 mmol) in 1:1 dioxane:water at 0° C. was added triethylamine(7.04 ml, 50.48 mmol) followed by addition of 2-(tert-butoxycarbonyloxyimino)-2-phenylacetonitrile (9.9 g, 40.38 mmol). The reaction mixture was stirred at 0° C. for 10 min and then at room temperature for 2 h. The mixture was extracted with ethyl acetate (2×150 ml); the ethyl acetate layers were then combined, washed with brine and dried over sodium sulfate. Removal of the solvent and subsequent purification by column chromatography eluting with 1:2 ethyl acetate:hexane system to obtain 3.69 g of the title compound. $^1$H NMR (500 MHz, CDCl$_3$): δ3.753 (t, J=5.0 Hz, 2H); 3.39 (t, J=4.8 Hz, 2H); 3.24 (brs, 2H); 1.48 (s, 9H); 1.13 (t, J=7.1 Hz, 3H).

Step B: 2-(N-Tert-butyloxycarbonyl-N-ethyl)aminoacetaldehyde

To a mixture of oxalyl chloride (3.4 ml of 2M solution in CH$_2$Cl$_2$, 6.87 mmol) in CH$_2$Cl$_2$ (10 ml) at −78° C. was added a solution of DMSO (0.86 ml, 12.14 mmol) in CH$_2$Cl$_2$ (5 ml) slowly. The mixture was stirred at −78° C. for 20 min. To this was added a solution of 2-(N-Tert-butyloxycarbonyl-N-ethyl)aminoethanol (1.0 g, 5.28 mmol) in CH$_2$Cl$_2$ (5 ml) slowly. The reaction mixture was then stirred at −78° C. for 2 h followed by addition of triethylamine (3.7 ml, 26.4 mmol). The mixture was stirred again at −78° C. for 10 min, at 0° C. for 30 min. A mixture of methanol (1 ml) and water (8 ml) was added to the reaction; the mixture was separated. The aqueous layer was extracted with methylene chloride (3×60 ml). The combined organic layer was washed with saturated sodium bicarbonate, water, brine and dried over magnesium sulfate. Removal of the solvent provided the title compound, which was used directly for next step.

89

Step C: 2-Methylthio-4-[5-N-((N'-tert-butyloxycarbonyl-N'-ethyl)-aminoethyl)-aminobenzimidazol-1-yl]pyrimidine A mixture of the 2-methylthio-4-[5-aminobenzimidazol-1-yl]pyrimidine (EXAMPLE 3) (162 mg, 0.63 mmol) and the 2-(N-Tert-butyloxycarbonyl-N-ethyl)-aminoacetaldehyde (118 mg, 0.63 mmol) in 1,2-dichloroethane (5 mL) was stirred at room temperature for 30 min. To this was added sodium triacetoxyborohydride (155 mg, 0.693 mmol). The reaction mixture was stirred under $N_2$ at rt for 1.5 h. Removal of the solvent and subsequent silica gel column chromatography purification eluting with 2:3 acetone:hexane system provided 183 mg of the title compound. Mass spectrum (ESI): 429 (M+1). $^1$H NMR (CDCl$_3$): δ8.70 (brs, 1H); 8.61 (d, J=5.5 Hz, 1H); 8.03 (d, J=8.9 Hz, 1H); 7.20 (d, J=5.5 Hz, (d, J=5.5 Hz, 1H); 7.08 (brs, 1H); 6.87 (brs, 1H); 3.55 (brs, 2H); 3.38 (t, J=5.8Hz, 2H); 3.29 (brs, 2H); 2.68 (s, 3H); 1.51 (s, 9H); 1.14 (t, J=7.0 Hz, 3H).

Step D: 2-Methylthio-4-[5-N-((N'-ethyl)-aminoethyl)-aminobenzimidazol-1-yl]pyrimidine To a solution of 2-Methylthio-4-[5-N-((N'-tert-butyloxycarbonyl-N'-ethyl)-aminoethyl)-amino benzimidazol-1-yl]pyrimidine (140 mg, 0.327 mmol) in methylene chloride (1 ml) was added triethylsilane and then cooled to 0° C. To this was added TFA slowly; the reaction was stirred at 0° C. for 30 min, rt for 45 min. Removal of the solvent and subsequent purification by preparative thin layer chromatography eluting with 10% 2N ammonium in methanol:methylene chloride system provided 101 mg of the title compound. Mass spectrum (ESI): 329 (M+1).

Step E: 2-Methylthio-4-[5-(3-ethyl-imidazolidin-2-on-1-yl)benzimidazol-1-yl]pyrimidine To a solution of 2-Methylthio-4-[5-N-((N'-ethyl)-aminoethyl)-aminobenzimidazol-1-yl]pyrimidine (119 mg, 0.363 mmol) in DMF (2.5 ml) was added carbonyl diimidazole and triethylamine. The reaction mixture was stirred at it for 1 h, then at 100° C. for 2 days. Removal of the solvent and subsequent preparative thin layer chromatographic purification eluting with 4% 2N ammonium in methanol:methylene chloride system provided 95 mg of the title compound. Mass spectrum (ESI): 355 (M+1).

Step F: 2-Methanesulfonyl-4-[5-(3-ethyl-imidazolidin-2-on-1-yl)benzimidazol-1-yl]pyrimidine To a solution of 2-Methylthio-4-[5-(3-ethyl-imidazolidin-2-on-1-yl)benzimidazol-1-yl]pyrimidine (100 mg, 0.282 mmol) in 1:1 methanol:methylene chloride (7 ml) was added a mixture of Oxone® (520 mg, 0.846 mmol) in water (2 ml) at 0° C. The reaction mixture was stirred at it for 7 h, then diluted with methylene chloride. The mixture was separated; the aqueous layer was extracted with methylene chloride (3×50 ml). The combined methylene chloride layer was dried over magnesium sulfate. Removal of the solvent and subsequent purification by preparative thin layer chromatography eluting with 5% 2N ammonium in methanol:methylene chloride system provided 63 mg of the title compound. Mass spectrum (ESI): 387 (M+1).). $^1$H NMR (CDCl$_3$): δ8.97 (d, J=5.7 Hz, 1H); 8.71 (s, 1H); 8.26 (d, J=9.1 Hz, 1H); 8.02 (dd, J$_1$=8.9 Hz, J$_2$=2.1 Hz, 1H); 7.85 (d, J=2.0 Hz, 1H); 7.74 (d, J=5.7 Hz, 1H); 3.93 (t, J=8.0 Hz, 2H); 3.56 (t, J=8.0 Hz, 2H); 3.45 (s, 3H); 3.42 (q, J=7.3Hz, 2H); 1.23 (t, J=7.3 Hz, 3H).

90

EXAMPLE 30

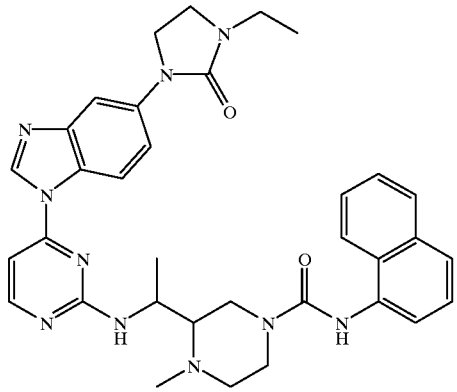

2-[1-(1-Methyl-4-(N-naphth-1-yl-carbamoyl)piperazine-2-yl)-ethylamino]-4-[5-(3-ethylimidazolidin-2-on-1-yl)benzimidazol-1-yl]pyrimidine Step A: 2-[1-(1-(Benzyloxycarbonyl)-4-(tert-butyloxycarbonyl)-piperazine-2-yl)-ethylamino]-4-[5-(3-ethyl-imidazolidin-2-on-1-yl)benzimidazol-1-yl]pyrimidine The title compound was prepared from 2-methanesulfonyl-4-[5-(3-ethyl-imidazolidin-2-on-1-yl)benzimidazol-1-yl]pyrimidine (EXAMPLE 29; 95 mg) and 1-benzyloxycarbonyl-2-(1-aminoethyl)-4-tert-butyloxycarbonylpiperazine, diastereomer 1 (EXAMPLE 14 Step D; 100 mg) according to the procedure described in EXAMPLE 14, Step E. Mass spectrum (ESI) 670.5 (M+1).

Step B: 2-[1-(1-(Benzyloxycarbonyl)-4-(N-naphth-1-yl-carbamoyl)-piperazine-2-yl)-ethylamino]-4-[5-(3-ethyl-imidazolidin-2-on-1-yl)benzimidazol-1-yl]pyrimidine The title compound was prepared from 2-[1-(1-(benzyloxycarbonyl)-4-(tert-butyloxycarbonyl)-piperazine-2-yl)-ethylamino]-4-[5-(3-ethyl-imidazolidin-2-on-1-yl)benzimidazol-1-yl]pyrimidine (35 mg) and naphthyl isocyanate (10 mg) according to the procedure described in EXAMPLE 14, Step F. Mass spectrum (ESI) 739.5 (M+1).

Step C: 2-[1-(1-Methyl-4-(N-naphth-1-yi-carbamoyl)-piperazine-2-yl)-ethylamino]-4-[5-(3-ethyl-imidazolidin-2-on-1-yl)benzimidazol-1-yl]pyrimidine The title compound was prepared from 2-[1-(1-(benzyloxycarbonyl)-4-(N-naphth-1-yl-carbamoyl)-piperazine-2-yl)-ethylamino]-4-[5-(3-ethyl-imidazolidin-2-on-1-yl)benzimidazol-1-yl]pyrimidine (28 mg), 37% aqueous formaldehyde (19 µL), and NaBH$_3$CN (4.8 mg) according to the procedure described in EXAMPLE 14, Step G. Mass spectrum (ESI) 619.3 (M+1).

EXAMPLE 31

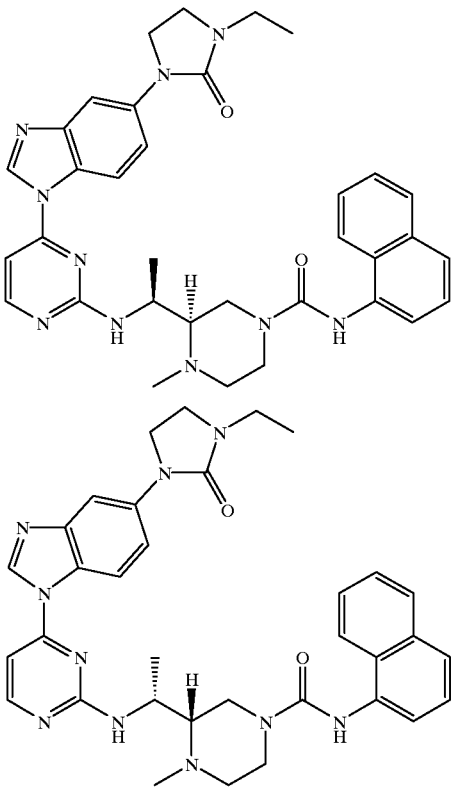

(S,S)-2-[1-(1-Methyl-4-(N-naphth-1-yl-carbamoyl) piperazine-2-yl)-ethylamino]-4-[5-(3-ethyl-imidazolidin-2-on-1-yl)benzimidazol-1-yl]pyrimidine and (R,R)-2-[1-(1-Methyl-4-(N-naphth-1-yl-carbamoyl)piperazine-2-yl)-ethylamino]-4-[5-(3-ethyl-imidazolidin-2-on-1-yl)benzimidazol-1-yl]pyrimidine The two enantiomers of racemic 2-[1-(1-methyl-4-(N-naphth-1-yl-carbamoyl)piperazine-2-yl)-ethylamino]-4-[5-(3-ethyl-imidazolidin-2-on-1-yl)benzimidazol-1-yl] pyrimidine (EXAMPLE 31, Step C) were separated by HPLC on a YMC Chiralpak AD 20×250 mm column, eluting with 50% EtOH-hexanes at 9 mL/min.

(S,S)-2-[1-(1-Methyl-4-(N-naphth-1-yl-carbamoyl) piperazine-2-yl)-ethylamino]-4-[5-(3-ethyl-imidazolidin-2-on-1-yl)benzimidazol-1-yl]pyrimidine $^1$H NMR (500 MHz, CDCl$_3$): δ8.56 (br s, 1H); 8.32 (br s, 1H); 7.95–8.15 (m, 2H); 7.72–7.85 (m, 2H); 7.55–7.68 (m, 3H); 7.32–7.48 (m, 3H); 6.84 (br s, 1H); 6.70–6.80 (m, 1H); 5.82 (br s, 1H); 4.50–4.60 (m, 1H); 4.08 (br d, J=12.5 Hz, 1H); 3.80–3.95 (m, 3H); 3.51 (t, J=8 Hz, 2H); 3.38 (q, J=7 Hz, 2H); 3.10–325 (m, 1H); 3.00–3.10 (m, 1H); 2.89 (br d, J=10 Hz, 1H) 2.35–2.58 (m, 5H); 1.35 (d, J=7.5 Hz, 3H); 1.19 (t, J=7.5 Hz, 3H). Mass spectrum (ESI) 619.7 (M+1).

(R,R)-2-[1-(1-Methyl-4-(N-naphth-1-yl-carbamoyl) piperazine-2-yl)-ethylamino]-4-[5-3-ethyl-imidazolidin-2-on-1-yl)benzimidazol-1-yl]pyrimidine $^1$H NMR (500 MHz, CDCl$_3$): δ8.56 (br s, 1H); 8.34 (br s, 1H); 8.00–8.20 (m, 2H); 7.70–7.85 (m, 2H); 7.55–7.68 (m, 3H); 7.32–7.50 (m, 3H); 6.70–6.85 (m, 2H); 5.64 (br s, 0.7H); 4.50–4.60 (m, 1H); 4.07 (br d, J=9 Hz, 1H); 3.80–3.95 (m 3H); 3.52 (t, J=8.5 Hz, 2H); 3.39 (q, J=7.5 Hz, 2H); 3.10–3.25 (m, 1H); 3.00–3.10 (m, 1H), 2.92 (br d, J=10 Hz, 1H) 2.35–2.58 (m, 5H); 1.36 (d, J=7 Hz, 3H); 1.19 (t, J=7.5 Hz, 3H). Mass spectrum (ESI) 619.6 (M+1).

EXAMPLE 32

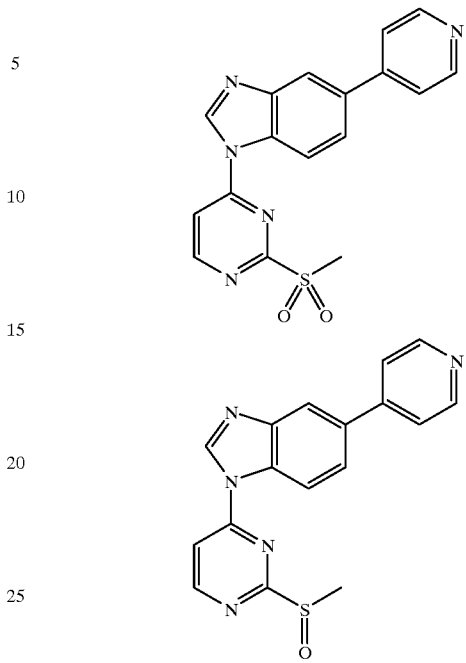

2-Methylsulfonyl-4-[5-(pyridin-4-yl)-benzimidazol-1-yl] pyrimidine and 2-Methylsulfoxide-4-[5-(pyridin-4-yl)-benzimidazol-1-yl]pyrimidine Step A: 2-Methylthio-4-[5-iodobenzimidazol-1-yl] pyrimidine 2-Methylthio-4-[5-aminobenzimidazol-1-yl]pyrimidine (EXAMPLE 3, 513 mg) was dissolved in diiodomethane (5 mL), isoamylnitrite (0.32 mL) was added and the resulting solution was heated to 100° C. for 30 minutes. Upon cooling to rt, the reaction mixture was directly purified by column chromatography (SiO$_2$, 5% MeOH in CH$_2$Cl$_2$) to yield 342 mg of the title compound. Mass spectrum 371.1 (ESI) (M+).

Step B: 2-Methylthio-4-[5-trimethylstannylbenzimidazol-1-yl]pyrimidine

2-Methylthio-4-[5-iodobenzimidazol-1-yl]pyrimidine (342 mg), hexamethylditin (0.4 mL), and Pd(Ph$_3$P)$_4$ (25 mg) were dissolved in toluene (8 mL) and heated to 100° C. for 1 hour. Upon cooling to rt, the reaction mixture was directly purified by column chromatography (SiO$_2$, 5% MeOH in CH$_2$Cl$_2$) to yield 310 mg of 2-methylthio-4-[5-trimethylstannyl-benzimidazol-1-yl]pyrimidine. Mass spectrum 407.0 (ESI) (M+1).

Step C: 2-Methylthio-4-[5-(pyridin-4-yl)benzimidazol-1-yl] pyrimidine

2-Methylthio-4-[5-trimethylstannyl-benzimidazol-1-yl] pyrimidine (150 mg), 4-bromopyridine (180 mg), tri-o-tolylphosphine (5 mg) and tris(dibenzylidineacetone) dipalladium(0) (7.5 mg) were dissolved in DMF (3 mL) and heated to 100° C. for 1 hour. Upon cooling to rn and evaporation of solvent, the reaction residue was directly purified by column chromatography (SiO$_2$,5% MeOH in CH$_2$Cl$_2$) to yield 100 mg of the title compound. Mass spectrum (ESI) 320.2 (M+1).

Step D: 2-Methylsulfonyl-4-[5-(pyridin-4-yl)-benzimidazol-1-yl]pyrimidine and 2-Methylsulfoxide-4-[5-(pyridin-4-yl)-benzimidazol-1-yl]-pyrimidine [1:1 mixture]

2-Methylthio-4-[5-(pyridin-4-yl)-benzimidazol-1-yl] pyrimidine (25 mg) was dissolved in methylene chloride (2 mL) and cooled to 0 C. 3-Chloroperoxybenzoic acid (50–60%, 27 mg) was added and the reaction mixture was allowed to warm to rt over 2 hours. The solution was then diluted with water and extracted with EtOAc. The combined organic extracts were then dried (MgSO$_4$) and concentrated under reduced pressure. The residue was purified with preparatory thin-layer chromatography (SiO2, 5% MeOH in CH$_2$Cl$_2$) to yield 14 mg of a 1:2 mixture of the title compounds. Mass spectrum (ESI) 351.1 (M+) and 335.1 (M+) respectively.

EXAMPLE 33

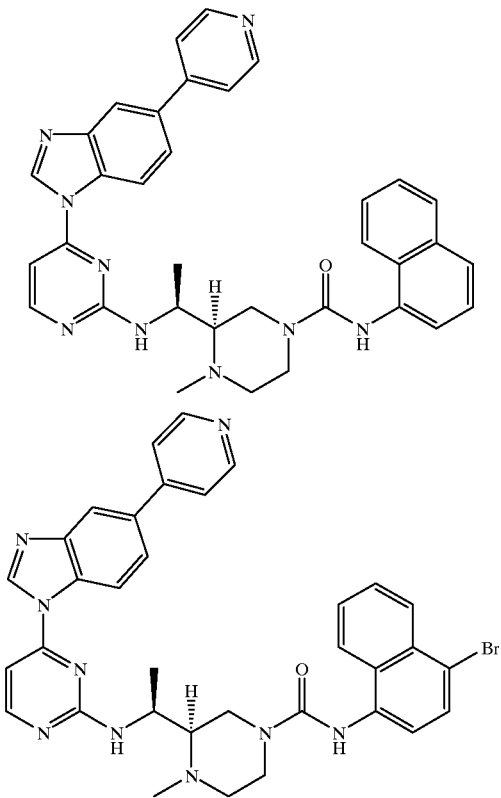

(S,S)-2-[1-(1-Methyl-4-(N-naphth-1-yl-carbamoyl) piperazine-2-yl)ethylamino]-4-[5-pyridin-4-yl) benzimidazol-1-yl]pyrimidine and (S,S)-2-[1-(1-Methyl-4-(N-(4-bromo)naphth-1-yl-carbamoyl)piperazine-2-yl) ethylamino]-4-[5-(pyridin-4-yl)benzimidazol-1-yl] pyrimidine Step A: (S,S)-2-[1-(1-(Benzyloxycarbonyl)-4-(tert-butyloxycarbonyl)piperazine-2-yl)-ethylamino]-4-[5-(pyridine-4-yl)benzimidazol-1-yl]pyrimidine The title compound was prepared from 2-methanesulfoxide-4-[5-(pyridin-4-yl)benzimidazol-1-yl] pyrimidine (EXAMPLE 32; 17 mg) and (S,S)-1-benzyloxycarbonyl-2-(1-aminoethyl)-4-tert-butyloxycarbonylpiperazine (EXAMPLE 27; 18 mg) according to the procedure described in EXAMPLE 14, Step E. Mass spectrum (ESI) 635.5 (M+1).

Step B: (S,S)-2-[1-(1-(Benzyloxycarbonyl)-4-(N-naphth-1-yl-carbamoyl)piperazine-2-yl)-ethylamino]-4-[5-(pyridin-4-yl)benzimidazol-1-yl]pyrimidine The title compound was prepared from (S,S)-2-[1-(1-(benzyloxycarbonyl)-4-(tert-butyloxycarbonyl)piperazine-2-yl)-ethylamino]-4-[5-(pyridine-4-yl)benzimidazol-1-yl] pyrimidine (72 m,) and naphthyl isocyanate (23 mg) according to the procedure described in EXAMPLE 14, Step F. Mass spectrum (ESI) 704.2 (M+1).

Step C: (S,S)-2-[1-(1-Methyl-4-(N-naphth-1-yl-carbamoyl) piperazine-2-yl)-ethylamino]-4-[5-(pyridin-4-yl) benzimidazol-1-yl]pyrimidine and (S,S)-2-[1-(-Methyl-4-(N-(4-bromo)-naphth-1-yl-carbamoyl)piperazine-2-yl) ethylamino]-4-[5-(pyridin-4-yl)-benzimidazol-1-yl] pyrimidine The title compounds were prepared from (S,S)-2-[1-(1-(benzyloxycarbonyl)-4-(N-naphth-1-yl-carbamoyl)-piperazine-2-yl)-ethylamino]-4-[5-(pyridin-4-yl) benzimidazol-1-yl]pyrimidine (45 mg), 37% aqueous formaldehyde (31 μL), and NaBH$_3$CN (8 mg) according to the procedure described in EXAMPLE 14, Step G. The major product (S,S)-2-[1-(1-methyl-4-(N-naphth-1-yl-carbamoyl)piperazine-2-yl)-ethylamino]-4-[5-(pyridin-4-yl )benzimidazol-1-yl]pyrimidine was separated from the minor product (S,S)-2-[1-(1-methyl-4-(N-(4-bromo)-naphth-1-yl-carbamoyl)piperazine-2-yl)-ethylamino]-4-[5-(pyridin-4-yl)benzimidazol-1 -yl]pyrimidine by HPLC on an octadecylsilica 10×250 mm column, eluting with 75:25 MeOH—H$_2$O at 4 mL/min.

(S,S)-2-[1-(1-Methyl-4-(N-naphth-1-yl-carbamoyl) piperazine-2-yl)-ethylamino]-4-[5-(pyridin-4-yl) benzimidazol-1-yl]pyrimidine $^1$H NMR (500 MHz, CDCl$_3$): δ8.68 (dd, J=1.5, 4.5 Hz, 2H); 8.64 (s, 1H); 8.38 (d, J=5 Hz, 1H); 8.24 (d, J=8.5 Hz, 1H); 8.11 (br s, 1H); 7.76–7.82 (m, 2H); 7.54–7.66 (m, 5H); 7.34–7.45 (m, 3H); 6.78 (d, J=5 Hz, 1H); 6.74 (s, 1H); 5.80 (br s, 0.5H); 4.50–4.60 (m, 1H); 4.10 (br d, J=12 Hz, 1H); 3.87 (br d, J=12.5 Hz, 1H); 3.25 (br t, J=11 Hz, 1H); 3.10 (dd, J=9.5, 13 Hz, 1H); 2.93 (br d, J=12 Hz, 1H) 2.44–2.60 (m, 5H); 1.37 (d, J=6.5 Hz, 3H). Mass spectrum (ESI) 584.6 (M+1).

(S,S)-2-[1-(1-Methyl-4-(N-(4-bromo)naphth-1-yl-carbamoyl)piperazine-2-yl)-ethylamino]-4-[5-(pyridin-4-yl) benzimidazol-1-yl]pyrimidine $^1$H NMR (500 MHz, CDCl$_3$): δ8.68 (d, J=6.2 Hz, 2H); 8.65 (s, 1H); 8.39 (br d, J=5 Hz, 1H); 8.24 (d, J=8.7 Hz, 1H); 8.20 (d, J=8.5 Hz, 1H); 8.12 (s, 1H); 7.78 (d, J=8 Hz, 1H); 7.68 (d, J=8.2 Hz, 1H); 7.64 (dd, J=1.6, 8.5 Hz, 1H); 7.44–7.60 (m, 5H); 6.80 (d, J=5.5 Hz, 1H); 6.65 (s, 1H); 5.66 (br s, 1H); 4.50–4.60 (m, 1H); 4.10–4.20 (m, 1H); 3.88 (br d, J=13 Hz, 1 H); 3.28 (br t, J=9 Hz, 1H); 3.15 (dd, J=10, 13 Hz, 1H); 2.96 (br d, J=12 Hz, 1H) 2.45–2.60 (m, 5H); 1.39 (d, J=7 Hz, 3H). Mass spectrum (ESI) 662.4 (M+1).

EXAMPLE 34

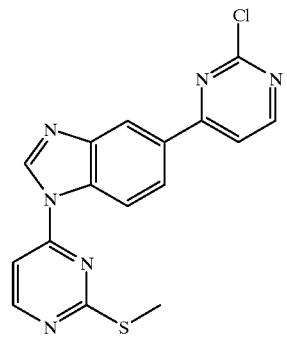

2-Methylthio-4-[5-(2-chloropyrimidin-4-yl)benzimidazol-1-yl]pyrimidine

Step A: 2-Methylthio-4-[5-pinacolatoboronyl) benzimidazol-1-yl]pyrimidine

2-Methylthio-4-[5-iodobenzimidazol-1-yl]pyrimidine (308 mg), bis-pinacolatodiboron (233 mg), potassium acetate (246 mg), and [1,1'-bis(diphenylphosphino)ferrocene]dichloropalladium(II) complex with dichloromethane (1:1) (16 mg) were dissolved in degassed DMSO (14 mL) and the resulting solution was stirred at 80° C. under argon atmosphere for 15 hours. Upon cooling to room temperature the reaction mixture was diluted with water, washed with Et$_2$O and the combined organic layer was washed with brine, dried over MgSO$_4$ and evaporated. The residue was purified by silica gel chromatography (5% MeOH/CH$_2$Cl$_2$) to yield 75 mg of the title compound. Mass spectrum (ESI) 369.0 (M+).

Step B: 2-Methylthio-4-[5-(2-chloropyrimidin-4-yl)-benzimidazol-1-yl]-pyrimidine 2-Methylthio-4-[5-pinacolatoboronyl)-benzimidazol-1-yl]pyrimidine (500 mg) was dissolved in 25 mL THF plus 3.5 mL water degassed with argon. Potassium carbonate (373 mg), 2,4-dichloropyrimidine (402 mg) and [1,1'-bis(diphenylphosphino)ferrocene]dichloropalladium(II) complex with dichloromethane (1:1) (50 mg) were added and the resulting reaction mixture heated to 90° C. and stirred for 15 hours. Upon cooling to room temperature the reaction mixture was diluted with water, washed with EtOAc and the combined organic layers were washed with brine, dried over MgSO$_4$ and evaporated. The residue was purified by preparative thin-layer silica gel chromatography (5% MeOH/CH$_2$Cl$_2$) to yield 210 mg of the title compound. Mass spectrum (ESI) 355.2 (M+1).

EXAMPLE 35

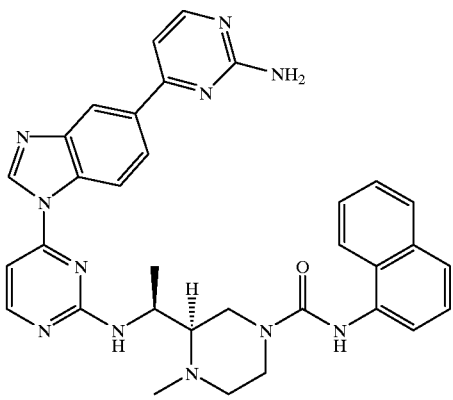

(S,S)-2-[1-(1-Methyl-4-(N-naphth-1-yl-carbamoyl)piperazine-2-yl)-ethylamino]-4-[5-(2-amino-pyrimidin-4-yl)benzimidazol-1-yl]pyrimidine Step A: 2-Methylthio-4-[5-(2-(2,4,6-trimethoxy-benzylamino)-pyrimidin-4-yl)benzimidazol-1-yl]pyrimidine A suspension of 2-methylthio-4-[5-(2-chloro-pyrimidin-4-yl)benzimidazol-1-yl]pyrimidine (EXAMPLE 34; 85 mg), 2,4,6-trimethoxybenzylamine hydrochloride (160 mg), and diisopropylethylamine (210 mL) in 3 mL of DMSO was heated to 100° C., at which point all solids were dissolved. The mixture was stirred at 100° C. for 20 h, then cooled and diluted with 15 mL of 1:1 EtOAc-Et$_2$O, washed with 2×5 mL of water and 5 mL of brine, dried over Na$_2$SO$_4$ and concentrated. The residue was purified by preparative thin-layer chromatography) eluting with 95:5 CH$_2$Cl$_2$—MeOH to provide 98 mg of the title compound. Mass spectrum (ESI) 516.4 (M+1).

Step B: 2-Methanesulfoxide-4-[5-(2-(2,4,6-trimethoxy-benzylamino)pyrimidin-4-yl)benzimidazol-1-yl]pyrimidine The title compound was prepared from 2-methylthio-4-[5-(2-(2,4,6-trimethoxy-benzylamino)-pyrimidin-4-yl)benzimidazol-1-yl]pyrimidine (98 mg) and Oxone® (350 mg) according to the procedure described in EXAMPLE 1, Step B, with the addition of DMF as co-solvent. Mass spectrum (ESI) 532.4 (M+1).

Step C: (S,S)-2-[1-(1-(Benzyloxycarbonyl)-4-(tert-butyloxycarbonyl)piperazine-2-yl)-ethylamino]-4-[5-(2-(2,4,6-trimethoxy-benzylamino)pyrimidin-4-yl)benzimidazol-1-yl]pyrimidine The title compound was prepared from 2-methanesulfoxide-4-[5-(2-(2,4,6-trimethoxy-benzylamino)-pyrimidin-4-yl)benzimidazol-1-yl]pyrimidine (25 mg) and (S,S)-1-benzyloxycarbonyl-2-(1-aminoethyl)-4-tert-butyloxycarbonylpiperazine (EXAMPLE 27; 17 mg) according to the procedure described in EXAMPLE 14, Step E, with the substitution of DMSO for DMF as solvent. Mass spectrum (ESI) 831.5 (M+1).

Step D: (S,S)-2-[1-(1-(Benzyloxycarbonyl)-4-(N-naphth-1-yl-carbamoyl)piperazine-2-yl)-ethylamino]-4-[5-(2-amino-pyrimidin-4-yl)-benzimidazol-1-yl]pyrimidine The title compound was prepared from (S,S)-2-[1-(1-(benzyloxycarbonyl)-4-(tert-butyloxycarbonyl)-piperazine-2-yl)-ethylamino]-4-[5-(pyridine-4-yl)benzimidazol-1-yl]pyrimidine (15 mg) and naphthyl isocyanate (4 mg) according to the procedure described in EXAMPLE 14, Step F. Mass spectrum (ESI) 720.6 (M+1).

Step E: 2-[1-(1-Methyl-4-(N-naphth-1-yl-carbamoyl)-piperazine-2-yl)-ethylamino]-4-[5-(2-amino-pyrimidin-4-yl)benzimidazol-1-yl]pyrimidine The title compound was prepared from (S,S)-2-[1-(1-(benzyloxycarbonyl)-4-(N-naphth-1-yl-carbamoyl)-piperazine-2-yl)-ethylamino]-4-[5-(2-amino-pyrimidin-4-yl)benzimidazol-1-yl]pyrimidine (5.5 mg), 37% aqueous formaldehyde (0.7 µL), and NaBH$_3$CN (1 mg) according to the procedure described in EXAMPLE 14, Step G. $^1$H NMR (500 MHz, CDCl$_3$): δ8.64 (s, 1H); 8.47 (d, J=1.5 Hz, 1H); 8.34–8.41 (m, 2H); 8.20 (d, J=8.5 Hz, 1H); 8.09 (dd, J=1.6, 8.5 Hz, 1H); 7.76–7.83 (m, 2H); 7.61 (t, J=7.1 Hz, 2H); 7.37–7.55 (m, 3H); 7.12 (d, J=5.5 Hz, 1H); 6.78 (d, J=5,5 Hz, 1H); 5.77 (br s, 1H); 5.13 (s, 2H); 4.50–4.60 (m, 1H); 4.09 (br d, J=12 Hz, 1H); 3.88 (br d, J=12 Hz, 1H); 3.20 (br t, J=11 Hz, 1H); 3.09 (dd, J=10, 13 Hz, 1H); 2.92 (br d, J=12 Hz, 1H) 2.40–2.60 (m, 5H); 1.36 (d, J=6.5 Hz, 3H). Mass spectrum (ESI) 431.2 (M-(N-naphthyl carbamoyl)+1).

EXAMPLE 36

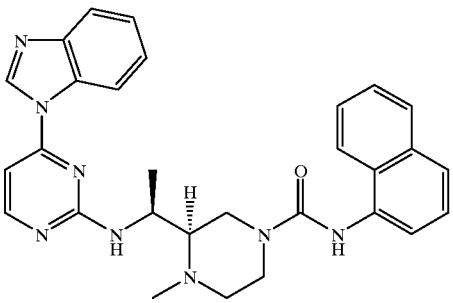

(S,S)-2-[1-(1-Methyl-4-(N-naphth-1-yl-carbamoyl)piperazine-2-yl)-ethylamino]-4-[benzimidazol-1-yl]pyrimidine Step A: (S,S)-2-[1-(1-(Benzyloxycarbonyl)-4-(tert-butyloxycarbonyl)piperazin-2-yl)-ethylamino]-4-[benzimidazol-1-yl]pyrimidine The title compound was prepared from (S,S)-1-benzyloxy-carbonyl-2-(1-aminoethyl)-4-tertbutyloxycarbonylpiperazine (Example 27; 75 mg) and 2-methanesulfonyl-4-[benzimidazol-1-yl]pyrimidine (Example 1, Step B; 100 mg) according to the procedure described in Example 14, Step E. Mass spectrum (ESI) 558.5 (M+1).

Step B: (S,S)-2-[1-(1-(Benzyloxycarbonyl)-4-(N-naphth-1-yl-carbamoyl)piperazin-2 yl)ethylamino]-4[benzimidazol-1-yl]pyrimidine The title compound was prepared from (S,S)-2-[1-(1-(benzyloxycarbonyl)-4-(tert-butyloxycarbonyl)-piperazin-2-yl)-ethylamino]-4-[benzimidazol-1-1-yl]pyrimidine (66 mg) and naphthyl isocyanate (22.9 mg) according to the procedure described in Example 14, Step F. Mass spectrum (ESI) 627.3 (M+1).

Step C: (S,S)-2-[1-(4-(N-Naphth-1-yl-carbamoyl) piperazine-2-yl)ethylamino]-4-[benzimidazol 1-yl]pyrimidine To a solution of (S,S)-2-[1-(1-(benzyloxycarbonyl)-4-(N-naphth-1-yl-carbamoyl)piperazin-2-yl)ethylamino]-4-[benzi midazol-1-yl]pyrimidine (24 mg) dissolved in 2 mL of CH$_2$Cl$_2$ and cooled to 0° C. was added 1 mL of 30% HBr/AcOH. The reaction mixture was stirred for 10 minutes at 0° C., then stirred for an additional 2 hours while warming to room temperature. The mixture was diluted with 5 mL of water and extracted with 2×5 mL of CH$_2$Cl$_2$. The aqueous layer was basified to pH 11 using 5N NaOH and extracted with 5×5 mL of ethyl acetate while maintaining a pH of 11. The combined organic phases were washed with 10 nL of brine, dried with Na$_2$SO$_4$, and concentrated to provide 9.6 mg the title compound. Mass spectrum (ESI) 493.3 (M+1).

Step D: (S,S)-2-[1-(1-Methyl-4-(N-naphth-1-yl-carbamoyl)piperazine-2-yl)ethylaminol-4-[benzimidazol 1-yl]pyrimidine The title compound was prepared from (S,S)-2-[1-(4-(N-naphth-1-yl-carbamoyl)piperazline-2-y)-ethylamino]-4-[benzimidazol-1-yl]pyrimidine (9 mg), 37% aqueous formaldehyde (3.3 mg), and NaBH$_3$CN (2.3 mg) according to the procedure described in Example 14, Step G. $^1$H NMR (500 MHz, CDCl$_3$) δ8.59 (s, 1H), 8.31 (s, 1H), 8.12 (s, 1H), 7.84–7.79 (m, 3H), 7.61–7.57 (m, 2H), 7.40–7.36 (m, 4H), 6.89 (br s, 1H), 6.76 (s, 1H), 6.08 (br s, 1H), 4.56 (s, 1H), 4.09 (d, J=11 Hz, 1H), 3.907 (d, J=10 Hz, 1H), 3.15 (m, 1H), 3.039 (t, J=10.5 Hz, 1H), 2.88 (d, J=9, 1H), 2.48–2.41 (m, 5H), 1.33 (s, 3H). Mass spectrum (ESI) 507.4 (M+1).

EXAMPLE 37

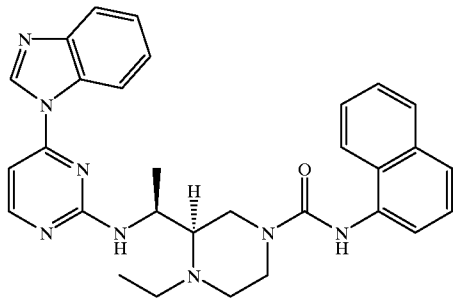

(S,S)-2-[1-(1-Ethyl-4-(N--naphth-1-yl-carbamoyl) piperazine-2-yl)-ethylamino]-4-[benzimidazol-1-yl]pyrimidine The title compound was prepared from (S,S)-2-[1-(4-(N-naphth-1-yl-carbamoyl)-piperazin-2-yi)-ethylamino]-4-[benzimidazol-1-yl]pyrimidine (EXAMPLE 36, Step C; 9 mg), acetaldehyde (5 mg), and sodium cyanoborohydride (2.3 mg) according to the procedure described in Example 14, Step G. Mass spectrum (ESI) 521.5 (M+1).

EXAMPLE 38

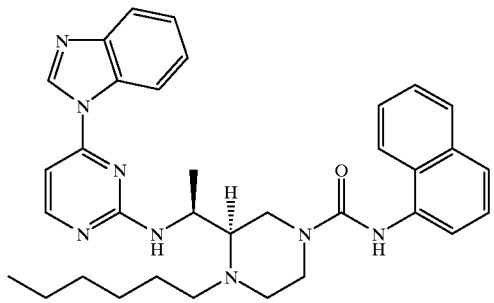

(S,S)-2-[1-(1-Hexyl4-(N naphth-1-yl-carbamoyl) piperazine-2yl)ethylamino4-[benzimidazol-1-yl]pyrimidine The title compound was prepared from (S,S)-2-[1-(4-(N-naphth-1-yl-carbamoyl)-piperazin-2-yi)-ethylamino]-4-[benzimidazol-1-yl]pyrimidine (EXAMPLE 36, Step C; 10 mg,), hexanol (12.2 mg), and sodium cyanoborohydride (3 mg) according to the procedure described in Example 14, Step G. Mass spectrum (ESI) 577.4 (M+1).

EXAMPLE 39

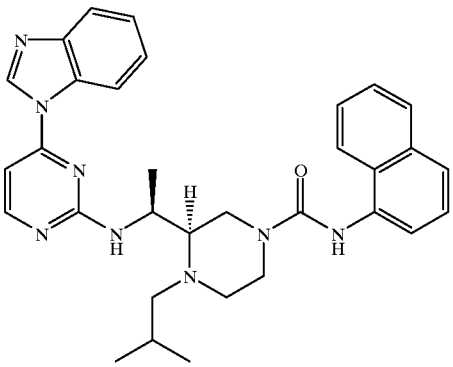

(S,S)-2-[1-(1 (2-Methylpropyl)4-(N-naphth-1-ylcarbamoyl) piperazine -2-yl)-ethylamino]-4-[benzimidazol-1]pyrimidine The title compound was prepared from (S,S)-2-[1-(4-(N-naphth-1-yl-carbamoyl)piperazin-2-yl)ethylamino]-4-[benzimidazol-1-yl]pyrimidine (EXAMPLE 36, Step C; 12 mg), isobutyraldehyde (10.5 mg), and sodium cyanoborohydride (3 mg) according to the procedure described in Example 14, Step G. Mass spectrum (ESI) 549.4 (M+1).

EXAMPLE 40

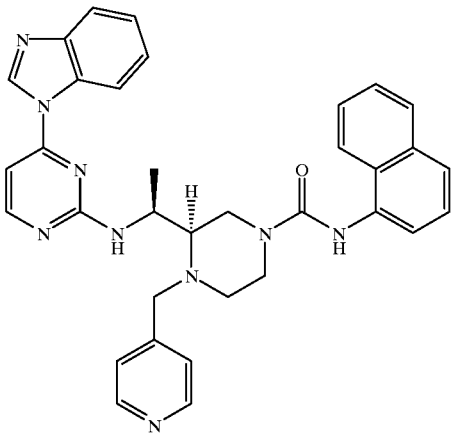

(S,S)-2-[1-(1-(pyridin-4-yl-methyl)-4-(N-naphth-1-yl-carbamoyl)piperazine-2-yl)ethylamino]-4-[benzimidazol-1-yl]pyrimidine The title compound was prepared from (S,S)-2-[1-(4-(N-naphth-1-yl-carbamoyl)-piperazin-2-yl)-ethylamino]-4-[benzimidazol-1-yl]pyrimidine (EXAMPLE 36, Step C; 12.5 mg), 4-pyridinecarboxaldehyde (16.4 mg), and sodium cyanoborohydride (3.1 mg) according to the procedure described in Example 14, Step G. Mass spectrum (ESI) 585.0 (M+2).

EXAMPLE 41

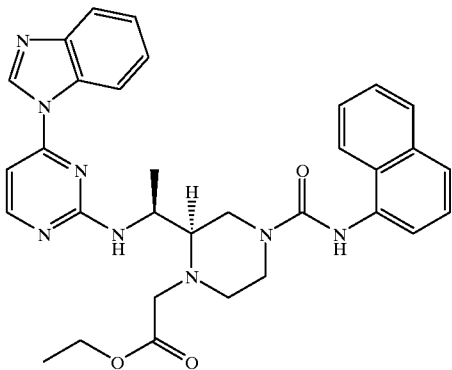

(S,S)-2-[1-(1-(ethoxycarbonylmethyl)-4-(N-naphth-1-yl-carbamoyl)piperazine-2-yl)ethylamino]-4-[benzimidazol-1-yl]pyrimidine To a solution of 2-[1-(4-(N-naphth-1-yl-carbamoyl)-piperazin-2-yl)ethylamino]-4-[benzimidazol-1-yl]pyrimidine (EXAMPLE 36, Step C; 26 mg) in 0.5 mL of acetone was added potassium carbonate (11 mg) and ethyl bromoacetate (13.2 mg). The solution was stirred for 48 hours at room temperature, then diluted with 0.5 mL of water and extracted with 3×0.5 mL of $CH_2Cl_2$. The combined organics were washed with 1 mL of brine, dried with $Na_2SO_4$, and concentrated. The residue was purified by preparative HPLC (60:40 95% $H_2O$-5% TFA:95% $CH_3CN$-5% TFA) followed by preparative thin-layer chromatography, eluting with 95:5 25 $CHCl_3$-isopropanol to provide 8.7 mg of the title compound. Mass spectrum (ESI) 579.3 (M+1).

EXAMPLE 42

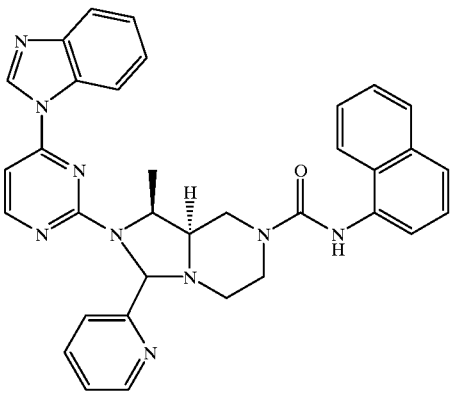

(S,S)-2-[7-methyl-4-(N-naphth-1-yl-carbamoyl)-9-(pyridin-2-yl)-1,4,8-triazabicyclo[4,3,0]nonan-8-yl]-4-[benzimidazol-1-yl]-pyrimidine The title compound was prepared from 2-[1-(4-(N-naphth-1-yl-carbamoyl)-piperazin-2-yl)-ethylamino]-4-[benzimidazol-1-yl]pyrimidine (EXAMPLE 36, Step C; 18.8 mg), 2-pyridinecarboxaldehyde (24.5 mg), and sodium cyanoborohydride (4.8 mg) according to the procedure described in Example 14, Step G. Mass spectrum (ESI) 582.2 (M+1).

EXAMPLE 43

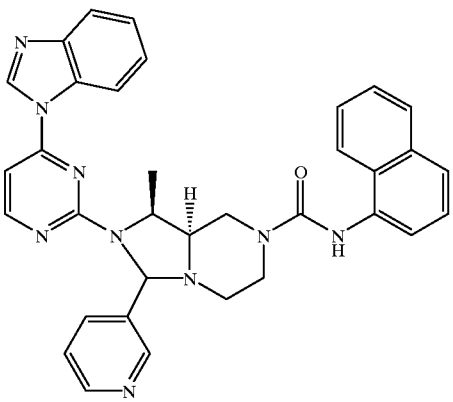

(S,S)-2-[7-methyl-4-(N-naphth-1-yl-carbamoyl)-9-(pyridin-3-yl)-1,4,8-triazabicyclo-[4.3.0]nonan-8-yl]-4-[benzimidazol-1-yl]-pyrimidine The title compound was prepared from 2-[1-(4-(N-naphth-1-yl-carbamoyl) piperazin-2-yl)-ethylamino]-4-[benzimidazol-1-yl]pyrimidine (EXAMPLE 36, Step C; 18.2 mg), 3-pyridinecarboxaldehyde (23.7 mg), and sodium cyanoborohydride (4.6 mg) according to the procedure described in Example 14, Step G. Mass spectrum (ESI) 582.2 (M+1).

EXAMPLE 44

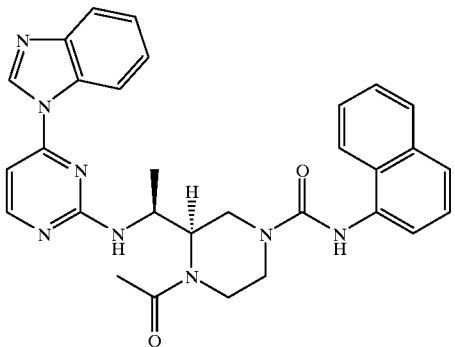

(S,S)2-[1(1-acetyl-4-(N-naphth-1-yl-carbamoyl)piperazine-2-yl)-ethylamino]-4-benzimidazol-1-yl]pyrimidine To a solution of 2-[1-(4-(N-naphth-1-yl-carbamoyl)-piperazin-2-yl)ethylamino]-4-[benzimidazol-1-yl]pyrimidine (EXAMPLE 36, Step C; 19 mg) dissolved in 2 mL of $CH_2Cl_2$ and 0.5 mL of pyridine was added 7.9 mg of acetic anhydride. The solution was stirred for 30 minutes at room temperature, then diluted with 3 mL of ethyl acetate and extracted with 3 mL of saturated $Na2HCO_3$. The organic phase was concentrated and co-concentrated with 2×1.5 mL of heptane. The residue was purified by preparative thin-layer chromatography, eluting with 9:1 $CH_3Cl$-isopropanol to provide 6.4 mg of the title compound. Mass spectrum (ESI) 535.5 (M+1).

What is claimed is:

1. A compound of Formula I

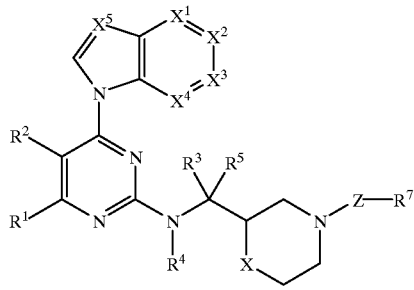

or pharmaceutically acceptable salts, hydrates, solvates, crystal forms and individual diastereomers thereof, wherein $R^1$ and $R^2$ are independently:
  a) H,
  b) halo(Br, Cl, I, or F),
  c) OH,
  d) SH,
  e) CN,
  f) $NO_2$,
  g) $R^9$,
  h) $OR^9$,
  i) $O(C=O)R^9$,
  j) $O(C=O)OR^9$,
  k) $O(C=O)NHR^9$,
  l) $O(C=O)NR^9R^{10}$,
  m) $SR^9$,
  n) $S(O)R^9$,
  o) $S(O)_2R^9$,
  p) $C(=O)R^9$,
  q) $C(=O)OR^9$,
  r) $C(=O)NHR^9$,
  s) $C(=O)NR^9R^{10}$,
  t) $NH_2$,
  u) $NHR^9$,
  v) $NR^9R^{10}$,
  w) $NHC(=O)R^9$,
  x) $NHC(=O)OR^9$,
  y) $NR^9C(=O)R^{10}$,
  z) $NR^9C(=O)NHR^{10}$,
  aa) $NR^9C(=O)NR^{10}R^{11}$,
  ab) $SO_2NHR^9$,
  ac) $SO_2NR^9R^{10}$,
  ad) $NHSO_2R^9$,
  ae) $NR^9SO_2R^{10}$, or
  af) $R^1$ and $R^2$ can join together to form a fused methyl-enedioxy ring or a fused 6-membered aromatic ring;

$R^3$ and $R^5$ are independently:
  a) H,
  b) $C_1$–$C_6$-alkyl, unsubstituted or substituted with one, two, or three substituents selected from oxo, X', Y' and Z',
  c) aryl, wherein aryl is defined as phenyl or naphthyl unsubstituted or substituted with one, two or three substituents selected from: X', Y' and Z', or
  d) $R^3$ and $R^5$ taken together can represent =O;

$R^4$ is:
  a) H, or
  b) $C_1$–$C_6$-alkyl,
  c) $C_1$–$C_6$-alkoxyl, or
  d) $R^4$ and $R^8$ can join together to form a 5- or 6-membered ring with —$CHR^9$—, —$CH_2CHR^9$—, or —$CHR^9CH_2$—;

—$X^1$—$X^2$—$X^3$—$X^4$— is:
  a) —$CR^6$=$CR^6$—$CR^{6a}$=$CR^6$—,
  b) —$CR^{6a}$=$CR^6$—$CR^6$=$CR^6$—,
  c) —$CR^6$=$CR^{6a}$—$CR^6$=$CR^6$—,
  d) —$CR^6$=$CR^6$—$CR^6$=$CR^{6a}$—,
  e) —N=$CR^6$—$CR^6$=$CR^6$—,
  f) —$CR^6$=N—$CR^6$=$CR^6$—,
  g) —$CR^6$=$CR^6$—N=$CR^6$—,
  h) —$CR^6$=$CR^6$—$CR^6$=N—,
  i) —N=$CR^6$—N=$CR^6$—,
  j) —$CR^6$=N—$CR^6$=N–,
  k) —$CR^6$=N—N=$CR^6$—, or
  l) —N=$CR^6$—$CR^6$=N—;

$X^5$ is N or CH;

$R^6$ and $R^{6a}$ are independently:
  a) H,
  b) halo(Br, Cl, I, or F),
  c) OH,
  d) SH,
  e) CN,
  f) $NO_2$,
  g) $N_3$,
  h) $N_2+BF_4$—,
  i) $R^9$, j) OR$^9$,
k) O(C=O)R$^9$,
l) O(C=O)OR$^9$,
m) O(C=O)NHR$^9$,
n) O(C=O)NR$^9$R$^{10}$,
o) SR$^9$,
p) S(O)R$^9$,
q) S(O)$_2$R$^9$,
r) C$_1$–C$_6$-alkyl, unsubstituted or substituted with one, two, or three substituents selected from R$^9$, R$^{10}$, and R$^{11}$,
s) C(=O)R$^9$,
t) C(=O)OR$^9$,
u) C(=O)NHR$^9$,
v) C(=O)NR$^9$R$^{10}$,
w) C(=O)N(OR$^9$)R$^{10}$,
x) NH$_2$,
y) NHR$^9$,
z) NHC$_1$–C$_6$-alkyl, unsubstituted or substituted with one, two, or three substituents selected from R$^9$, R$^{10}$, and R$^{11}$,
aa) NR$^9$R$^{10}$,
ab) NHC(=O)R$^9$,
ac) NR$^9$C(=O)R$^{10}$,
ad) NHC(=O)NHR$^9$,
ae) NR$^9$C(=O)NHR$^{10}$,
af) NR$^9$C(=O)NR$^{10}$R$^{11}$,
ag) SO$_2$NH$_2$,
ah) SO$_2$NHR$^9$,
al) SO$_2$NR$^9$R$^{10}$,
aj) NHSO$_2$R$^9$,
ak) NR$^9$SO$_2$R$^{10}$,
al) NHP(=O)(OC$_1$–C$_6$-alkyl)$_2$, or
am) R$^6$ and R$^{6a}$ when on adjacent carbons can be joined to form a 5- or 6-membered ring having the following bridging atoms, when read from right to left, or left to right:
  i) —CH=CH—CH=CH—,
  ii) —OCH$_2$O—,
  iii) —C(O)N(R$^9$)C(O)—,
  iv) —CH$_2$N(R$^9$)CH$_2$—,
  v) —N=CHNHC(O)—,
  vi) —C(O)NHCH=N—,
  vii) —C(O)OC(O)—,
  viii) —NHC(O)NHC(O)—,
  ix) —C(O)NHC(O)NH—,
  x) —N=CHNH—,
  xi) —NHCH=N—,
  xii) —NR$^9$CH=N—,
  xiii) —N=CHNR$^9$—, or
  xiv)

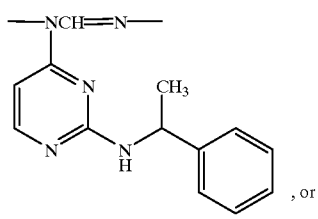
, or xv)

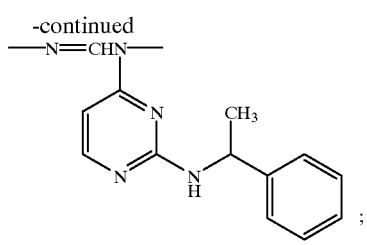
;

R$^7$ is:
a) H
b) R$^9$,
c) OR$^9$;
d) NH$_2$,
e) NHR$^9$, or
f) NR$^9$R$^{10}$;
X is O, S, SO, SO$_2$, NR$^8$;
Z is C=O, SO$_2$, P(=O)(OR$^9$) or a single bond; and
R$^8$ is:
a) H,
b) R$^9$,
c) SO$_2$R$^9$,
d) C(=O)R$^9$,
e) C(=O)OR$^9$,
f) C(=O)NHR$^9$,
g) C(=O)NR$^9$R$^{10}$, or
h) R$^8$ and R$^4$ can be joined to represent —C(R$^{16}$)$_2$—;
R$^9$, R$^{10}$ and R$^{11}$ are independently:
a) C$_1$–C$_6$-perfluoroalkyl,
b) C$_1$–C$_6$-alkyl, unsubstituted or substituted with one, two, or three substituents selected from oxo, X', Y' and Z',
c) C$_1$–C$_6$-alkenyl, unsubstituted or substituted with one, two, or three substituents selected from oxo, X', Y' and Z',
d) C$_2$–C$_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two, three or four substituents selected from oxo, X', Y', and Z', or
g) C$_3$–C$_6$-cycloalkyl, unsubstituted or substituted with one, two, or three substituents selected from oxo, X', Y' and Z';
X'Y' and Z' independently are selected from:
a) H,
b) halo,
c) CN,
d) NO$_2$,
e) hydroxy,
f) C$_1$–C$_6$-perfluoroalkyl,
g) C$_1$–C$_6$-alkoxyl, unsubstituted or substituted with aryl, wherein aryl is defined as phenyl or naphthyl,
h) (C=O)(C$_1$–C$_6$-alkyl), unsubstituted or substituted with aryl, wherein aryl is defined as phenyl or naphthyl,
i) (C=O)O(C$_1$–C$_6$-alkyl), unsubstituted or substituted with aryl, wherein aryl is defined as phenyl or naphthyl, j) (C=O)NH(C$_1$-C$_6$-alkyl), k) (C=O)N(C$_1$-C$_6$alkyl)$_2$, l) NH$_2$, m) NHC$_1$-C$_6$-alkyl, wherein alkyl is unsubstituted or substituted with aryl or NH$_2$, n) N(C$_1$-C$_6$-alkyl)$_2$, o) NHaryl, wherein aryl is defined as phenyl or naphthyl, unsubstituted or substituted with one, two, or three substituents selected from halo, phenyl, CN, NO$_2$, hydroxy, C$_1$-C$_6$-alkyl, C$_1$-C$_6$-alkoxyl, NH$_2$, NHC$_1$-C$_6$-alkyl, N(C$_1$-C$_6$-alkyl)$_2$, (C=O)(C$_1$-C$_6$-alkyl), (C=O)O(C$_1$-C$_6$-alkyl), (C=O)NH(C$_1$-C$_6$-alkyl), (C=O)N(C$_1$-C$_6$-alkyl)$_2$, NH(C=O)(C$_1$-C$_6$-alkyl), p) NHheterocyclyl, wherein heterocyclyl is unsubstituted or substituted with one, two or three substituents selected from halo, phenyl, oxo, CN, NO$_2$, hydroxy, C$_1$-C$_6$-alkyl, C$_1$-C$_6$-alkyl substituted with C$_3$-C$_7$-cycloalkyl, C$_1$-C$_6$-alkoxyl, NH$_2$, NHC$_1$-C$_6$-alkyl, N(C$_1$-C$_6$-alkyl)$_2$, (C=O)(C$_1$-C$_6$-alkyl), (C=O)O(C$_1$-C$_6$-alkyl), (C=O)OCH$_2$phenyl, (C=O)NH(C$_1$-C$_6$-alkyl), (C=O)N(C$_1$-C$_6$-alkyl)$_2$, NH(C=O)(C$_1$-C$_6$-alkyl), q) NHCHO, r) NH(C=O)(C$_1$-C$_6$-alkyl), s) NH(C=O)(OC$_1$-C$_6$-alkyl), t) aryl, wherein aryl is as defined above in o, u) C$_1$-C$_6$-alkyl, wherein alkyl is unsubstituted or substituted with hydroxy, C$_3$-C$_7$-cycloalkyl, aryl or heterocyclyl, wherein aryl is defined as above and heterocyclyl is as defined below, v) heterocyclyl, wherein heterocyclyl is as defined above in p, w) when two of X', Y' and Z' are on adjacent carbons they can join to form a methylenedioxy bridge, x) NH(C=O)aryl, y) —NR$^{14}$NHR$^{15}$, z) —S(O)x C$_1$-C$_6$-alkyl, aa) SO$_2$NH C$_1$-C$_6$-alkyl, or ab) CO$_2$H;

R$^{14}$ and R$^{15}$ are independently: H, C$_1$-C$_6$-alkyl, aryl or C$_1$-C$_6$-alkylaryl; or R$^{16}$ is:

a) H, b) (CH$_2$)$_x$aryl, wherein the aryl is unsubstituted or substituted with one or two substituents selected from X', Y', and Z';

c) (CH$_2$)$_x$heterocyclyl, wherein the heterocyclyl is unsubstituted or substituted with one or two substituents selected from X', Y', and Z'; or x is 0, 1 or 2.

2. A compound of Formula Ia

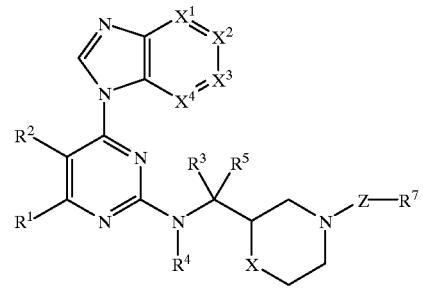

or pharmaceutically acceptable salts, hydrates, solvates, crystal forms and individual diastereomers thereof, wherein R$^1$ and R$^2$ are independently:

a) H, b) halo(Br, Cl, I, or F), c) OH, d) SH, e) CN, f) NO$_2$, g) R$^9$, h) OR$^9$, i) O(C=O)R$^9$, j) O(C=O)OR$^9$, k) O(C=O)NHR$^9$, l) O(C=O)NR$^9$R$^{10}$, m) SR$^9$, n) S(O)R$^9$, o) S(O)$_2$R$^9$, p) C(=O)R$^9$, q) C(=O)OR$^9$, r) C(=O)NHR$^9$, s) C(=O)NR$^9$R$^{10}$, t) NH$_2$, u) NHR$^9$, v) NR$^9$R$^{10}$, w) NHC(=O)R$^9$, x) NHC(=O)OR$^9$, y) NR$^9$C(=O)R$^{10}$, z) NR$^9$C(=O)NHR$^{10}$, aa) NR$^9$C(=O)NR$^{10}$R$^{11}$, ab) SO$_2$NHR$^9$, ac) SO$_2$NR$^9$R$^{10}$, ad) NHSO$_2$R$^9$, ae) NR$^9$SO$_2$R$^{10}$, or af) R$^1$ and R$^2$ can join together to form a fused methylenedioxy ring or a fused 6-membered aromatic ring;

R$^3$ and R$^5$ are independently:

a) H, b) C$_1$-C$_6$-alkyl, unsubstituted or substituted with one, two, or three substituents selected from oxo, X', Y' and Z', c) aryl, wherein aryl is defined as phenyl or naphthyl unsubstituted or substituted with one, two or three substituents selected from: X', Y' and Z', or d) R$^3$ and R$^5$ taken together can represent =O;

R$^4$ is:

a) H, or
b) $C_1$–$C_6$-alkyl, or
c) $C_1$–$C_6$-alkoxyl;

—$X^1$—$X^2$—$X^3$—$X^4$— is:
a) —$CR^6$=$CR^6$—$CR^{6a}$=$CR^6$—,
b) —$CR^{6a}$=$CR^6$—$CR^6$=$CR^6$—,
c) —N=$CR^6$—$CR^6$=$CR^6$—,
d) —$CR^6$=N—$CR^6$=$CR^6$—,
e) —$CR^6$=$CR^6$—N=$CR^6$—,
f) —$CR^6$=$CR^6$—$CR^6$=N—,
g) —N=$CR^6$—N=$CR^6$—,
h) —$CR^6$=N—$CR^6$=N—,
i) —$CR^6$=N—N=$CR^6$—, or
j) —N=$CR^6$—$CR^6$=N—;

$R^6$ and $R^{6a}$ are independently:
a) H,
b) halo(Br, Cl, I, or F),
c) OH,
d) SH,
e) CN,
f) $NO_2$,
g) $N_3$,
h) $N_2$+BF4—,
i) $R^9$,
j) $OR^9$,
k) O(C=O)$R^9$,
l) O(C=O)$OR^9$,
m) O(C=O)$NHR^9$,
n) O(C=O)$NR^9R^{10}$,
o) $SR^9$,
p) S(O)$R^9$,
q) S(O)$_2R^9$,
r) $C_1$–$C_6$-alkyl, unsubstituted or substituted with one, two, or three substituents selected from $R^9$, $R^{10}$, and $R^{11}$,
s) C(=O)$R^9$,
t) C(=O)$OR^9$,
u) C(=O)$NHR^9$,
v) C(=O)$NR^9R^{10}$,
w) C(=O)N($OR^9$)$R^{10}$,
x) $NH_2$,
y) $NHR^9$,
z) NH$C_1$–$C_6$-alkyl, unsubstituted or substituted with one, two, or three substituents selected from $R^9$, $R^{10}$, and $R^{11}$,
aa) $NR^9R^{10}$,
ab) NHC(=O)$R^9$,
ac) $NR^9$C(=O)$R^{10}$,
ad) NHC(=O)$NHR^9$,
ae) $NR^9$C(=O)$NHR^{10}$,
af) $NR^9$C(=O)$NR^{10}R^{11}$,
ag) $SO_2NH_2$,
ah) $SO_2NHR^9$,
ai) $SO_2NR^9R^{10}$,
aj) $NHSO_2R^9$,
ak) $NR^9SO_2R^{10}$, or
al) NHP(=O)(O$C_1$–$C_6$-alkyl)$_2$,
am) $R^6$ and $R^{6a}$ when on adjacent carbons can be joined to form a 5- or 6-membered ring having the following bridging atoms, when read from right to left, or left to right:

i) —CH=CH—CH=CH—,
ii) —$OCH_2O$—,
iii) —C(O)N($R^9$)C(O)—,
iv) —$CH_2$N($R^9$)$CH_2$—,
v) —N=CHNHC(O)—,
vi) —C(O)NHCH=N—,
vii) —C(O)OC(O)—,
viii) —NHC(O)NHC(O)—,
ix) —C(O)NHC(O)NH—,
x) —N=CHNH—,
xi) —N=CH$NR^9$—, or
xii)

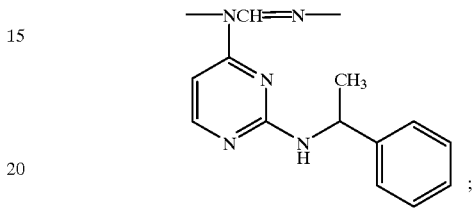

$R^7$ is:
a) $R^9$,
b) $OR^9$,
c) $NH_2$,
d) $NHR^9$, or
e) $NR^9R^{10}$;

X is O, S, SO, $SO_2$, $NR^8$;
Z is C=O, $SO_2$, P(=O)($OR^9$) or a single bond;
$R^8$ is:
a) H,
b) $R^9$,
c) $SO_2R^9$,
d) C(=O)$R^9$,
e) C(=O)$OR^9$,
f) C(=O)$NHR^9$,
f) C(=O)$NR^9R^{10}$;

$R^9$, $R^{10}$ and $R^{11}$ are independently:
a) $C_1$–$C_6$-perfluoroalkyl,
b) $C_1$–$C_6$-alkyl, unsubstituted or substituted with one, two, or three substituents selected from oxo, X', Y' and Z',
c) $C_2$–$C_6$-alkenyl, unsubstituted or substituted with one, two, or three substituents selected from oxo, X', Y' and Z',
d) $C_2$–$C_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two or three substituents selected from oxo, X', Y', and Z', or
g) $C_3$–$C_6$-cycloalkyl, unsubstituted or substituted with one, two, or three substituents selected from oxo, X', Y' and Z';

X', Y' and Z' independently are selected from:
a) H,
b) halo,
c) CN, d) $NO_2$,
e) hydroxy,
f) $C_1$–$C_6$-perfluoroalkyl,
g) $C_1$–$C_6$-alkoxyl, unsubstituted or substituted with aryl, wherein aryl is defined as phenyl or naphthyl,
h) (C=O)($C_1$–$C_6$-alkyl), unsubstituted or substituted with aryl, wherein aryl is defined as phenyl or naphthyl,
i) (C=O)O($C_1$–$C_6$-alkyl), unsubstituted or substituted with aryl, wherein aryl is defined as phenyl or naphthyl,
j) (C=O)NH($C_1$–$C_6$-alkyl),
k) (C=O)N($C_1$–$C_6$-alkyl)$_2$,
l) $NH_2$,
m) $NHC_1$–$C_6$-alkyl,
n) N($C_1$–$C_6$-alkyl)$_2$,
o) NHaryl, wherein aryl is defined as phenyl or naphthyl, unsubstituted or substituted with one, two, or three substituents selected from halo, phenyl, CN, $NO_2$, hydroxy, $C_1$–$C_6$-alkyl, $C_1$–$C_6$-alkoxyl, $NH_2$, $NHC_1$–$C_6$-alkyl, N($C_1$–$C_6$-alkyl)$_2$, (C=O)($C_1$–$C_6$-alkyl), (C=O)O($C_1$–$C_6$-alkyl), (C=O)NH($C_1$–$C_6$-alkyl), (C=O)N($C_1$–$C_6$-alkyl)$_2$, NH(C=O)($C_1$–$C_6$-alkyl),
p) NHheterocyclyl, wherein heterocyclyl is unsubstituted or substituted with one, two or three substituents selected from halo, phenyl, oxo, CN, $NO_2$, hydroxy, $C_1$–$C_6$-alkyl, $C_1$–$C_6$-alkoxyl, $NH_2$, $NHC_1$–$C_6$-alkyl, N($C_1$–$C_6$-alkyl)$_2$, (C=O)($C_1$–$C_6$-alkyl), (C=O)O($C_1$–$C_6$-alkyl), (C=O)OCH$_2$phenyl, (C=O)NH($C_1$–$C_6$-alkyl), (C=O)N($C_1$–$C_6$-alkyl)$_2$, NH(C=O)($C_1$–$C_6$-alkyl),
q) NHCHO,
r) NH(C=O)($C_1$–$C_6$-alkyl),
s) NH(C=O)(O$C_1$–$C_6$-alkyl),
t) aryl, wherein aryl is as defined above in o,
u) $C_1$–$C_6$-alkyl, wherein alkyl is unsubstituted or substituted with aryl or heterocyclyl, wherein aryl is defined as above and heterocyclyl is as defined below,
v) heterocyclyl, wherein heterocyclyl is as defined above in p, or
w) when two of X', Y' and Z' are on adjacent carbons they can join to form a methylenedioxy bridge.

3. The compound of Formula Ib:

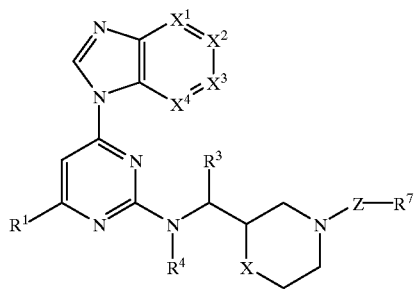

wherein $R^1$, $R^3$, $R^5$ and Z are as defined below and all other substituents are as defined in claim 2; or pharmaceutically acceptable salts, hydrates, solvates, crystal forms and individual diastereomers thereof, wherein
$R^1$ is:
a) H,
b) $R^9$,
c) $NH_2$,
d) $NHR^9$, or
e) $NR^9R^{10}$;
$R^3$ is:
a) H, or
b) $C_1$–$C_6$-alkyl, unsubstituted or substituted with one, two, or three substituents selected from oxo, X', Y' and Z';
X is O or $NR^8$; and
Z is C=O, $SO_2$, or a single bond.

4. The compound of Formula Ib:

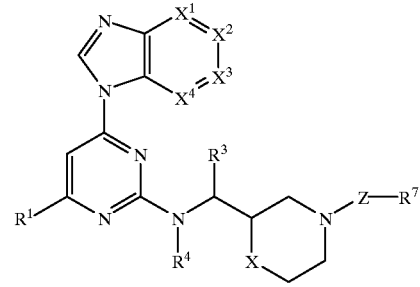

wherein —$X^1$—$X^2$—$X^3$—$X^4$—, $R^6$ and $R^{6a}$ are as defined below and all other substituents are as defined in claim 3; or pharmaceutically acceptable salts, hydrates, solvates, crystal forms and individual diastereomers thereof, wherein
—$X^1$—$X^2$—$X^3$—$X^4$— is:
a) —$CR^6$=$CR^6$—$CR^{6a}$=$CR^6$—,
b) —$CR^{6a}$=$CR^6$—$CR^6$=$CR^6$—,
c) —N=$CR^6$—$CR^6$=$CR^6$—, or
d) —$CR^6$=N—$CR^6$=$CR^6$—; and $R^6$ and $R^{6a}$ are independently:
a) H,
b) halo (Br, Cl, I, or F),
c) $R^9$,
d) $OR^9$,
e) $C_1$–$C_6$-alkyl, unsubstituted or substituted with one, two, or three substituents selected from $R^9$, $R^{10}$, and $R^{11}$,
f) $NH_2$,
g) $NHR^9$,
h) $NHC_1$–$C_6$-alkyl, unsubstituted or substituted with one, two, or three substituents selected from $R^9$, $R^{10}$, and $R^{11}$,
i) $NR^9R^{10}$,
j) NHC(=O)$R^9$,
k) $NR^9$C(=O)$R^{10}$,
l) $NR^9$C(=O)$NHR^{10}$,
m) $NR^9$C(=O)$NR^{10}R^{11}$,
n) $NHSO_2R^9$,
o) $NR^9SO_2R^{10}$, or
p) $R^6$ and $R^{6a}$ when on adjacent carbons can be joined to form a 5- or 6-membered ring having the following bridging atoms, when read from right to left, or left to right:

i) —N=CHNH—,
ii) —N=CHNR⁹—, or
iii)

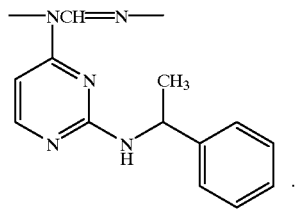

5. The compound of Formula Ib:

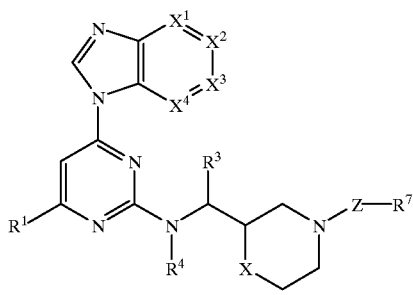

wherein —X¹—X²—X³—X⁴13, R⁶, R⁶ᵃ, R⁷, and R⁸ are as defined below and all other substituents are as defined in claim 4; or pharmaceutically acceptable salts, hydrates, solvates, crystal forms and individual diastereomers thereof, wherein
—X¹—X²—X³—X⁴— is:
 a) —CH=CR⁶—CR⁶ᵃ=CH—, or
 b) —CR⁶ᵃ=CR⁶—CH=CH—;
R⁶ and R⁶ᵃ are as defined below such that one and only one of R⁶ and R⁶ᵃ is other than H, except when R⁶ and R⁶ᵃ are as defined in (p):
 a) H,
 b) halo(Br, Cl, I, or F),
 c) R⁹,
 d) OR⁹,
 e) C₁–C₆-alkyl, unsubstituted or substituted with one, two, or three substituents selected from R⁹, R¹⁰, and R¹¹,
 f) NH₂,
 g) NHR⁹,
 h) NHC₁–C₆-alkyl, unsubstituted or substituted with one, two, or three substituents selected from R⁹, R¹⁰, and R¹¹,
 i) NR⁹R¹⁰,
 j) NHC(=O)R⁹,
 k) NR⁹C(=O)R¹⁰,
 l) NR⁹C(=O)NHR¹⁰,
 m) NR⁹C(=O)NR¹⁰R¹¹,
 n) NHSO₂R⁹,
 o) NR⁹SO₂R¹⁰, or
 p) R⁶ and R⁶ᵃ when on adjacent carbons can be joined to form a 5- or 6-membered ring having the following bridging atoms, when read from right to left, or left to right:

i) —N=CHNH—,
ii) —N=CHNR⁹—, or
iii)

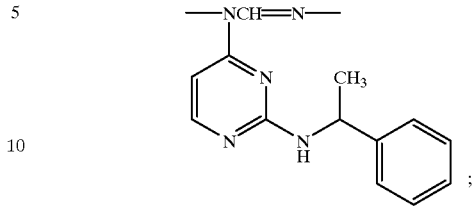

R⁷ is:
 a) R⁹,
 b) OR⁹,
 c) NH₂,
 d) NHR⁹, or
 e) NR⁹R¹⁰; and
R⁸ is H, or R⁹.

6. The compound of Formnula Ic:

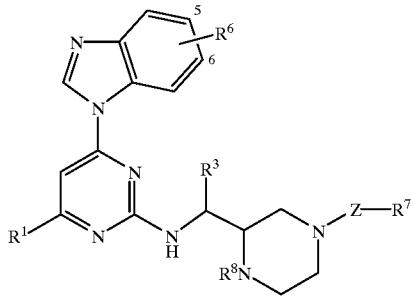

wherein R¹, R³, R⁶ (attached at the 5- or 6-position of the benzimidazole), R⁸, and Z are as defined herein and all other substituents are as defined in claim 5; or pharmaceutically acceptable salts, hydrates, solvates, crystal forms and individual diastereomers thereof, wherein
R¹ is:
 a) H, or
 b) R⁹;
R³ is:
 a) H, or
 b) C₁–C₆-alkyl;
R⁶ is:
 a) H,
 b) halo(Br, Cl, I, or F),
 c) R⁹,
 d) OR⁹,
 e) C₁–C₆-alkyl, unsubstituted or substituted with one, two, or three substituents selected from R⁹, R¹⁰, and R¹¹,
 f) NH₂,
 g) NHR⁹,
 h) NHC₁–C₆-alkyl, unsubstituted or substituted with one, two, or three substituents selected from R⁹, R¹⁰, and R¹¹,
 i) NR⁹R¹⁰,
 j) NHC(=O)R⁹,
 k) NR⁹C(=O)R¹⁰,
 l) NR⁹C(=O)NHR¹⁰, m) NR⁹C(=O)NR¹⁰R¹¹, n) NHSO₂R⁹, or o) NR⁹SO₂R¹⁰;

Z is C=O, SO₂, or a single bond; and

R⁸ is:

a) H, or b) R⁹.

7. The compound of Formula Id:

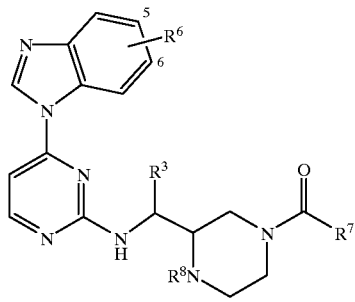

wherein R⁶ (attached at the 5- or 6-position of the benzimidazole), and R⁷ are as defined herein and all other substituents are as defined in claim 6; or pharmaceutically acceptable salts, hydrates, solvates, crystal forms and individual diastereomers thereof, wherein R⁶ is:

a) H, b) halo(Br, Cl, I, or F), c) R⁹, d) OR⁹, e) C₁–C₆-alkyl, unsubstituted or substituted with one, two, or three substituents selected from R⁹, R¹⁰, and R¹¹, f) NH₂, g) NHR⁹, h) NHC₁–C₆-alkyl, unsubstituted or substituted with one, two, or three substituents selected from R⁹, R¹⁰, and R¹¹, i) NR⁹R¹⁰, j) NHC(=O)R⁹, k) NR⁹C(=O)R¹⁰, l) NR⁹C(=O)NHR¹⁰, m) NR⁹C(=O)NR¹⁰R¹¹, n) NHSO₂R⁹, or o) NR⁹SO₂R¹⁰; and R⁷ is:

a) R⁹, d) NHR⁹, or e) NR⁹R¹⁰.

8. The compound of Formula Ie:

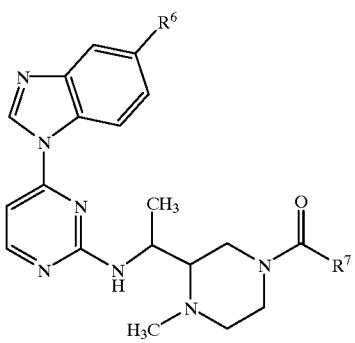

wherein R⁶ and R⁷ are as defined herein and all other substituents are as defined in claim 7; or pharmaceutically acceptable salts, hydrates, solvates, crystal forms and individual diastereomers thereof, wherein R⁶ is:

a) H, b) halo(Br, Cl, I, or F), c) R⁹, d) OR⁹, e) C₁–C₆-alkyl, unsubstituted or substituted with one, two, or three substituents selected from R⁹, R¹⁰, and R¹¹, f) NH₂, g) NHR⁹, h) NHC₁–C₆-alkyl, unsubstituted or substituted with one, two, or three substituents selected from R⁹, R¹⁰, and R¹¹, i) NR⁹R¹⁰, j) NHC(=O)R⁹, k) NR⁹C(=O)R¹⁰, l) NR⁹C(=O)NHR¹⁰, m) NR⁹C(=O)NR¹⁰R¹¹, n) NHSO₂R⁹, or o) NR⁹SO₂R¹⁰; and R⁷ is NUR⁹.

9. The compound of Formula Ie:

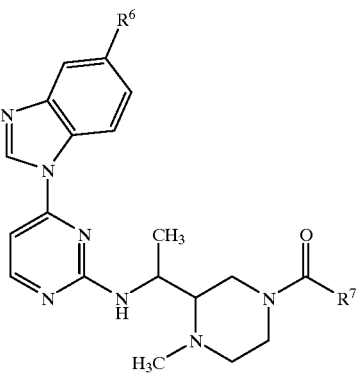

wherein R⁶ and R⁷ are as defined herein and all other substituents are as defined in claim 8; or pharmaceutically acceptable salts, hydrates, solvates, crystal forms and individual diastereomers thereof, wherein $R^6$ is:
 a) H,
 b) phenyl, unsubstituted or substituted with one, two, or three substituents selected from X', Y' and Z',
 c) pyridyl, unsubstituted or substituted with one, two or three substituents selected from X', Y', and Z',
 d) pyridazinyl, unsubstituted or substituted with one, two or three substituents selected from X', Y', and Z',
 e) pyrimidinyl, unsubstituted or substituted with one, two or three substituents selected from X', Y', and Z',
 f) imidazolidinyl, unsubstituted or substituted with one, two or three substituents selected from oxo, X', Y', and Z',
 g) 1,3-diazobicyclo[3.3.0]octan-2-onyl,
 h) 1,3-diazobicyclo[4.3.0]nonan-2-onyl,
 i) $NH_2$,
 j) $NHR^9$,
 k) $NHC_1$–$C_6$-alkyl, unsubstituted or substituted with one, two, or three substituents selected from $R^9$, $R^{10}$, and $R^{11}$,
 l) $NR^9R^{10}$,
 m) $NHC(=O)R^9$,
 n) $NR^9C(=O)R^{10}$,
 o) $NR^9C(=O)NHR^{10}$,
 p) $NR^9C(=O)NR^{10}R^{11}$,
 q) $NHSO_2R^9$, or
 r) $NR^9SO_2R^{10}$; and
$R^7$ is: NHaryl, wherein aryl is defined as phenyl or naphthyl, unsubstituted or substituted with one, two, or three substituents selected from X', Y' and Z'.

10. The compound of Formula Ie:

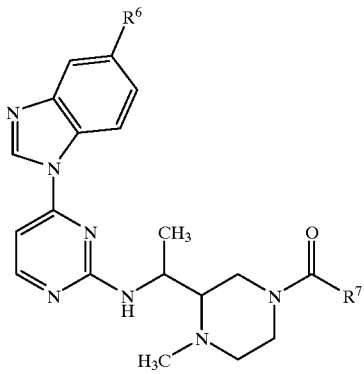

wherein $R^6$ and $R^7$ are as defined herein and all other substituents are as defined in claim 7; or pharmaceutically acceptable salts, hydrates, solvates, crystal forms and individual diastereomers thereof, wherein
$R^6$ is:
 a) phenyl, unsubstituted or substituted with one, two, or three substituents selected from X', Y' and Z',
 b) pyridyl, unsubstituted or substituted with one, two or three substituents selected from X', Y', and Z',
 c) pyridazinyl, unsubstituted or substituted with one, two or three substituents selected from X', Y', and Z',
 d) pyrimidinyl, unsubstituted or substituted with one, two or three substituents selected from X', Y', and Z',
 e) imidazolidinyl, unsubstituted or substituted with one, two or three substituents selected from oxo, X', Y', and Z',
 f) 1,3-diazobicyclo[3.3.0]octan-2-onyl, or
 g) 1,3-diazobicyclo[4.3.0]nonan-2-onyl; and
$R^7$ is $NHR^9$.

11. The compound of Formula Ie:

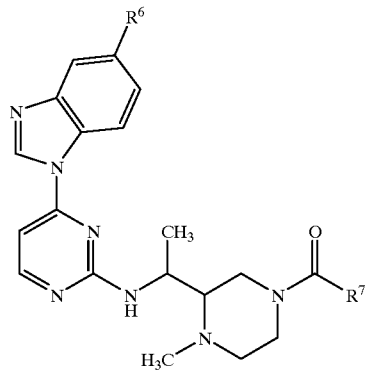

wherein $R^6$ and $R^7$ are as defined herein and all other substituents are as defined in claim 9; or pharmaceutically acceptable salts, hydrates, solvates, crystal forms and individual diastereomers thereof, wherein
$R^6$ is:
 a) phenyl, unsubstituted or substituted with one, two, or three substituents selected from X', Y' and Z',
 b) pyridyl, unsubstituted or substituted with one, two or three substituents selected from X', Y', and Z',
 c) pyridazinyl, unsubstituted or substituted with one, two or three substituents selected from X', Y', and Z',
 d) pyrimidinyl, unsubstituted or substituted with one, two or three substituents selected from X', Y', and Z',
 e) imidazolidinyl, unsubstituted or substituted with one, two or three substituents selected from oxo, X', Y', and Z',
 f) 1,3-diazobicyclo[3.3.0]octan-2-onyl, or
 g) 1,3-diazobicyclo[4.3.0]nonan-2-onyl; and
$R^7$ is: NHaryl, wherein aryl is defined as phenyl or naphthyl, unsubstituted or substituted with one, two, or three substituents selected from X', Y' and Z'.

12. The compound of Formula If:

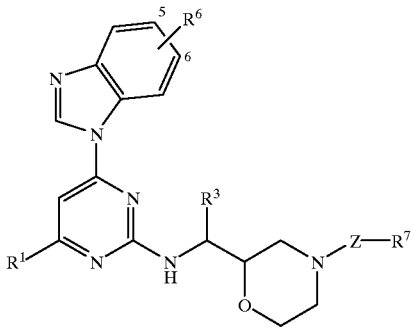

wherein $R^1$, $R^3$, $R^6$ (attached at the 5- or 6-position of the benzimidazole), $R^7$, and Z are as defined herein and all other substituents are as defined in claim 4; or pharmaceutically acceptable salts, hydrates, solvates, crystal forms and individual diastereomers thereof, wherein
$R^1$ is:
 a) H, or
 b) $R^9$;

$R^3$ is:
- a) H, or
- b) $C_1$–$C_6$-alkyl;

$R^6$ is:
- a) H,
- b) halo(Br, Cl, I, or F),
- c) $R^9$,
- d) $OR^9$,
- e) $C_1$–$C_6$-alkyl, unsubstituted or substituted with one, two, or three substituents selected from $R^9$, $R^{10}$, and $R^{11}$,
- f) $NH_2$,
- g) $NHR^9$,
- h) $NHC_1$–$C_6$-alkyl, unsubstituted or substituted with one, two, or three substituents selected from $R^9$, $R^{10}$, and $R^{11}$,
- i) $NR^9R^{10}$,
- j) $NHC(=O)R^9$,
- k) $NR^9C(=O)R^{10}$,
- l) $NR^9C(=O)NHR^{10}$,
- m) $NR^9C(=O)NR^{10}R^{11}$,
- n) $NHSO_2R^9$, or
- o) $NR^9SO_2R^{10}$;

$R^7$ is:
- a) $R^9$,
- b) $OR^9$,
- c) $NH_2$,
- d) $NHR^9$, or
- e) $NR^9R^{10}$; and Z is C=O, $SO_2$, or a single bond.

13. The compound of Formula Ig:

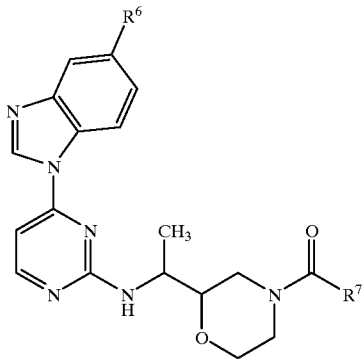

wherein $R^6$ and $R^7$ are as defined herein and all other substituents are as defined in claim 12; or pharmaceutically acceptable salts, hydrates, solvates, crystal forms and individual diastereomers thereof, wherein $R^6$ is:
- a) H,
- b) phenyl, unsubstituted or substituted with one, two, or three substituents selected from X', Y' and Z',
- c) pyridyl, unsubstituted or substituted with one, two or three substituents selected from X', Y', and Z',
- d) pyridazinyl, unsubstituted or substituted with one, two or three substituents selected from X', Y', and Z',
- e) pyrimidinyl, unsubstituted or substituted with one, two or three substituents selected from X', Y', and Z',
- f) imidazolidinyl, unsubstituted or substituted with one, two or three substituents selected from oxo, X', Y', and Z',
- g) 1,3-diazobicyclo[3.3.0]octan-2-onyl,
- h) 1,3-diazobicyclo[4.3.0]nonan-2-onyl,
- i) $NH_2$,
- j) $NHR^9$,
- k) $NHC_1$–$C_6$-alkyl, unsubstituted or substituted with one, two, or three substituents selected from $R^9$, $R^{10}$, and $R^{11}$,
- l) $NR^9R^{10}$,
- m) $NHC(=O)R^9$,
- n) $NR^9C(=O)R^{10}$,
- o) $NR^9C(=O)NHR^{10}$,
- p) $NR^9C(=O)NR^{10}R^{11}$,
- q) $NHSO_2R^9$, or
- r) $NR^9SO_2R^{10}$; and $R^7$ is: NHaryl, wherein aryl is defined as phenyl or naphthyl, unsubstituted or substituted with one, two, or three substituents selected from X', Y' and Z'.

14. The compound of Formula Ig:

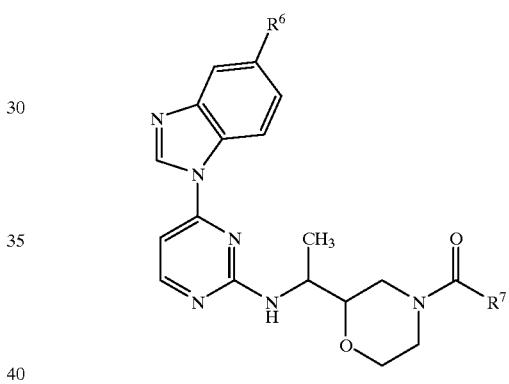

wherein $R^6$ and $R^7$ are as defined herein and all other substituents are as defined in claim 12; or pharmaceutically acceptable salts, hydrates, solvates, crystal forms and individual diastereomers thereof, wherein $R^6$ is:
- a) phenyl, unsubstituted or substituted with one, two, or three substituents selected from X', Y' and Z',
- b) pyridyl, unsubstituted or substituted with one, two or three substituents selected from X', Y', and Z',
- c) pyridazinyl, unsubstituted or substituted with one, two or three substituents selected from X', Y', and Z',
- d) pyrimidinyl, unsubstituted or substituted with one, two or three substituents selected from X', Y', and Z',
- e) imidazolidinyl, unsubstituted or substituted with one, two or three substituents selected from oxo, X', Y', and Z',
- f) 1,3-diazobicyclo[3.3.0]octan-2-onyl, or
- g) 1,3-diazobicyclo[4.3.0]nonan-2-onyl; and $R^7$ is $NHR^9$.

15. The compound of Formula Ig:

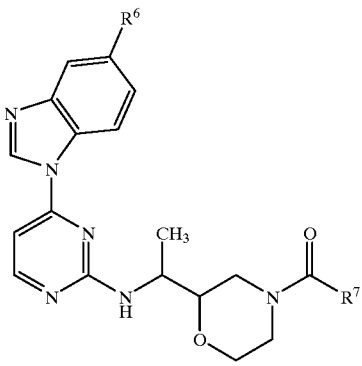

wherein $R^6$ and $R^7$ are as defined herein and all other substituents are as defined in claim 13; or pharmaceutically acceptable salts, hydrates, solvates, crystal forms and individual diastereomers thereof, wherein
$R^6$ is:
  a) phenyl, unsubstituted or substituted with one, two, or three substituents selected from X', Y' and Z',
  b) pyridyl, unsubstituted or substituted with one, two or three substituents selected from X', Y', and Z',
  c) pyridazinyl, unsubstituted or substituted with one, two or three substituents selected from X', Y', and Z',
  d) pyrimidinyl, unsubstituted or substituted with one, two or three substituents selected from X', Y', and Z',
  e) imidazolidinyl, unsubstituted or substituted with one, two or three substituents selected from oxo, X', Y', and Z',
  f) 1,3-diazobicyclo[3.3.0]octan-2-onyl, or
  g) 1,3-diazobicyclo[4.3.0]nonan-2-onyl; and
$R^7$ is: NHaryl, wherein aryl is defined as phenyl or naphthyl, unsubstituted or substituted with one, two, or three substituents selected from X', Y' and Z'.

16. The compound of Formula Ih:

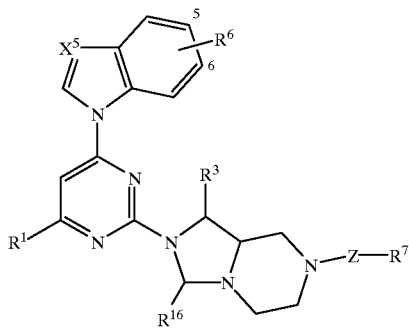

wherein $R^1$, $R^3$, $R^6$ (attached at the 5- or 6-position), $R^7$, $R^{16}$ and Z are as defined herein and all other substituents are as defined in claim 1; or pharmaceutically acceptable salts, hydrates, solvates, crystal forms and individual diastereomers thereof, wherein
$R^1$ is:
  a) H, or
  b) $R^9$;
$R^3$ is:
  a) H, or
  b) $C_1$–$C_6$-alkyl;

$R^6$ is:
  a) H,
  b) halo(Br, Cl, I, or F),
  c) $R^9$,
  d) $OR^9$,
  e) $C_1$–$C_6$-alkyl, unsubstituted or substituted with one, two, or three substituents selected from $R^9$, $R^{10}$, and $R^{11}$,
  f) $NH_2$,
  g) $NHR^9$,
  h) $NHC_1$–$C_6$-alkyl, unsubstituted or substituted with one, two, or three substituents selected from $R^9$, $R^{10}$, and $R^{11}$,
  i) $NR^9R^{10}$,
  j) $NHC(=O)R^9$,
  k) $NR^9C(=O)R^{10}$,
  l) $NR^9C(=O)NHR^{10}$,
  m) $NR^9C(=O)NR^{10}R^{11}$,
  n) $NHSO_2R^9$, or
  o) $NR^9SO_2R^{10}$;
Z is $C=O$, $SO_2$, or a single bond;
$R^7$ is:
  a) $R^9$,
  d) $NHR^9$, or
  e) $NR^9R^{10}$; and
$R^{16}$ is:
  a) H,
  b) phenyl,
  c) benzyl, or
  d) pyridyl.

17. A compound of claim 2, wherein the compound, or its pharmaceutically acceptable salt, hydrate, solvate, crystal form and individual diastereomer thereof is selected from the group consisting of:
2-[(1-(benzyloxycarbonyl)morpholin-2-yl)methylamino]-4-[benzimidazol-1-yl]pyrimidine,
2-[(1-(N-phenylcarbamoyl)morpholin-2-yl)methylamino]-4-[benzimidazol-1-yl]pyrimidine,
2-[(1-(N-naphth-1-ylcarbamoyl)morpholin-2-yl)methylamino]-4-[benzimidazol-1-yl]pyrimidine,
2-[(1-methanesulfonylmorpholin-2-yl)methylamino]-4-[benzimidazol-1-yl]pyrimidine,
2-[(1-(benzyloxycarbonyl)-4-(tert-butyloxycarbonyl)piperazin-2-yl)-methylamino]-4-[benzimidazol-1-yl]pyrimidine,
2-[(4-(N-naphth-1-ylcarbamoyl)piperazin-2-yl)methylamino]-4-[benzimidazol-1-yl]pyrimidine,
2-[(1-methyl-4-(N-naphth-1-ylcarbamoyl)piperazin-2-yl)methylamino]-4-[benzimidazol-1-yl]pyrimidine,
2-[1-(4-(N-naphth-1-yl-carbamoyl)morpholin-2-yl)ethylamino]-4-[benzimidazol-1-yl]pyrimidine,
2-[1-(1-methyl-4-(N-naphth-1-ylcarbamoyl)piperazin-2-yl)-ethylamino]-4-[benzimidazol-1-yl]pyrimidine,
2-[1-(1-methanesulfonyl-4-(N-naphth-1-ylcarbamoyl)piperazin-2-yl)ethylamino]-4-[benzimidazol-1-yl]pyrimidine,
2-[1-(1-Methyl-4-(N-naphth-1-ylcarbamoyl)piperazin-2-yl)ethylamino]-4-[5-(2-aminopyridin-4-yl)benzimidazol-1-yl]pyrimidine,
2-[1-(1-Methyl-4-(N-naphth-1-ylcarbamoyl)piperazin-2-yl)ethylamino]-4-[5-(2-aminopyrimidin-4-yl)benzimidazol-1-yl]pyrimidine,
2-[1-(1-Methyl-4-(N-naphth-1-ylcarbamoyl)piperazin-2-yl)ethylamino]-4-[5-(pyridin-4-yl)benzimidazol-1-yl]pyrimidine, 2-[1-(1-Methyl-4-(N-naphth-1-ylcarbamoyl)piperazin-2-yl) ethylamino]-4-[5-(pyridazin-3-yl)benzimidazol-1-yl] pyrimidine, 2-[1-(1-Methyl-4-(N-naphth-1-ylcarbamoyl)piperazin-2-yl) ethylamino]-4-[5-(3-N,N-dimethylpyridazin-6-yl) benzimidazol-1-yl]pyrimidine, 2-[1-(1-Methyl-4-(N-naphth-1-ylcarbamoyl)piperazin-2-yl) ethylamino]-4-[5-(2-aminopyrimidin-4-yl)benzimidazol-1-yl]-6-[2-methylphenyl]pyrimidine, 2-[1-(1-Methyl-4-(N-naphth-1-ylcarbamoyl )piperazin-2-yl)ethylamino]-4-[5-(2-aminopyrimidin-4-yl)benzimidazol-1-yl ]-6-[2-hydroxymethylphenyl] pyrimidine, 2-[1-(1-Methyl-4-(N-phenylcarbamoyl)piperazin-2-yl) ethylamino]-4-[5-(2-aminopyridin-4-yl)benzimidazol-1-yl]pyrimidine, 2-[1-(1-Methyl-4-(N-phenylcarbamoyl)piperazin-2-yl) ethylamino]-4-[5-(2-aminopyrimidin-4-yl)benzimidazol-1-yl]pyrimidine, 2-[1-(1-Methyl-4-(N-phenylcarbamoyl)piperazin-2-yl) ethylamino]-4-[5-(pyridin-4-yl)benzimidazol-1-yl] pyrimidine, 2-[1-(1-Methyl-4-(N-phenylcarbamoyl)piperazin-2-yl) ethylamino]-4-[5-(pyrimdazin-3-yl)benzimidazol-1-yl] pyrimidine, 2-[1-(1-Methyl-4-(N-phenylcarbamoyl)piperazin-2-yl) ethylamino]-4-[5-(3-N,N-dimethylpyridazin-6-yl) benzimidazol-1-yl]pyrimidine, 2-[1-(1-Methyl-4-(N-phenylcarbamoyl)piperazin-2-yl) ethylamino]-4-[5-(2-aminopyrimidin-4-yl)benzimidazol-1-yl]-6-[2-methylphenyl]pyrimidine; and 2-[1-(1-Methyl-4-(N-phenylcarbamoyl)piperazin-2-yl) ethylamino]-4-[5-(2-aminopyrimidin-4-yl)benzimidazol-1-yl]-6-[2-hydroxymethylphenyl]pyrimidine.

18. A method of treating a protein tyrosine kinase-associated disorder, comprising the administration of a therapeutically effective amount of at least one compound of the Formula I, or its pharmaceutically acceptable salts, hydrates, solvates, crystal forms and individual diastereomers thereof, as recited in claim 2, to a subject in need of such treatment.

19. The method of claim 18, wherein the protein tyrosine kinase-associated disorder is transplant rejection.

20. The method of claim 18, wherein the protein tyrosine kinase-associated disorder is rheumatoid arthritis.

21. The method of claim 18, wherein the protein tyrosine kinase-associated disorder is psoriasis.

22. The method of claim 18, wherein the protein tyrosine kinase-associated disorder is inflammatory bowel disease.

23. The method of claim 18, wherein the protein tyrosine kinase is Lck.

24. The method of claim 18, wherein the protein tyrosine kinase is Fyn(T) or Fyn(B).

25. The method of claim 18, wherein the protein tyrosine kinase is Lyn.

26. The method of claim 18, wherein the protein tyrosine kinase is Hck.

27. The method of claim 18, wherein the protein tyrosine kinase is Fgr.

28. The method of claim 18, wherein the protein tyrosine kinase is Src.

29. The method of claim 18, wherein the protein tyrosine kinase is Blk.

30. The method of claim 18, wherein the protein tyrosine kinase is Yes.

31. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 2, to a subject in need of such treatment.

32. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 2.

33. A process for making a pharmaceutical composition comprising a combination of a compound of the Formula I, or its pharmaceutically acceptable salts, hydrates, solvates, crystal forms salts and individual diastereomers thereof, as recited in claim 2 and a pharmaceutically acceptable carrier.

34. A method of treating a protein tyrosine kinase-associated disorder, comprising the administration of a therapeutically effective amount of at least one compound of the Formula I, or its pharmaceutically acceptable salts, hydrates, solvates, crystal forms and individual diastereomers thereof, as recited in claim 1, to a subject in need of such treatment.

35. The method of claim 34, wherein the protein tyrosine kinase-associated disorder is transplant rejection.

36. The method of claim 34, wherein the protein tyrosine kinase-associated disorder is rheumatoid arthritis.

37. The method of claim 34, wherein the protein tyrosine kinase-associated disorder is psoriasis.

38. The method of claim 34, wherein the protein tyrosine kinase-associated disorder is inflammatory bowel disease.

39. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 1, to a subject in need of such treatment.

40. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 1.

41. A process for making a pharmaceutical composition comprising a combination of a compound of the Formula I, or its pharmaceutically acceptable salts, hydrates, solvates, crystal forms salts and individual diastereomers thereof, as recited in claim 1 and a pharmaceutically acceptable carrier.

* * * * *